(12) United States Patent
Walberg et al.

(10) Patent No.: US 10,085,753 B2
(45) Date of Patent: Oct. 2, 2018

(54) CLIP APPLIER AND METHODS OF USE

(71) Applicant: Abbott Laboratories, Redwood City, CA (US)

(72) Inventors: Erik K. Walberg, San Jose, CA (US); Timothy C. Reynolds, Sunnyvale, CA (US); Brian A. Ellingwood, Sunnyvale, CA (US); Kai Yenkai Jair, Cupertino, CA (US); Anthony J. Pantages, San Jose, CA (US)

(73) Assignee: ABBOTT LABORATORIES, Abbott Park, IL (US)

( * ) Notice: Subject to any disclaimer, the term of this patent is extended or adjusted under 35 U.S.C. 154(b) by 441 days.

(21) Appl. No.: 14/732,977

(22) Filed: Jun. 8, 2015

(65) Prior Publication Data

US 2015/0265279 A1    Sep. 24, 2015

Related U.S. Application Data

(63) Continuation of application No. 13/898,202, filed on May 20, 2013, now Pat. No. 9,050,068, which is a
(Continued)

(51) Int. Cl.
*A61B 17/10* (2006.01)
*A61B 17/00* (2006.01)
(Continued)

(52) U.S. Cl.
CPC ............ *A61B 17/10* (2013.01); *A61B 17/0057* (2013.01); *A61B 17/064* (2013.01);
(Continued)

(58) Field of Classification Search
CPC ............ A61B 17/0057; A61B 17/1227; A61B 17/068
(Continued)

(56) References Cited

U.S. PATENT DOCUMENTS 287,046 A    10/1883    Norton
438,400 A    10/1890    Brennen
(Continued)

FOREIGN PATENT DOCUMENTS

AU    2003297432    7/2004
CA    2 339 060    2/2000
(Continued)

OTHER PUBLICATIONS

U.S. Appl. No. 12/113,092, filed Apr. 30, 2008, Ginn et al.
(Continued)

*Primary Examiner* — Kathleen Holwerda
*Assistant Examiner* — Christina Lauer
(74) *Attorney, Agent, or Firm* — Workman Nydegger; Randy Shen

(57) ABSTRACT

A method for delivering a closure element to an opening formed in a wall of a body lumen. The method includes inserting a distal end region of an apparatus into the opening in the wall of the body lumen, moving a third grasping portion toward the first grasping portion to limit movement of the distal end of the apparatus relative to the opening in the wall of the body lumen, and moving a second grasping portion toward the first grasping portion to advance the closure element distally. The second grasping portion and third grasping portion are movable toward the first grasping portion.

20 Claims, 26 Drawing Sheets

Related U.S. Application Data continuation of application No. 13/615,547, filed on Sep. 13, 2012, now Pat. No. 8,518,057, which is a continuation of application No. 11/427,297, filed on Jun. 28, 2006, now Pat. No. 8,313,497.

(60) Provisional application No. 60/696,069, filed on Jul. 1, 2005.

(51) Int. Cl.
*A61B 17/064* (2006.01)
*A61B 17/068* (2006.01)
*A61B 17/08* (2006.01)
*A61B 17/122* (2006.01)

(52) U.S. Cl.
CPC ........ *A61B 17/068* (2013.01); *A61B 17/0644* (2013.01); *A61B 17/083* (2013.01); *A61B 17/1227* (2013.01); *A61B 2017/00424* (2013.01); *A61B 2017/00672* (2013.01)

(58) Field of Classification Search
USPC .......................................... 606/213, 190, 142
See application file for complete search history.

(56) References Cited

U.S. PATENT DOCUMENTS

| | | |
|---|---|---|
| 556,082 A | 3/1896 | Boeddinghaus |
| 1,088,393 A | 2/1914 | Backus |
| 1,123,290 A | 1/1915 | Von Herff |
| 1,331,401 A | 2/1920 | Summers |
| 1,596,004 A | 8/1926 | De Bengoa |
| 1,647,958 A | 11/1927 | Ciarlante |
| 1,880,569 A | 10/1932 | Weis |
| 2,087,074 A | 7/1937 | Tucker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood et al. |
| 3,604,425 A | 9/1971 | Le Roy |
| 3,618,447 A | 11/1971 | Goins |
| 3,677,243 A | 7/1972 | Nerz |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,359,052 A | 11/1982 | Staub |
| 4,368,736 A | 1/1983 | Kaster |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,570,633 A | 2/1986 | Golden |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,635,637 A | 1/1987 | Schreiber |
| 4,644,956 A | 2/1987 | Morgenstern |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |

(56) References Cited

U.S. PATENT DOCUMENTS

| | | |
|---|---|---|
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,011,487 A | 4/1991 | Shichman |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,041,129 A | 8/1991 | Hayhurst et al. |
| 5,042,707 A | 8/1991 | Taheri |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,061,283 A | 10/1991 | Silvestrini |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,259 A | 12/1992 | Inoue |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,207,697 A | 5/1993 | Carusillo et al. |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,284,488 A | 2/1994 | Sideris |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,322,694 A | 6/1994 | Sixsmith |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| 5,383,897 A | 1/1995 | Wholey |
| RE34,866 E | 2/1995 | Kensey et al. |
| 5,391,174 A | 2/1995 | Weston |
| 5,392,978 A | 2/1995 | Valez et al. |
| 5,395,030 A | 3/1995 | Kuramoto et al. |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A | 11/1995 | Siska, Jr. et al. |
| 5,464,416 A | 11/1995 | Steckel |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,484,420 A | 1/1996 | Russo |
| 5,486,195 A | 1/1996 | Myers et al. |
| 5,496,332 A | 3/1996 | Sierra et al. |
| 5,497,933 A | 3/1996 | DeFonzo et al. |
| 5,507,744 A | 4/1996 | Tay et al. |
| 5,507,755 A | 4/1996 | Gresl et al. |
| 5,510,115 A | 4/1996 | Breillatt, Jr. et al. |
| 5,522,840 A | 6/1996 | Krajicek |

(56) References Cited

U.S. PATENT DOCUMENTS

| | | |
|---|---|---|
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,545,178 A | 8/1996 | Kensey et al. |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs et al. |
| 5,626,614 A | 5/1997 | Hart |
| 5,634,936 A | 6/1997 | Linden et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,697,943 A | 12/1997 | Sauer et al. |
| 5,700,273 A | 12/1997 | Buelna et al. |
| 5,709,224 A | 1/1998 | Behl et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,873 A | 4/1998 | MacLean |
| 5,746,753 A | 5/1998 | Sullivan et al. |
| 5,749,826 A | 5/1998 | Faulkner |
| 5,752,966 A | 5/1998 | Chang |
| 5,755,726 A | 5/1998 | Pratt et al. |
| 5,755,727 A | 5/1998 | Kontos |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,217 A | 11/1998 | Ryan |
| 5,830,221 A | 11/1998 | Stein et al. |
| 5,833,698 A | 11/1998 | Hinchliffe et al. |
| 5,843,164 A | 12/1998 | Frantzen et al. |
| 5,843,167 A | 12/1998 | Dwyer et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |
| 5,865,791 A | 2/1999 | Whayne et al. |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,696 A | 5/1999 | Rosenman |
| 5,904,697 A | 5/1999 | Gifford, III et al. |
| 5,904,703 A | 5/1999 | Gilson |
| 5,906,631 A | 5/1999 | Imran |
| 5,907,893 A | 6/1999 | Zadno-Azizi et al. |
| 5,908,149 A | 6/1999 | Welch et al. |
| 5,910,155 A | 6/1999 | Ratcliff et al. |
| 5,919,207 A | 7/1999 | Taheri |
| 5,922,009 A | 7/1999 | Epstein et al. |
| 5,928,208 A | 7/1999 | Chu et al. |
| 5,928,231 A | 7/1999 | Klein et al. |
| 5,928,251 A | 7/1999 | Aranyi et al. |
| 5,928,260 A | 7/1999 | Chin et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A * | 9/1999 | Hart ............ A61B 17/0469 606/144 |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,972,023 A | 10/1999 | Tanner et al. |
| 5,976,161 A | 11/1999 | Kirsch et al. |
| 5,976,174 A | 11/1999 | Ruiz |
| 5,984,934 A | 11/1999 | Ashby et al. |
| 5,984,948 A | 11/1999 | Hasson |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,007,574 A | 12/1999 | Pulnev et al. |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |

(56) References Cited

U.S. PATENT DOCUMENTS

| | | |
|---|---|---|
| 6,022,372 A | 2/2000 | Kontos |
| 6,024,750 A | 2/2000 | Mastri |
| 6,024,756 A | 2/2000 | Huebsch et al. |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,688 A | 5/2000 | Benderev et al. |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,071,300 A | 6/2000 | Brenneman et al. |
| 6,074,395 A | 6/2000 | Trott et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,090,130 A | 7/2000 | Nash et al. |
| 6,102,271 A | 8/2000 | Longo et al. |
| 6,110,184 A | 8/2000 | Weadock |
| 6,113,610 A | 9/2000 | Poncet |
| 6,113,611 A | 9/2000 | Allen et al. |
| 6,113,612 A | 9/2000 | Swanson et al. |
| 6,117,125 A | 9/2000 | Rothbarth et al. |
| 6,117,144 A | 9/2000 | Nobles et al. |
| 6,117,148 A | 9/2000 | Ravo |
| 6,117,157 A | 9/2000 | Tekulve |
| 6,117,159 A | 9/2000 | Huebsch et al. |
| 6,120,524 A | 9/2000 | Taheri |
| 6,126,675 A | 10/2000 | Schervinsky et al. |
| 6,136,010 A | 10/2000 | Modesitt et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,179,849 B1 | 1/2001 | Yencho et al. |
| 6,179,860 B1 | 1/2001 | Fulton, III et al. |
| 6,183,775 B1 | 2/2001 | Ventouras |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,210,418 B1 | 4/2001 | Storz et al. |
| 6,217,554 B1 | 4/2001 | Green |
| 6,220,248 B1 | 4/2001 | Voegele et al. |
| 6,221,102 B1 | 4/2001 | Baker et al. |
| 6,231,561 B1 | 5/2001 | Frazier et al. |
| 6,238,705 B1 | 5/2001 | Liu et al. |
| 6,241,740 B1 | 6/2001 | Davis et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,287,335 B1 | 9/2001 | Drasler et al. |
| 6,290,674 B1 | 9/2001 | Roue et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,355,061 B1 | 3/2002 | Quiachon et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,455,053 B1 | 9/2002 | Okada et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,485,504 B1 | 11/2002 | Johnson et al. |
| 6,488,692 B1 | 12/2002 | Spence et al. |
| 6,494,848 B1 | 12/2002 | Sommercorn et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,544,230 B1 | 4/2003 | Flaherty et al. |
| 6,547,806 B1 | 4/2003 | Ding |
| 6,551,319 B2 | 4/2003 | Lieberman |
| 6,558,349 B1 | 5/2003 | Kirkman |
| 6,569,173 B1 | 5/2003 | Blatter et al. |
| 6,569,185 B2 | 5/2003 | Ungs |
| 6,572,629 B2 | 6/2003 | Kalloo et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,596,013 B2 | 7/2003 | Yang et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,626,930 B1 | 9/2003 | Allen et al. |
| 6,632,197 B2 | 10/2003 | Lyon |

(56) References Cited

U.S. PATENT DOCUMENTS

| | | |
|---|---|---|
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,665 B2 | 1/2004 | Foley et al. |
| 6,676,671 B2 | 1/2004 | Robertson et al. |
| 6,676,685 B2 | 1/2004 | Pedros et al. |
| 6,679,894 B2 | 1/2004 | Damarati |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,743,195 B2 | 6/2004 | Zucker |
| 6,743,243 B1 | 6/2004 | Roy et al. |
| 6,743,259 B2 | 6/2004 | Ginn |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,758,855 B2 | 7/2004 | Fulton, III et al. |
| 6,767,356 B2 | 7/2004 | Kanner et al. |
| 6,776,784 B2 | 8/2004 | Ginn |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,391 B1 | 11/2005 | Gazzani |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,087,088 B2 | 8/2006 | Berg et al. |
| 7,094,245 B2 | 8/2006 | Adams et al. |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,175,646 B2 | 2/2007 | Brenneman et al. |
| 7,211,101 B2 | 5/2007 | Carley et al. |
| 7,220,268 B2 | 5/2007 | Blatter |
| 7,229,452 B2 | 6/2007 | Kayan |
| 7,261,716 B2 | 8/2007 | Strobel et al. |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,729 B2 | 10/2008 | Chanduszko |
| 7,445,596 B2 | 11/2008 | Kucklick et al. |
| 7,452,327 B2 | 11/2008 | Durgin et al. |
| 7,465,286 B2 | 12/2008 | Patterson et al. |
| 7,533,790 B1 | 5/2009 | Knodel et al. |
| 7,556,632 B2 | 7/2009 | Zadno |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| D611,144 S | 3/2010 | Reynolds |
| 7,678,135 B2 | 3/2010 | Maahs et al. |
| 7,780,696 B2 | 8/2010 | Daniel et al. |
| 7,806,904 B2 | 10/2010 | Carley et al. |
| 7,819,895 B2 | 10/2010 | Ginn et al. |
| 7,824,419 B2 | 11/2010 | Boraiah |
| 7,841,502 B2 | 11/2010 | Walberg et al. |
| 7,842,068 B2 | 11/2010 | Ginn |
| 7,850,709 B2 | 12/2010 | Cummins et al. |
| 7,850,797 B2 | 12/2010 | Carley et al. |
| 7,854,810 B2 | 12/2010 | Carley et al. |
| 7,857,828 B2 | 12/2010 | Jabba et al. |
| 7,867,249 B2 | 1/2011 | Palermo et al. |
| 7,875,054 B2 | 1/2011 | LaFontaine |
| 7,879,071 B2 | 2/2011 | Carley et al. |
| 7,887,555 B2 | 2/2011 | Carley et al. |
| 7,887,563 B2 | 2/2011 | Cummins et al. |
| 7,901,428 B2 | 3/2011 | Ginn et al. |
| 7,905,900 B2 | 3/2011 | Palermo |
| 7,918,873 B2 | 4/2011 | Cummins et al. |
| 7,931,669 B2 | 4/2011 | Ginn et al. |
| 7,931,671 B2 | 4/2011 | Tenerz |
| 7,967,842 B2 | 6/2011 | Bakos |
| 8,007,512 B2 | 8/2011 | Ginn et al. |
| 8,038,688 B2 * | 10/2011 | Modesitt ............ A61B 17/0057 606/139 |
| 8,083,768 B2 | 12/2011 | Ginn et al. |
| 8,103,327 B2 | 1/2012 | Harlev et al. |
| 8,105,352 B2 | 1/2012 | EgnelÖV |
| 8,128,644 B2 | 3/2012 | Carley et al. |
| 8,172,749 B2 | 5/2012 | Melsheimer |
| 8,182,497 B2 | 5/2012 | Carley et al. |
| 8,192,459 B2 | 6/2012 | Cummins et al. |
| 8,202,283 B2 | 6/2012 | Carley et al. |
| 8,202,293 B2 | 6/2012 | Ellingwood et al. |
| 8,202,294 B2 | 6/2012 | Jabba et al. |
| 8,211,122 B2 | 7/2012 | McIntosh |
| 8,216,260 B2 | 7/2012 | Lam et al. |
| 8,226,681 B2 | 7/2012 | Clark et al. |
| 8,236,026 B2 | 8/2012 | Carley et al. |
| 8,257,390 B2 | 9/2012 | Carley et al. |
| 8,303,624 B2 | 11/2012 | Fortson |
| 8,313,497 B2 | 11/2012 | Walberg et al. |
| 8,323,312 B2 | 12/2012 | Clark |
| 8,398,656 B2 | 3/2013 | Palermo et al. |

(56) References Cited

U.S. PATENT DOCUMENTS

| | | |
|---|---|---|
| 8,398,676 B2 | 3/2013 | Roorda et al. |
| 8,403,929 B2 | 3/2013 | Weisshaupt et al. |
| 8,409,228 B2 | 4/2013 | Blatter et al. |
| 8,469,995 B2 | 6/2013 | Cummins et al. |
| 8,486,092 B2 | 7/2013 | Carley et al. |
| 8,486,108 B2 | 7/2013 | Carley et al. |
| 8,518,057 B2 | 8/2013 | Walberg et al. |
| 8,529,587 B2 | 9/2013 | Ellingwood et al. |
| 8,556,930 B2 | 10/2013 | Ellingwood |
| 8,562,630 B2 | 10/2013 | Campbell |
| 8,574,244 B2 | 11/2013 | Reynolds |
| 8,579,932 B2 | 11/2013 | Pantages |
| 8,585,836 B2 | 11/2013 | Carley et al. |
| 8,590,760 B2 | 11/2013 | Cummins et al. |
| 8,597,325 B2 | 12/2013 | Ginn |
| 8,603,116 B2 | 12/2013 | Roorda |
| 8,603,136 B2 | 12/2013 | Ginn |
| 8,617,184 B2 | 12/2013 | Oepen |
| 8,657,852 B2 | 2/2014 | Roorda et al. |
| 8,672,953 B2 | 3/2014 | Reyes et al. |
| 8,690,910 B2 | 4/2014 | Carley et al. |
| 8,728,119 B2 | 5/2014 | Cummins |
| 8,758,396 B2 | 6/2014 | Ginn et al. |
| 8,758,398 B2 | 6/2014 | Carley |
| 8,758,399 B2 | 6/2014 | Fortson et al. |
| 8,758,400 B2 | 6/2014 | Ginn et al. |
| 8,784,447 B2 | 7/2014 | Coleman et al. |
| 8,808,310 B2 | 8/2014 | Jones et al. |
| 8,820,602 B2 | 9/2014 | Walberg et al. |
| 8,821,534 B2 | 9/2014 | Voss |
| 8,834,494 B2 | 9/2014 | Schorr et al. |
| 8,858,594 B2 | 10/2014 | Clark |
| 8,893,947 B2 | 11/2014 | Reynolds et al. |
| 8,905,937 B2 | 12/2014 | Ellingwood et al. |
| 8,926,633 B2 | 1/2015 | Carly |
| 8,926,656 B2 | 1/2015 | Palermo et al. |
| 8,956,388 B2 | 2/2015 | Ginn et al. |
| 8,992,549 B2 | 3/2015 | Bennett, III |
| 9,050,068 B2 | 6/2015 | Walberg et al. |
| 9,050,087 B2 | 6/2015 | Ginn et al. |
| 9,060,769 B2 | 6/2015 | Coleman et al. |
| 9,089,311 B2 | 7/2015 | Fortson et al. |
| 9,089,674 B2 | 7/2015 | Ginn et al. |
| 9,149,276 B2 | 10/2015 | Voss |
| 9,345,460 B2 | 5/2016 | Houser et al. |
| 9,364,209 B2 | 6/2016 | Voss |
| 2001/0007077 A1 | 7/2001 | Ginn et al. |
| 2001/0021855 A1 | 9/2001 | Levinson |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026208 A1* | 2/2002 | Roe ............ A61B 17/0057 606/190 |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0049453 A1 | 4/2002 | Nobles et al. |
| 2002/0056460 A1 | 5/2002 | Boyd et al. |
| 2002/0058960 A1 | 5/2002 | Hudson et al. |
| 2002/0062104 A1 | 5/2002 | Ashby et al. |
| 2002/0077657 A1 | 6/2002 | Ginn et al. |
| 2002/0082641 A1 | 6/2002 | Ginn et al. |
| 2002/0095164 A1 | 7/2002 | Andreas et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0151921 A1 | 10/2002 | Kanner et al. |
| 2002/0151963 A1 | 10/2002 | Brown et al. |
| 2002/0169475 A1 | 11/2002 | Gainor et al. |
| 2002/0183786 A1 | 12/2002 | Girton |
| 2002/0183787 A1 | 12/2002 | Wahr et al. |
| 2002/0198562 A1 | 12/2002 | Ackerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0018358 A1 | 1/2003 | Saadat |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0083679 A1 | 5/2003 | Grudem et al. |
| 2003/0088269 A1 | 5/2003 | Ashby |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158578 A1 | 8/2003 | Pantages et al. |
| 2003/0167063 A1 | 9/2003 | Kerr |
| 2003/0195504 A1 | 10/2003 | Tallarida et al. |
| 2003/0208211 A1 | 11/2003 | Kortenbach |
| 2004/0002763 A1 | 1/2004 | Phillips et al. |
| 2004/0009205 A1 | 1/2004 | Sawhney |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chanduszko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0147957 A1 | 7/2004 | Pierson, III |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0191277 A1 | 9/2004 | Sawhney et al. |
| 2004/0215232 A1 | 10/2004 | Belhe et al. |
| 2004/0225301 A1 | 11/2004 | Roop et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0148818 A1 | 7/2005 | Mesallum |
| 2005/0149066 A1 | 7/2005 | Stafford |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |

(56) References Cited

U.S. PATENT DOCUMENTS

| | | |
|---|---|---|
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0222614 A1 | 10/2005 | Ginn et al. |
| 2005/0228405 A1 | 10/2005 | Maruyama et al. |
| 2005/0228443 A1 | 10/2005 | Yassinzadeh |
| 2005/0245876 A1 | 11/2005 | Khosravi et al. |
| 2005/0256532 A1 | 11/2005 | Nayak et al. |
| 2005/0267495 A1 | 12/2005 | Ginn et al. |
| 2005/0267524 A1 | 12/2005 | Chanduszko |
| 2005/0273136 A1 | 12/2005 | Belef et al. |
| 2005/0273137 A1 | 12/2005 | Ginn |
| 2005/0283188 A1 | 12/2005 | Loshakove et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0064115 A1 | 3/2006 | Allen et al. |
| 2006/0069397 A1 | 3/2006 | Nobles et al. |
| 2006/0100664 A1 | 5/2006 | Pai et al. |
| 2006/0142784 A1 | 6/2006 | Kontos |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0195123 A1 | 8/2006 | Ginn et al. |
| 2006/0195125 A1 | 8/2006 | Sakakine et al. |
| 2006/0206146 A1 | 9/2006 | Tenerez |
| 2006/0217744 A1 | 9/2006 | Bender et al. |
| 2006/0229553 A1 | 10/2006 | Hammack et al. |
| 2006/0253037 A1 | 11/2006 | Ginn et al. |
| 2006/0253072 A1 | 11/2006 | Pai et al. |
| 2006/0287673 A1 | 12/2006 | Brett et al. |
| 2006/0287674 A1 | 12/2006 | Ginn et al. |
| 2006/0293698 A1 | 12/2006 | Douk |
| 2007/0005093 A1 | 1/2007 | Cox |
| 2007/0010851 A1 | 1/2007 | Chanduszko et al. |
| 2007/0027476 A1 | 2/2007 | Harris et al. |
| 2007/0027525 A1 | 2/2007 | Ben-Muvhar |
| 2007/0049968 A1 | 3/2007 | Sibbitt, Jr. et al. |
| 2007/0049970 A1 | 3/2007 | Belef et al. |
| 2007/0060858 A1 | 3/2007 | Sogard et al. |
| 2007/0060895 A1 | 3/2007 | Sibbitt, Jr. et al. |
| 2007/0060950 A1 | 3/2007 | Khosravi et al. |
| 2007/0073337 A1 | 3/2007 | Abbott et al. |
| 2007/0078302 A1 | 4/2007 | Ortiz et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0149996 A1 | 6/2007 | Coughlin |
| 2007/0167981 A1 | 7/2007 | Opolski et al. |
| 2007/0172430 A1 | 7/2007 | Brito et al. |
| 2007/0179527 A1 | 8/2007 | Eskuri et al. |
| 2007/0185529 A1 | 8/2007 | Coleman et al. |
| 2007/0185530 A1 | 8/2007 | Chin-Chen et al. |
| 2007/0203507 A1 | 8/2007 | McLaughlin et al. |
| 2007/0208376 A1 | 9/2007 | Meng |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0265658 A1 | 11/2007 | Nelson et al. |
| 2007/0275036 A1 | 11/2007 | Green, III et al. |
| 2007/0276488 A1 | 11/2007 | Wachter et al. |
| 2007/0282373 A1 | 12/2007 | Ashby et al. |
| 2008/0009794 A1 | 1/2008 | Bagaoisan et al. |
| 2008/0033459 A1 | 2/2008 | Shafi et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0082123 A1 | 4/2008 | Forsberg et al. |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0097509 A1 | 4/2008 | Beyar et al. |
| 2008/0114378 A1 | 5/2008 | Matsushita |
| 2008/0114395 A1 | 5/2008 | Mathisen et al. |
| 2008/0269802 A1 | 5/2008 | Coleman et al. |
| 2008/0177288 A1 | 7/2008 | Carlson |
| 2008/0208225 A1 | 8/2008 | Seibold et al. |
| 2008/0215089 A1 | 9/2008 | Williams et al. |
| 2008/0215090 A1 | 9/2008 | Gonzales et al. |
| 2008/0243148 A1 | 10/2008 | Mikkaichi et al. |
| 2008/0243182 A1 | 10/2008 | Bates et al. |
| 2008/0249504 A1 | 10/2008 | Lattouf et al. |
| 2008/0262541 A1 | 10/2008 | Sater et al. |
| 2008/0269801 A1 | 10/2008 | Coleman et al. |
| 2008/0287988 A1 | 11/2008 | Smith et al. |
| 2008/0294001 A1 | 11/2008 | Surti |
| 2008/0300628 A1 | 12/2008 | Ellingwood |
| 2008/0312667 A1 | 12/2008 | Drasler et al. |
| 2008/0312686 A1 | 12/2008 | Ellingwood |
| 2008/0312740 A1 | 12/2008 | Wachter et al. |
| 2009/0054912 A1 | 2/2009 | Heanue et al. |
| 2009/0062846 A1 | 3/2009 | Ken |
| 2009/0112306 A1 | 4/2009 | Bonsignore et al. |
| 2009/0132031 A1 | 5/2009 | Cook et al. |
| 2009/0137900 A1 | 5/2009 | Bonner et al. |
| 2009/0157101 A1 | 6/2009 | Reyes et al. |
| 2009/0171388 A1 | 7/2009 | Dave et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0259233 A1 | 10/2009 | Bogart et al. |
| 2009/0281555 A1 | 11/2009 | Stone |
| 2009/0287244 A1 | 11/2009 | Kokish |
| 2009/0312789 A1 | 12/2009 | Kassab et al. |
| 2010/0042118 A1 | 2/2010 | Garrison et al. |
| 2010/0042144 A1 | 2/2010 | Bennett |
| 2010/0114119 A1 | 5/2010 | McLawhorn et al. |
| 2010/0114156 A1 | 5/2010 | Mehl |
| 2010/0130965 A1 | 5/2010 | Sibbitt, Jr. et al. |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0185216 A1 | 7/2010 | Garrison et al. |
| 2010/0185234 A1 | 7/2010 | Fortson et al. |
| 2010/0249828 A1 | 9/2010 | Mavani et al. |
| 2011/0054492 A1 | 3/2011 | Clark |
| 2011/0082495 A1 | 4/2011 | Ruiz |
| 2011/0137340 A1 | 6/2011 | Cummins |
| 2011/0178548 A1 | 7/2011 | Tenerz |
| 2011/0190793 A1 | 8/2011 | Nobles et al. |
| 2011/0218568 A1 | 9/2011 | Voss |
| 2011/0270282 A1 | 11/2011 | Lemke |
| 2011/0288563 A1 | 11/2011 | Gianotti et al. |
| 2011/0313452 A1 | 12/2011 | Carley et al. |
| 2012/0101520 A1 | 4/2012 | Ginn et al. |
| 2012/0245623 A1 | 9/2012 | Kariniemi et al. |
| 2013/0053792 A1 | 2/2013 | Fischell et al. |
| 2013/0138144 A1 | 5/2013 | Yibarren |
| 2013/0178872 A1 | 7/2013 | Shriver |
| 2013/0190778 A1 | 7/2013 | Palermo |
| 2013/0310853 A1 | 11/2013 | Zaugg et al. |
| 2013/0338708 A1 | 12/2013 | Cummins et al. |
| 2014/0005692 A1 | 1/2014 | Ellingwood et al. |
| 2014/0018850 A1 | 1/2014 | Ellingwood |
| 2014/0039549 A1 | 2/2014 | Belsky et al. |
| 2014/0081318 A1 | 3/2014 | Houser et al. |
| 2014/0142624 A1 | 5/2014 | Pantages et al. |
| 2014/0222068 A1 | 8/2014 | Carley et al. |
| 2014/0222069 A1 | 8/2014 | Carley et al. |
| 2014/0309686 A1 | 10/2014 | Ginn et al. |
| 2014/0364900 A1 | 12/2014 | Fortson et al. |
| 2014/0364903 A1 | 12/2014 | Roorda et al. |

(56) References Cited

U.S. PATENT DOCUMENTS

| | | | |
|---|---|---|---|
| 2015/0073471 A1 | 3/2015 | Clark | |
| 2015/0080914 A1 | 3/2015 | Roundy et al. | |
| 2015/0190071 A1 | 7/2015 | Ellingwood et al. | |
| 2016/0120546 A1 | 5/2016 | Roundy et al. | |
| 2016/0151057 A1 | 6/2016 | Voss | |
| 2016/0174954 A1 | 6/2016 | Palermo et al. | |
| 2016/0192913 A1 | 7/2016 | Kokish | |
| 2016/0213357 A1 | 7/2016 | Mehl | |
| 2016/0242749 A1 | 8/2016 | Voss | |
| 2017/0020496 A1 | 1/2017 | Yribarren | |
| 2017/0020517 A1 | 1/2017 | Coleman et al. | |
| 2017/0049426 A1 | 2/2017 | Gianotti et al. | |
| 2017/0135680 A1 | 5/2017 | Pantages et al. | |
| 2017/0135684 A1 | 5/2017 | Carley et al. | |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/00046 | 1/1997 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/62234 | 8/2002 |
| WO | WO 02/98302 | 12/2002 |
| WO | WO 03/13363 | 2/2003 |
| WO | WO 03/13364 | 2/2003 |
| WO | WO 03/47434 | 6/2003 |
| WO | WO 03/71955 | 9/2003 |
| WO | WO 03/71956 | 9/2003 |
| WO | WO 03/71957 | 9/2003 |
| WO | WO 03/94748 | 11/2003 |
| WO | WO 03/101310 | 12/2003 |
| WO | WO 04/04578 | 1/2004 |
| WO | WO 04/12602 | 2/2004 |
| WO | WO 04/60169 | 7/2004 |
| WO | WO 04/69054 | 8/2004 |
| WO | WO 05/000126 | 1/2005 |
| WO | WO 05/006990 | 1/2005 |
| WO | WO 05/041782 | 5/2005 |
| WO | WO 05/063129 | 7/2005 |
| WO | WO 05/082256 | 9/2005 |
| WO | WO 05/092204 | 10/2005 |
| WO | WO 05/110240 | 11/2005 |
| WO | WO 05/112782 | 12/2005 |
| WO | WO 05/115251 | 12/2005 |
| WO | WO 05/115521 | 12/2005 |
| WO | WO 06/000514 | 1/2006 |
| WO | WO 06/026116 | 3/2006 |
| WO | WO 06/052611 | 5/2006 |
| WO | WO 06/052612 | 5/2006 |
| WO | WO 06/078578 | 7/2006 |
| WO | WO 06/083889 | 8/2006 |
| WO | WO 06/115901 | 11/2006 |
| WO | WO 06/115904 | 11/2006 |
| WO | WO 06/118877 | 11/2006 |
| WO | WO 07/05585 | 1/2007 |
| WO | WO 07/25014 | 3/2007 |
| WO | WO 07/81836 | 7/2007 |
| WO | WO 07/88069 | 8/2007 |
| WO | WO 08/031102 | 3/2008 |
| WO | WO 08/036384 | 3/2008 |
| WO | WO 08/074027 | 6/2008 |
| WO | WO 08/150915 | 12/2008 |
| WO | WO 09/079091 | 6/2009 |
| WO | WO 10/062693 | 6/2010 |
| WO | WO 10/081101 | 7/2010 |
| WO | WO 10/081102 | 7/2010 |
| WO | WO 10/081103 | 7/2010 |
| WO | WO 10/081106 | 7/2010 |

(56) References Cited

FOREIGN PATENT DOCUMENTS

| ZA | 200100527 | 1/2001 |
|---|---|---|
| ZA | 200100528 | 1/2001 |

OTHER PUBLICATIONS

U.S. Appl. No. 13/017,636, filed Jan. 31, 2011, Carley et al.
U.S. Appl. No. 60/693,531, filed Jun. 24, 2005, Carly.
U.S. Appl. No. 60/696,069, filed Jul. 1, 2005, Pantages et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 14/839,658, filed Aug. 31, 2015, Cummins et al.
U.S. Appl. No. 14/855,080, filed Sep. 15, 2015, Voss et al.
"Hand tool for forming telephone connections—comprises pliers with reciprocably driven ram crimping clip around conductors against anvil", Derwent-ACC-No. 1978-B8090A. (Jan. 10, 1978).
Database WPI; Section PQ, Week 200120; Derwent Publications Ltd., London GB; Class P31, AN 2001-203165; XP002199926 & ZA 200 100 528 A (Anthony T), Feb. 28, 2001 (Feb. 28, 2001) abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PHD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.

Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
Inlet Medical Inc. Brochure, pp. 1-2, referencing OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive. org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Swee Lian Tan, MD, PHD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

(56) References Cited

OTHER PUBLICATIONS

Tomoaki Hinohara, Percutaneous vascular surgery (Prostar® Plus and Techstar® for femoral artery site closure), Interventional Cardiology Newsletter, May-Jul. 1997, pp. 19-22, pp. 24-28, vol. 5—No. 3-4.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Office Action.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Office Action.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Examiner's Amendment.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.

(56) References Cited

OTHER PUBLICATIONS

U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/667,144, Jun. 6, 2011, Office Action.
U.S. Appl. No. 10/667,144, Oct. 28, 2011, Notice of Allowance.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/682,459, Apr. 1, 2011, Notice of Allowance.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/786,444, Jul. 11, 2013, Notice of Allowance.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 10/908,721, Jul. 18, 2013, Notice of Allowance.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/113,549, Jan. 4, 2011, Office Action.
U.S. Appl. No. 11/113,549, Mar. 14, 2014, Notice of Allowance.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/344,891, Jan. 22, 2013, Notice of Allowance.
U.S. Appl. No. 11/390,586, Jun. 24, 2009, Office Action.
U.S. Appl. No. 11/390,586, Jul. 6, 2010, Office Action.
U.S. Appl. No. 11/390,586, May 3, 2012, Notice of Allowance.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,141, Apr. 30, 2013, Office Action.
U.S. Appl. No. 11/396,141, Aug. 21, 2013, Office Action.
U.S. Appl. No. 11/396,141, Nov. 4, 2013, Notice of Allowance.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/396,731, Mar. 22, 2011, Office Action.
U.S. Appl. No. 11/396,731, Sep. 1, 2011, Office Action.
U.S. Appl. No. 11/396,731, Feb. 12, 2015, Office Action.
U.S. Appl. No. 11/396,731, Jul. 9, 2015, Notice of Allowance.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/411,925, Oct. 1, 2013, Office Action.
U.S. Appl. No. 11/411,925, Feb. 5, 2014, Notice of Allowance.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.
U.S. Appl. No. 11/427,297, Mar. 21, 2011, Office Action.
U.S. Appl. No. 11/427,297, Jun. 26, 2012, Notice of Allowance.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/427,309, Jun. 7, 2013, Notice of Allowance.

(56) References Cited

OTHER PUBLICATIONS

U.S. Appl. No. 11/455,993, Feb. 17, 2009, Office Action.
U.S. Appl. No. 11/455,993, Dec. 16, 2009, Office Action.
U.S. Appl. No. 11/455,993, Jan. 29, 2014, Office Action.
U.S. Appl. No. 11/455,993, Aug. 11, 2014, Notice of Allowance.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,325, Jul. 17, 2013, Office Action.
U.S. Appl. No. 11/532,325, Dec. 2, 2013, Office Action.
U.S. Appl. No. 11/532,325, Jan. 16, 2015, Notice of Allowance.
U.S. Appl. No. 11/532,576, Mar. 1, 2010, Office Action.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/674,930, Apr. 3, 2014, Notice of Allowance.
U.S. Appl. No. 11/675,462, Dec. 10, 2009, Office Action.
U.S. Appl. No. 11/675,462, Aug. 31, 2010, Office Action.
U.S. Appl. No. 11/675,462, Aug. 3, 2011, Office Action.
U.S. Appl. No. 11/675,462, Dec. 22, 2011, Notice of Allowance.
U.S. Appl. No. 11/744,089, Nov. 26, 2008, Office Action.
U.S. Appl. No. 11/744,089, Aug. 14, 2009, Office Action.
U.S. Appl. No. 11/744,089, Aug. 8, 2012, Office Action.
U.S. Appl. No. 11/744,089, Apr. 15, 2013, Office Action.
U.S. Appl. No. 11/744,089, Aug. 8, 2013, Notice of Allowance.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/767,818, Sep. 30, 2010, Office Action.
U.S. Appl. No. 11/767,818, Feb. 16, 2011, Office Action.
U.S. Appl. No. 11/767,818, Feb. 3, 2012, Notice of Allowance.
U.S. Appl. No. 11/852,190, Jun. 24, 2010, Office Action.
U.S. Appl. No. 11/852,190, Nov. 1, 2010, Office Action.
U.S. Appl. No. 11/852,190, Mar. 2, 2011, Office Action.
U.S. Appl. No. 11/852,190, Apr. 24, 2013, Office Action.
U.S. Appl. No. 11/852,190, Nov. 26, 2013, Office Action.
U.S. Appl. No. 11/852,190, Feb. 12, 2014, Notice of Allowance.
U.S. Appl. No. 11/958,281, Sep. 2, 2010, Office Action.
U.S. Appl. No. 11/958,281, Oct. 8, 2010, Office Action.
U.S. Appl. No. 11/958,281, Mar. 10, 2011, Office Action.
U.S. Appl. No. 11/958,295, Aug. 27, 2009, Office Action.
U.S. Appl. No. 11/958,295, May 25, 2010, Office Action.
U.S. Appl. No. 11/958,295, Jun. 13, 2014, Notice of Allowance.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,928, Oct. 25, 2010, Office Action.
U.S. Appl. No. 12/106,928, Jun. 28, 2013, Office Action.
U.S. Appl. No. 12/106,928, Dec. 2, 2013, Office Action.
U.S. Appl. No. 12/106,928, Mar. 25, 2014, Advisory Action.
U.S. Appl. No. 12/106,928, Oct. 3, 2014, Notice of Allowance.
U.S. Appl. No. 12/106,937, Mar. 30, 2009, Office Action.
U.S. Appl. No. 12/106,937, Nov. 18, 2009, Office Action.
U.S. Appl. No. 12/106,937, Jun. 28, 2013, Office Action.
U.S. Appl. No. 12/106,937, Jan. 22, 2014, Office Action.
U.S. Appl. No. 12/106,937, Mar. 5, 2015, Notice of Allowance.
U.S. Appl. No. 12/113,851, Apr. 27, 2010, Office Action.
U.S. Appl. No. 12/113,851, Jun. 24, 2010, Office Action.
U.S. Appl. No. 12/113,851, Dec. 16, 2010, Office Action.
U.S. Appl. No. 12/113,851, Apr. 27, 2011, Office Action.
U.S. Appl. No. 12/113,851, Mar. 29, 2012, Office Action.
U.S. Appl. No. 12/113,851, Mar. 17, 2014, Office Action.
U.S. Appl. No. 12/113,851, Aug. 21, 2014, Office Action.
U.S. Appl. No. 12/113,851, Feb. 20, 2015, Notice of Allowance.
U.S. Appl. No. 12/114,031, Oct. 5, 2010, Office Action.
U.S. Appl. No. 12/114,031, Nov. 22, 2010, Office Action.
U.S. Appl. No. 12/114,031, May 11, 2011, Office Action.
U.S. Appl. No. 12/114,031, Aug. 2, 2011, Office Action.
U.S. Appl. No. 12/114,031, Mar. 6, 2012, Office Action.
U.S. Appl. No. 12/114,031, Mar. 10, 2014, Office Action.
U.S. Appl. No. 12/114,091, Oct. 27, 2010, Office Action.
U.S. Appl. No. 12/114,091, Dec. 17, 2010, Office Action.
U.S. Appl. No. 12/114,091, Jul. 7, 2011, Office Action.
U.S. Appl. No. 12/114,091, Apr. 5, 2012, Office Action.
U.S. Appl. No. 12/114,091, Nov. 8, 2012, Office Action.
U.S. Appl. No. 12/114,091, Feb. 12, 2015, Office Action.
U.S. Appl. No. 12/114,091, Jul. 23, 2015, Office Action.
U.S. Appl. No. 12/122,603, Mar. 3, 2011, Office Action.
U.S. Appl. No. 12/122,603, Apr. 22, 2011, Office Action.
U.S. Appl. No. 12/122,603, Sep. 23, 2011, Office Action.
U.S. Appl. No. 12/122,603, Nov. 20, 2013, Office Action.
U.S. Appl. No. 12/122,603, Apr. 30, 2014, Office Action.
U.S. Appl. No. 12/122,603, Apr. 9, 2015, Office Action.
U.S. Appl. No. 12/135,858, Jul. 13, 2011, Office Action.
U.S. Appl. No. 12/135,858, Feb. 16, 2012, Office Action.
U.S. Appl. No. 12/143,020, May 11, 2011, Office Action.
U.S. Appl. No. 12/143,020, Aug. 31, 2011, Office Action.
U.S. Appl. No. 12/143,020, Feb. 23, 2012, Notice of Allowance.
U.S. Appl. No. 12/338,977, Jan. 19, 2012, Office Action.
U.S. Appl. No. 12/338,977, Jul. 11, 2012, Office Action.
U.S. Appl. No. 12/338,977, Nov. 28, 2012, Office Action.
U.S. Appl. No. 12/338,977, Jun. 19, 2013, Office Action.
U.S. Appl. No. 12/393,877, Sep. 29, 2011, Office Action.
U.S. Appl. No. 12/393,877, Dec. 13, 2011, Office Action.
U.S. Appl. No. 12/393,877, May 21, 2012, Office Action.
U.S. Appl. No. 12/393,877, Aug. 4, 2014, Notice of Allowance.
U.S. Appl. No. 12/402,398, Mar. 9, 2010, Office Action.
U.S. Appl. No. 12/402,398, May 20, 2010, Office Action.
U.S. Appl. No. 12/402,398, Jan. 24, 2011, Office Action.
U.S. Appl. No. 12/402,398, Sep. 20, 2012, Office Action.
U.S. Appl. No. 12/402,398, Mar. 13, 2013, Notice of Allowance.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,277, Jul. 8, 2010, Office Action.
U.S. Appl. No. 12/403,277, Oct. 12, 2010, Office Action.
U.S. Appl. No. 12/403,277, Mar. 31, 2011, Office Action.
U.S. Appl. No. 12/403,277, Apr. 3, 2012, Office Action.
U.S. Appl. No. 12/403,277, Nov. 5, 2012, Office Action.
U.S. Appl. No. 12/403,277, Jan. 27, 2014, Office Action.
U.S. Appl. No. 12/403,277, Aug. 15, 2014, Office Action.
U.S. Appl. No. 12/481,377, Apr. 28, 2011, Office Action.
U.S. Appl. No. 12/481,377, Jun. 21, 2011, Office Action.
U.S. Appl. No. 12/481,377, Jan. 3, 2012, Office Action.
U.S. Appl. No. 12/481,377, Aug. 10, 2012, Notice of Allowance.
U.S. Appl. No. 12/548,274, Dec. 28, 2011, Office Action.
U.S. Appl. No. 12/548,274, Mar. 2, 2012, Office Action.
U.S. Appl. No. 12/548,274, Sep. 10, 2012, Office Action.
U.S. Appl. No. 12/548,274, Aug. 14, 2014, Office Action.
U.S. Appl. No. 12/608,769, Feb. 10, 2012, Office Action.
U.S. Appl. No. 12/608,769, Aug. 22, 2012, Office Action.
U.S. Appl. No. 12/608,769, Nov. 5, 2012, Notice of Allowance.
U.S. Appl. No. 12/608,773, Jun. 7, 2012, Office Action.
U.S. Appl. No. 12/608,773, Jul. 20, 2012, Office Action.
U.S. Appl. No. 12/608,773, Jan. 7, 2013, Office Action.
U.S. Appl. No. 12/608,773, Jul. 17, 2014, Office Action.
U.S. Appl. No. 12/608,773, Mar. 12, 2015, Office Action.
U.S. Appl. No. 12/608,773, Sep. 17, 2015, Notice of Allowance.
U.S. Appl. No. 12/642,319, Feb. 27, 2012, Office Action.
U.S. Appl. No. 12/642,319, Aug. 28, 2012, Office Action.
U.S. Appl. No. 12/642,319, Dec. 16, 2013, Office Action.
U.S. Appl. No. 12/642,319, May 27, 2014, Notice of Allowance.
U.S. Appl. No. 12/684,400, Feb. 13, 2012, Office Action.
U.S. Appl. No. 12/684,400, May 9, 2012, Office Action.
U.S. Appl. No. 12/684,400, Oct. 16, 2012, Office Action.
U.S. Appl. No. 12/684,400, Feb. 23, 2015, Office Action.
U.S. Appl. No. 12/684,400, Jul. 28, 2015, Notice of Allowance.

(56) References Cited

OTHER PUBLICATIONS

U.S. Appl. No. 12/684,470, Dec. 20, 2011, Office Action.
U.S. Appl. No. 12/684,470, Mar. 23, 2012, Office Action.
U.S. Appl. No. 12/684,470, Aug. 30, 2012, Office Action.
U.S. Appl. No. 12/684,470, Jun. 4, 2014, Office Action.
U.S. Appl. No. 12/684,470, Nov. 14, 2014, Office Action.
U.S. Appl. No. 12/684,470, Aug. 26, 2015, Office Action.
U.S. Appl. No. 12/684,542, Jan. 30, 2012, Office Action.
U.S. Appl. No. 12/684,542, Apr. 16, 2012, Office Action.
U.S. Appl. No. 12/684,542, Sep. 13, 2012, Office Action.
U.S. Appl. No. 12/684,542, Jun. 18, 2014, Office Action.
U.S. Appl. No. 12/684,542, Dec. 1, 2014, Office Action.
U.S. Appl. No. 12/684562 Dec. 28, 2011 Office Action.
U.S. Appl. No. 12/684562 Feb. 16, 2012 Office Action.
U.S. Appl. No. 12/684,562, Aug. 21, 2012, Office Action.
U.S. Appl. No. 12/684,562, Sep. 10, 2014, Office Action.
U.S. Appl. No. 12/684,562, Feb. 17, 2015, Notice of Allowance.
U.S. Appl. No. 12/684,569, Dec. 20, 2011, Office Action.
U.S. Appl. No. 12/684,569, Jan. 27, 2012, Office Action.
U.S. Appl. No. 12/684,569, Jul. 30, 2012, Office Action.
U.S. Appl. No. 12/684,569, Apr. 23, 2014, Office Action.
U.S. Appl. No. 12/688,065, Mar. 13, 2012, Office Action.
U.S. Appl. No. 12/688,065, Apr. 26, 2012, Office Action.
U.S. Appl. No. 12/688,065, Oct. 12, 2012, Office Action.
U.S. Appl. No. 12/688,065, Oct. 18, 2013, Office Action.
U.S. Appl. No. 12/688,065, Apr. 8, 2014, Office Action.
U.S. Appl. No. 12/724,304, Feb. 10, 2012, Office Action.
U.S. Appl. No. 12/848,642, Sep. 20, 2012, Office Action.
U.S. Appl. No. 12/848,642, Nov. 9, 2012, Office Action.
U.S. Appl. No. 12/848,642, Apr. 26, 2013, Office Action.
U.S. Appl. No. 12/848,642, Feb. 3, 2014, Notice of Allowance.
U.S. Appl. No. 12/850,242, Aug. 6, 2012, Office Action.
U.S. Appl. No. 12/850,242, Oct. 17, 2012, Office Action.
U.S. Appl. No. 12/850,242, Apr. 18, 2013, Office Action.
U.S. Appl. No. 12/850,242, Aug. 6, 2013, Notice of Allowance.
U.S. Appl. No. 12/897,358, Aug. 22, 2011, Office Action.
U.S. Appl. No. 12/897,358, Jan. 12, 2012, Notice of Allowance.
U.S. Appl. No. 12/897,358, Mar. 5, 2012, Notice of Allowance.
U.S. Appl. No. 12/941,809, Dec. 13, 2011, Office Action.
U.S. Appl. No. 12/941,809, Jan. 30, 2012, Office Action.
U.S. Appl. No. 12/941,809, Jun. 1, 2012, Office Action.
U.S. Appl. No. 12/941,809, Jul. 3, 2013, Office Action.
U.S. Appl. No. 12/941,809, Nov. 8, 2013, Office Action.
U.S. Appl. No. 12/941,809, Feb. 3, 2014, Notice of Allowance.
U.S. Appl. No. 12/945,646, Jan. 20, 2011, Office Action.
U.S. Appl. No. 12/945,646, Jul. 6, 2011, Office Action.
U.S. Appl. No. 12/945,646, Oct. 26, 2011, Office Action.
U.S. Appl. No. 12/945,646, Feb. 21, 2012, Notice of Allowance.
U.S. Appl. No. 12/950,628, Apr. 25, 2014, Notice of Allowance.
U.S. Appl. No. 12/955,859, May 26, 2011, Office Action.
U.S. Appl. No. 12/955,859, Jul. 21, 2011, Office Action.
U.S. Appl. No. 12/955,859, Dec. 15, 2011, Office Action.
U.S. Appl. No. 12/955,859, Aug. 6, 2012, Office Action.
U.S. Appl. No. 12/955,859, May 16, 2013, Office Action.
U.S. Appl. No. 12/955,859, Aug. 1, 2013, Notice of Allowance.
U.S. Appl. No. 12/961,331, Dec. 4, 2012, Office Action.
U.S. Appl. No. 12/961,331, Feb. 1, 2013, Office Action.
U.S. Appl. No. 12/961,331, Jul. 3, 2013, Office Action.
U.S. Appl. No. 12/961,331, Sep. 20, 2013, Advisory Action.
U.S. Appl. No. 12/961,331, Apr. 25, 2014, Notice of Allowance.
U.S. Appl. No. 12/966,923, Feb. 3, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 12/987,792, Sep. 17, 2012, Office Action.
U.S. Appl. No. 12/987,792, Jan. 21, 2014, Office Action.
U.S. Appl. No. 12/987,792, Jun. 11, 2014, Office Action.
U.S. Appl. No. 12/987,792, Aug. 25, 2014, Notice of Allowance.
U.S. Appl. No. 13/026,989, Sep. 16, 2011, Office Action.
U.S. Appl. No. 13/026,989, Jun. 8, 2012, Office Action.
U.S. Appl. No. 13/026,989, Aug. 23, 2013, Office Action.
U.S. Appl. No. 13/028,041, Jan. 4, 2013, Office Action.
U.S. Appl. No. 13/028,041, Feb. 26, 2013, Office Action.
U.S. Appl. No. 13/028,041, Aug. 21, 2013, Notice of Allowance.
U.S. Appl. No. 13/030,922, Dec. 18, 2012, Office Action.
U.S. Appl. No. 13/030,922, Jan. 31, 2013, Office Action.
U.S. Appl. No. 13/030,922, Jul. 18, 2013, Office Action.
U.S. Appl. No. 13/030,922, Jan. 8, 2014, Notice of Allowance.
U.S. Appl. No. 13/039,087, Jul. 17, 2012, Office Action.
U.S. Appl. No. 13/039,087, Nov. 6, 2012, Notice of Allowance.
U.S. Appl. No. 13/112,618, Mar. 29, 2013, Office Action.
U.S. Appl. No. 13/112,618, Jun. 7, 2013, Office Action.
U.S. Appl. No. 13/112,618, Nov. 20, 2013, Office Action.
U.S. Appl. No. 13/112,618, Dec. 15, 2014, Office Action.
U.S. Appl. No. 13/112,618, May 18, 2015, Office Action.
U.S. Appl. No. 13/112,631, Mar. 29, 2013, Office Action.
U.S. Appl. No. 13/112,631, Jun. 26, 2013, Office Action.
U.S. Appl. No. 13/112,631, Dec. 2, 2013, Office Action.
U.S. Appl. No. 13/112,631, Nov. 20, 2014, Office Action.
U.S. Appl. No. 13/112,631, Apr. 15, 2015, Office Action.
U.S. Appl. No. 13/153,594, Jan. 29, 2013, Office Action.
U.S. Appl. No. 13/153,594, May 29, 2013, Office Action.
U.S. Appl. No. 13/153,594, Oct. 16, 2013, Notice of Allowance.
U.S. Appl. No. 13/222,899, Jan. 10, 2014, Office Action.
U.S. Appl. No. 13/222,899, Jul. 31, 2014, Office Action.
U.S. Appl. No. 13/222,899, Apr. 1, 2015, Office Action.
U.S. Appl. No. 13/222,899, Aug. 5, 2015, Office Action.
U.S. Appl. No. 13/308,227, Apr. 10, 2013, Office Action.
U.S. Appl. No. 13/308,227, Sep. 11, 2013, Office Action.
U.S. Appl. No. 13/308,227, Jul. 14, 2015, Office Action.
U.S. Appl. No. 13/488,233, Feb. 5, 2013, Notice of Allowance.
U.S. Appl. No. 13/490,143, Jan. 4, 2013, Office Action.
U.S. Appl. No. 13/490,143, Apr. 29, 2013, Notice of Allowance.
U.S. Appl. No. 13/525,839, Apr. 1, 2013, Office Action.
U.S. Appl. No. 13/525,839, Jul. 15, 2013, Notice of Allowance.
U.S. Appl. No. 13/615,547, Jan. 18, 2013, Office Action.
U.S. Appl. No. 13/615,547, Apr. 12, 2013, Notice of Allowance.
U.S. Appl. No. 13/791,829, May 29, 2013, Office Action.
U.S. Appl. No. 13/791,829, Oct. 8, 2013, Notice of Allowance.
U.S. Appl. No. 13/791,846, Jun. 4, 2015, Office Action.
U.S. Appl. No. 13/898,202, Jan. 3, 2014, Office Action.
U.S. Appl. No. 13/898,202, Aug. 21, 2014, Office Action.
U.S. Appl. No. 13/898,202, Feb. 10, 2015, Notice of Allowance.
U.S. Appl. No. 13/908,796, Jul. 21, 2015, Office Action.
U.S. Appl. No. 14/017,039, Jan. 23, 2015, Office Action.
U.S. Appl. No. 14/017,039, Jun. 10, 2015, Office Action.
U.S. Appl. No. 14/023,428, Jul. 27, 2015, Office Action.
U.S. Appl. No. 14/077,007, Jul. 27, 2015, Office Action.
U.S. Appl. No. 14/246,926, Aug. 5, 2015, Office Action.
U.S. Appl. No. 14/246,973, Aug. 3, 2015, Office Action.
U.S. Appl. No. 14/466,576, Jul. 8, 2015, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 09/610,128, filed Jul. 5, 2000, Kerievsky.
U.S. Appl. No. 09/866,551, filed May 25, 2001, Ginn.
U.S. Appl. No. 15/131,786, filed Apr. 18, 2016, Roorda et al.
Carpenter et al, Midterm results of the multicenter trial of the Powerlink bifurcated system for endovascular aortic aneurysm repair, Journal of Vascular Surgery, vol. 40, No. 5, Nov. 2004, p. 849-859.e5.
Eisenack et al, Percutaneous Endovascular Aortic Aneurysm Repair: A Prospective Evaluation of Safety, Efficiency, and Risk Factors, Journal of Endovascular Ther., 2009, vol. 16, p. 708-713.
Greenhalgh et al, Endovascular versus open repair of abdominal aortic aneurysm, The New England journal of medicine, vol. 362, No. 20, 2010, p. 1863-1871.
Grossman, W., Cardiac Catheterization and Angiography, 3rd Ed., Lea & Febiger, Philadelphia, pp. 1-49, 52-247. 1986.
Howell et al, Percutaneous Repair of Abdominal Aortic Aneurysms Using the aneuRx Stent Graft and the Percutaneous Vascular Surgery Device, Catheterization and cardiovascular interventions, vol. 55, No. 3, 2002, p. 281-287.

(56) References Cited

OTHER PUBLICATIONS

Jean-Baptiste et al., Percutaneous closure devices for endovascular' repair of infrarenal abdominal aortic aneurysms: a prospective, non-randomized comparative study, European Journal of Vascular and Endovascular Surgery, vol. 35, No. 4, 2008, p. 422-428.
Krajcer and Gregoric, Totally percutaneous aortic aneurysm repair: methods and outcomes using the fully integrated IntuiTrak endovascular system, The Journal of cardiovascular surgery, vol. 51, No. 4, 2010, p. 493-501.
Lederle et al, Outcomes following endovascular vs open repair of abdominal aortic aneurysm: a randomized trial, Jama, vol. 302, No. 14, 2009, p. 1535-1542.
Lee et al, Total percutaneous access for endovascular aortic aneurysm repair ("Preclose" technique), Journal of vascular surgery, vol. 45, No. 6, 2007, p. 1095-1101.
Malkawi et al, Percutaneous access for endovascular aneurysm repair: a systematic review, European Journal of Vascular and Endovascular Surgery, vol. 39, No. 6, 2010, p. 676-682.
Morasch et al, Percutaneous repair of abdominal aortic aneurysm, Journal of vascular surgery, vol. 40, No. 1, 2004, p. 12-16.
Rachel et al, Percutaneous endovascular abdominal aortic aneurysm repair, Annals of vascular surgery, vol. 16, No. 1, 2002, p. 43-49.
Starnes et al, Totally percutaneous aortic aneurysm repair: experience and prudence, Journal of vascular surgery, vol. 43, No. 2, 2006, p. 270-276.
Teh et al, Use of the percutaneous vascular surgery device for closure of femoral access sites during endovascular aneurysm repair: lessons from our experience, European Journal of Vascular and Endovascular Surgery, vol. 22, No. 5, 2001, p. 418-423.
Torsello et al, Endovascular suture versus cutdown for endovascular aneurysm repair: a prospective randomized pilot study, Journal of vascular surgery, vol. 38, No. 1, 2003, p. 78-82.
Traul et al, Percutaneous endovascular repair of infrarenal abdominal aortic aneurysms: a feasibility study, Journal of vascular surgery, vol. 32, No. 4, 2000, p. 770-776.
Watelet et al, Percutaneous repair of aortic aneurysms: a prospective study of suture-mediated closure devices, European journal of vascular and endovascular surgery, vol. 32, No. 3, 2006, p. 261-265.
U.S. Appl. No. 12/114,091, Apr. 6, 2016, Notice of Allowance.
U.S. Appl. No. 12/684,470, Jan. 21, 2016, Office Action.
U.S. Appl. No. 12/684,470, Apr. 22, 2016, Notice of Allowance.
U.S. Appl. No. 13/112,618, Jan. 29, 2016, Office Action.
U.S. Appl. No. 13/112,618, Jul. 6, 2016, Notice of Allowance.
U.S. Appl. No. 13/222,899, Jan. 7, 2016, Notice of Allowance.
U.S. Appl. No. 13/308,227, Feb. 1, 2016, Notice of Allowance.
U.S. Appl. No. 13/725,589, Sep. 17, 2015, Office Action.
U.S. Appl. No. 13/725,589, Mar. 18, 2016, Notice of Allowance.
U.S. Appl. No. 13/791,846, Oct. 27, 2015, Notice of Allowance.
U.S. Appl. No. 13/837,801, Dec. 16, 2015, Office Action.
U.S. Appl. No. 13/837,801, Jun. 9, 2016, Office Action.
U.S. Appl. No. 13/837,801, Feb. 9, 2017, Office Action.
U.S. Appl. No. 13/837,801, Jul. 6, 2017, Office Action.
U.S. Appl. No. 13/908,796, Nov. 6, 2015, Notice of Allowance.
U.S. Appl. No. 14/017,039, Oct. 27, 2015, Office Action.
U.S. Appl. No. 14/017,039, Apr. 4, 2016, Notice of Allowance.
U.S. Appl. No. 14/023,428, Feb. 9, 2016, Office Action.
U.S. Appl. No. 14/023,428, Jun. 13, 2016, Office Action.
U.S. Appl. No. 14/023,428, Dec. 20, 2016, Office Action.
U.S. Appl. No. 14/023,428, Jul. 18, 2017, Office Action.
U.S. Appl. No. 14/077,007, Jan. 29, 2016, Office Action.
U.S. Appl. No. 14/077,007, Aug. 12, 2016, Notice of Allowance.
U.S. Appl. No. 14/246,926, Nov. 23, 2015, Office Action.
U.S. Appl. No. 14/246,926, Jun. 15, 2016, Office Action.
U.S. Appl. No. 14/246,926, Oct. 3, 2016, Notice of Allowance.
U.S. Appl. No. 14/246,973, Nov. 24, 2015, Office Action.
U.S. Appl. No. 14/246,973, Jul. 7, 2016, Office Action.
U.S. Appl. No. 14/246,973, Nov. 9, 2016, Notice of Allowance.
U.S. Appl. No. 14/312,339, Jan. 22, 2016, Office Action.
U.S. Appl. No. 14/312,339, May 3, 2016, Office Action.
U.S. Appl. No. 14/312,339, Jan. 31, 2017, Office Action.
U.S. Appl. No. 14/312,339, May 23, 2017, Office Action.
U.S. Appl. No. 14/312,339, Aug. 28, 2017, Office Action.
U.S. Appl. No. 14/323,753, Nov. 3, 2015, Office Action.
U.S. Appl. No. 14/323,753, Apr. 15, 2016, Notice of Allowance.
U.S. Appl. No. 14/466,576, Dec. 15, 2015, Notice of Allowance.
U.S. Appl. No. 14/539,830, Jan. 29, 2016, Office Action.
U.S. Appl. No. 14/539,830, Jul. 26, 2016, Office Action.
U.S. Appl. No. 14/539,830, Nov. 18, 2016, Notice of Allowance.
U.S. Appl. No. 14/839,658, May 30, 2017, Office Action.
U.S. Appl. No. 14/839,658, Sep. 19, 2017, Office Action.
U.S. Appl. No. 15/149,784, May 11, 2017, Office Action.
U.S. Appl. No. 15/222,397, Jan. 23, 2017, Office Action.
U.S. Appl. No. 14/928,950, Sep. 26, 2017, Office Action.
U.S. Appl. No. 14/023,428, dated Jan. 4, 2018, Notice of Allowance.
U.S. Appl. No. 14/312,339, dated Dec. 28, 2017, Office Action.
U.S. Appl. No. 14/839,658, dated Feb. 28, 2018, Notice of Allowance.
U.S. Appl. No. 14/855,080, dated Apr. 2, 2018, Office Action.
U.S. Appl. No. 14/928,950, dated Mar. 30, 2018, Office Action.
U.S. Appl. No. 15/056,281, dated Feb. 5, 2018, Office Action.
U.S. Appl. No. 15/069,230, dated Feb. 15, 2018, Office Action.
U.S. Appl. No. 15/356,028, dated Feb. 22, 2018, Office Action.

\* cited by examiner

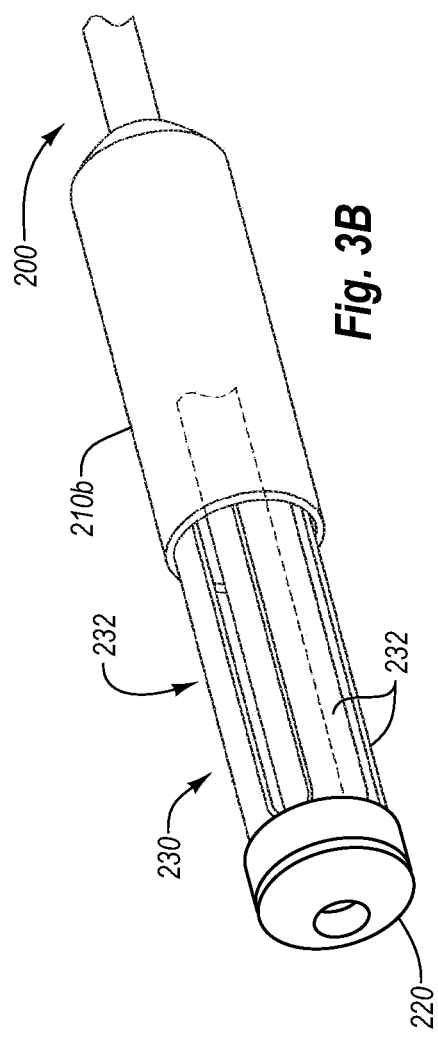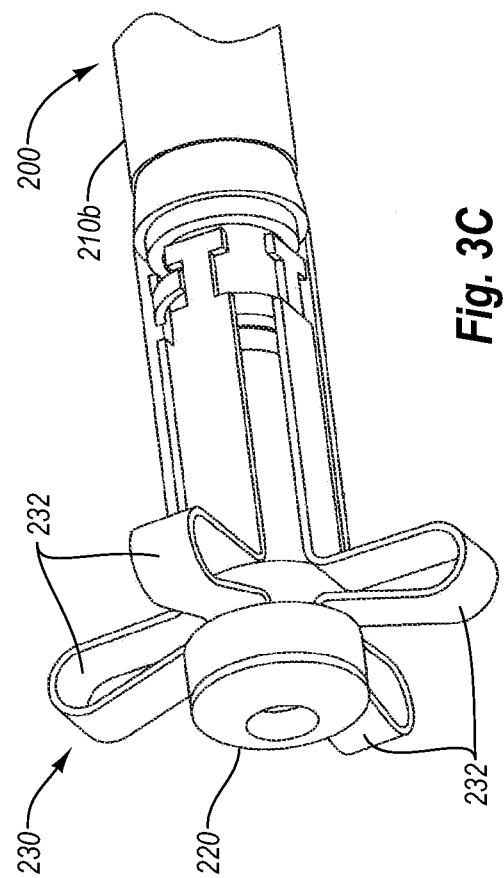
Fig. 3B
Fig. 3C

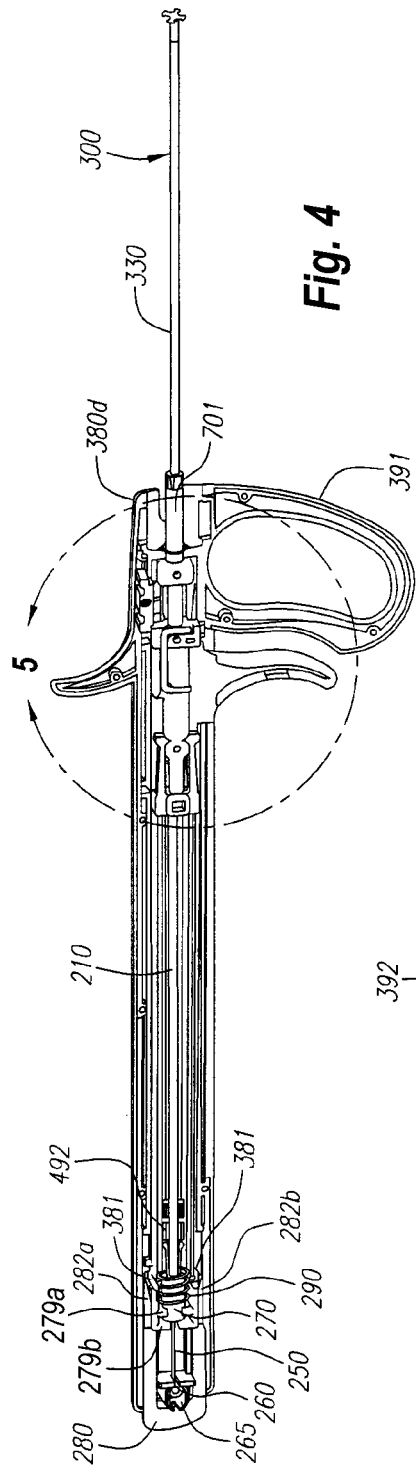
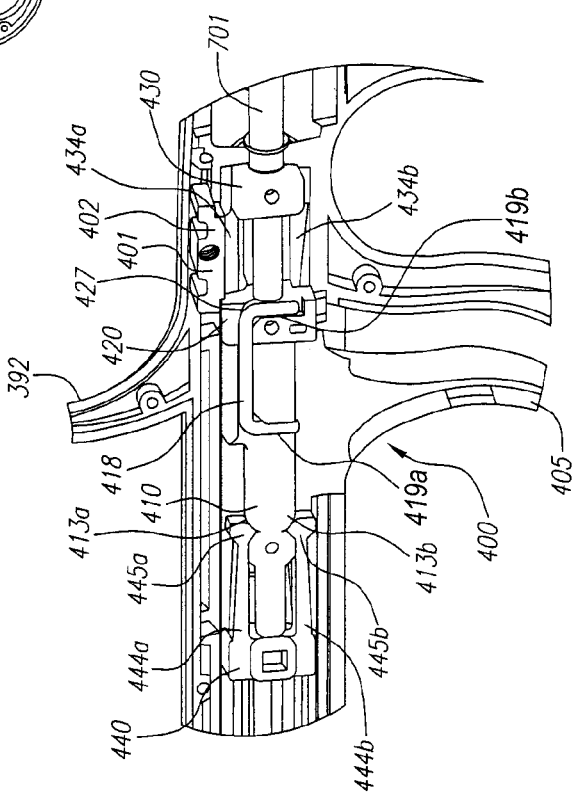
Fig. 4
Fig. 5

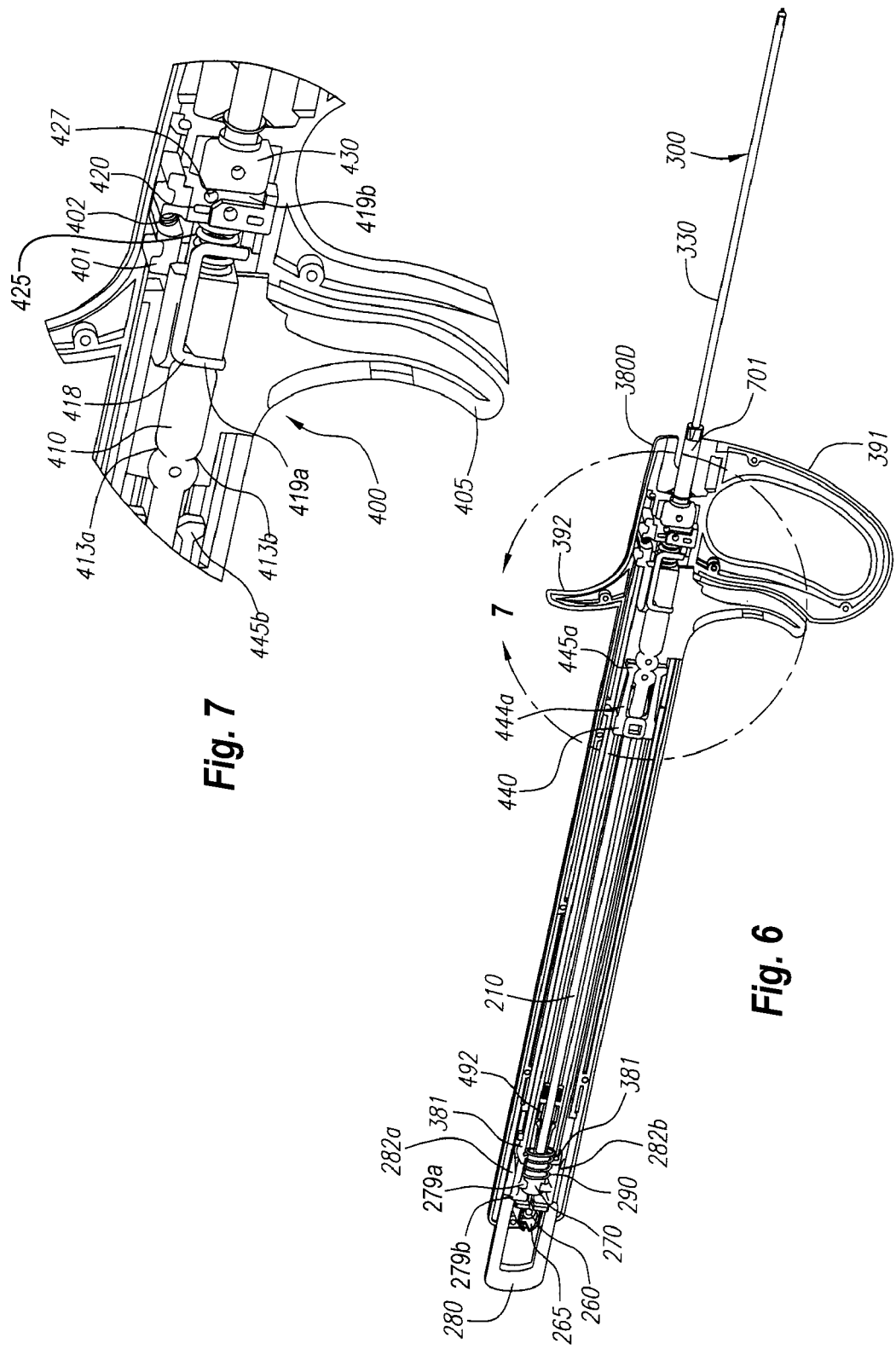

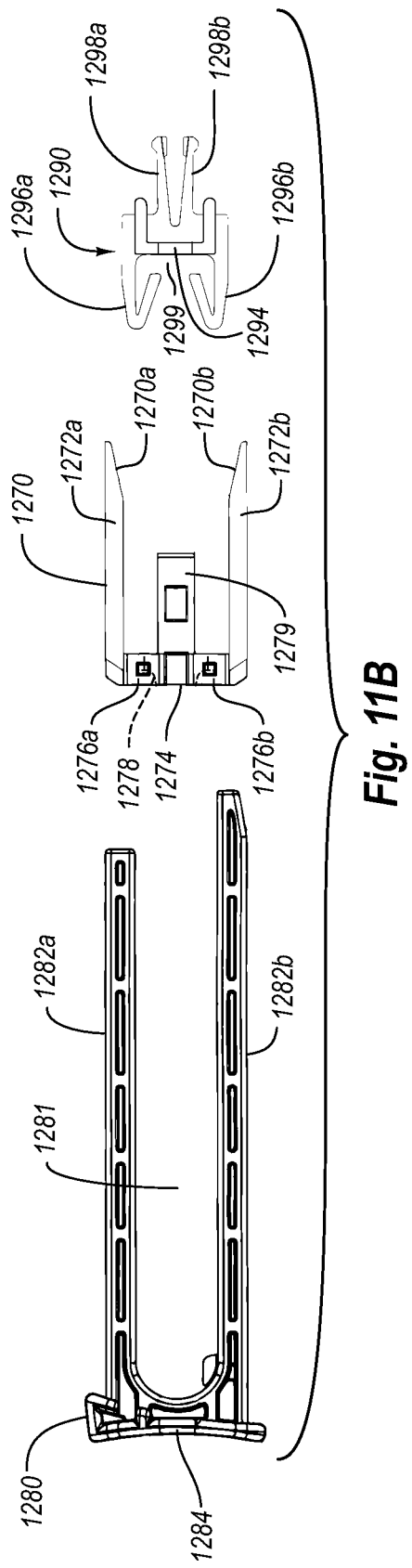
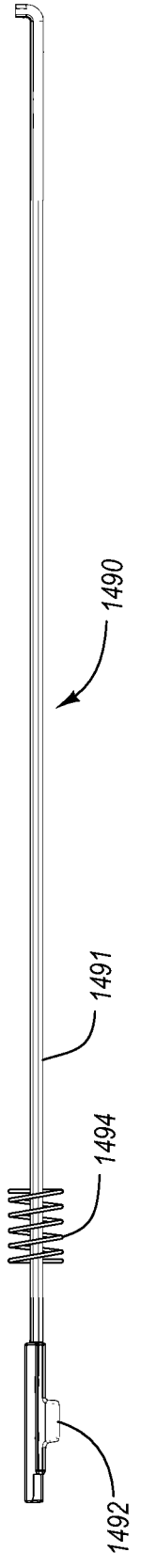
Fig. 11B
Fig. 11C

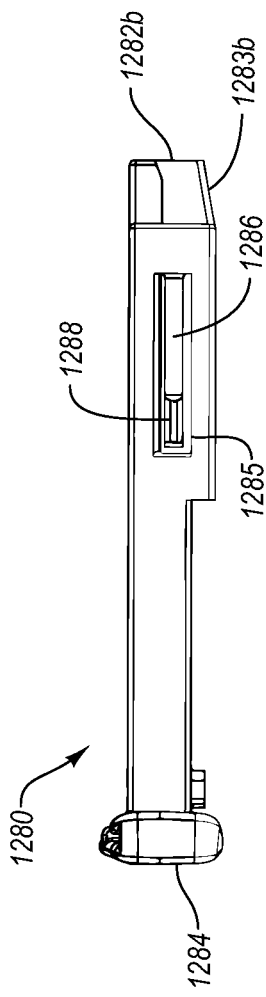
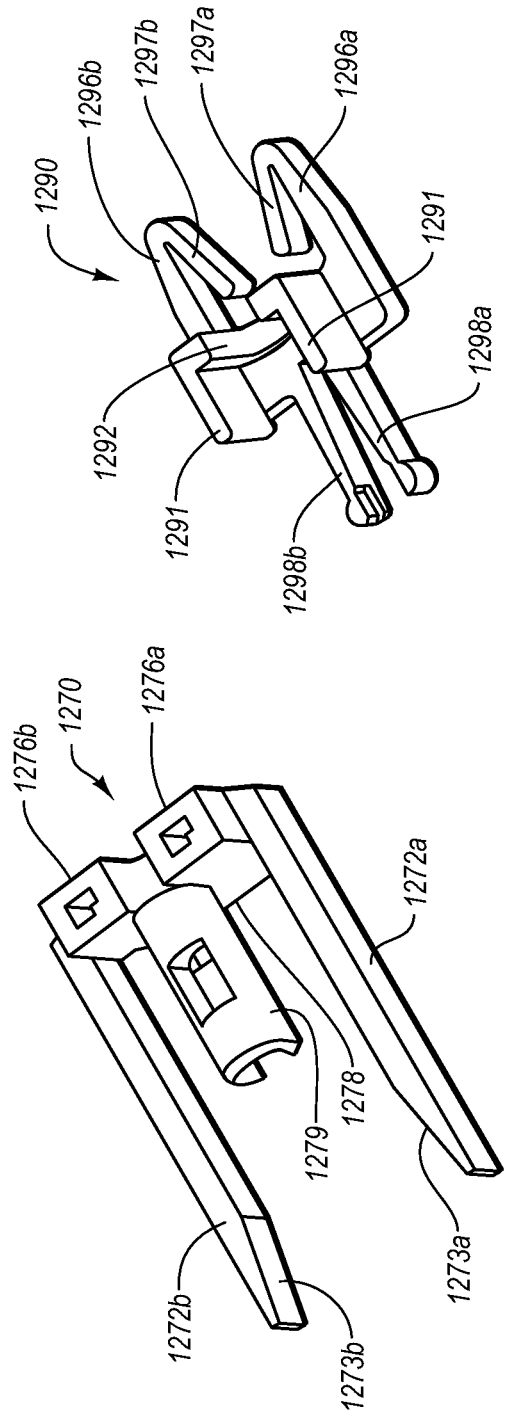
Fig. 11D
Fig. 11E
Fig. 11F

CLIP APPLIER AND METHODS OF USE

CROSS-REFERENCE TO RELATED APPLICATIONS

This is a continuation of U.S. patent application Ser. No. 13/898,202, filed May 20, 2013, and entitled CLIP APPLIER AND METHODS OF USE, which is a continuation of U.S. patent application Ser. No. 13/615,547, filed Sep. 13, 2012, and entitled CLIP APPLIER AND METHODS OF USE, now U.S. Pat. No. 8,518,057, which is a continuation of U.S. patent application Ser. No. 11/427,297, filed Jun. 28, 2006, and entitled CLIP APPLIER AND METHODS OF USE, now U.S. Pat. No. 8,313,497, which claims priority to and the benefit of U.S. Provisional Patent Application Ser. No. 60/696,069, filed Jul. 1, 2005, and entitled CLIP APPLIER AND METHODS OF USE, each of which is incorporated herein by reference in its entirety. This application also incorporates by reference U.S. patent application Ser. No. 10/356,214 and U.S. patent application Ser. No. 10/638,115 in their entireties.

FIELD OF THE INVENTION

The present invention relates generally to apparatus and methods for closing and/or sealing openings through tissue, and more particularly to apparatus and methods for delivering a closure element for closing a puncture in a blood vessel or other body lumen formed during a diagnostic or therapeutic procedure.

BACKGROUND OF THE INVENTION

Catheterization and interventional procedures, such as angioplasty or stenting, generally are performed by inserting a hollow needle through a patient's skin and tissue into the vascular system. A guide wire may be advanced through the needle and into the patients blood vessel accessed by the needle. The needle is then removed, enabling an introducer sheath to be advanced over the guide wire into the vessel, e.g., in conjunction with or subsequent to a dilator.

A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath would be removed, leaving a puncture site in the vessel wall. Traditionally, external pressure would be applied to the puncture site until clotting and wound sealing occur, however, the patient must remain bedridden for a substantial period of time after clotting to ensure closure of the wound. This procedure, however, may be time consuming and expensive, requiring as much as an hour of a physicians or nurses time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. Another technique has been suggested that involves percutaneously suturing the puncture site, such as that disclosed in U.S. Pat. No. 5,304,184, issued to Hathaway et al.

To facilitate positioning devices that are percutaneously inserted into a blood vessel, "bleed back" indicators have been suggested. For example, U.S. Pat. No. 5,676,974, issued to Kensey et al., discloses a bleed back lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel.

Accordingly, apparatus and methods for delivering a device for closing a vascular puncture site or other opening through tissue would be useful.

BRIEF SUMMARY

The present invention is directed toward an apparatus and method for delivering a closure element through tissue and into an opening formed in, or adjacent to, a wall of a blood vessel or other body lumen of any size. The apparatus can be configured to receive and retain the closure element so that the closure element can be disposed substantially within the apparatus. Thereby, when the apparatus is introduced via an introducer sheath, for example, the closure element can be disposed within and delivered by way of a lumen of the introducer sheath. The apparatus can also be configured to engage the blood vessel wall adjacent to the opening and to position the closure element substantially adjacent to an outer surface of the blood vessel wall adjacent to the opening.

When properly positioned, the apparatus can be activated to distally deploy the closure element. During deployment, the apparatus can be configured to substantially uniformly expand the closure element beyond a natural cross-section of the closure element such that the closure element, when deployed, can be configured to engage the blood vessel wall and/or tissue. Engaging the blood vessel wall and/or tissue, the closure element can be further configured to return to the natural cross-section. Thereby, the engaged blood vessel wall and/or tissue are drawn substantially closed and/or sealed, such that, for example, hemostasis within the opening can be enhanced.

The present invention can also accommodate for variations in the size of the physicians hand and grip by selectively reducing the distance between the devices handle portion and a portion of a triggering system usable to deploy the closure element. The triggering system of the apparatus can at least partially move a trigger extension graspable by a physician or clinician as a locator assembly locates the blood vessel wall prior to deploying the closure element. This partial movement reduces the gap between the trigger extension and the handle portion. In this manner, a physician or clinician does not need to stretch uncomfortably to position a thumb or finger on the trigger extension, grasping the handle portion, and maintaining the device in the desired orientation relative to the tissue and/or the puncture site.

An apparatus of the present invention is usable to deliver a closure element to an opening formed in a wall of a body lumen. The apparatus can include a locator assembly having a distal end region configured to extend into the opening and selectably contact the wall of the body lumen and a proximal end configured to cooperate with a movable plunger. A carrier assembly can be coupled with the locating assembly, the carrier assembly retaining the closure element in a substantially tubular configuration within the carrier assembly. A triggering system can also cooperate with the locator assembly, the triggering system can move toward the distal end region of the locator assembly as the movable plunger moves toward the distal end region. In one configuration, the triggering system can move toward the distal end region substantially simultaneously with the distal end region transitioning from the unexpanded state to the expanded state.

The locator assembly of the apparatus can further include a locator control system coupled to a proximal end region of the locator assembly. This locator control system can be configured to selectively control the distal end region of the locator assembly between the expanded state and the unexpanded state. In one configuration, the locator control system can include a tubular body block mounted to a tubular member, a spring retainer receiving a portion of the tubular body block, and a movable plunger slidably cooperating with the tubular body block and the tubular member.

The present invention can also provide a stable base upon which the physician or clinician can move the device or apparatus as the closure element is positioned and deployed. In one configuration, the stable base is formed from the handle portion having two graspable portions: a shaped grasping portion and an elongated grasping portion. The shaped grasping portion can be configured to receive at least a thumb or finger of the physician. A portion of the handle portion can have a curved profile to enable a portion of the handle to fit comfortably within a user's hand while the hand is rested on a patient during the procedure to provide stability during use of the device and function as a based or pivot point for moving the remainder of the device or apparatus.

Other aspects and features of the present invention will become apparent from consideration of the following description in conjunction with the accompanying drawings.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

FIG. 3B illustrates a close-up view of the distal end of the apparatus shown in FIG. 2 in an unexpanded state.

FIG. 3C illustrates a close-up view of the distal end of the apparatus shown in FIG. 2 in an expanded state.

FIG. 4 illustrates the apparatus of FIG. 2 after distal advancement of the locator assembly, the triggering system and the carrier assembly.

FIG. 5 illustrates a close-up view of the triggering system and carrier assembly of the apparatus shown in FIG. 4.

FIG. 6 illustrates the apparatus of FIG. 1A-1B after the clip has been released to close the opening in the tissue.

FIG. 7 illustrates a close-up view of the triggering system and carrier assembly of the apparatus of FIG. 1A-1B after the clip has been released to close the opening in the tissue.

FIG. 11B illustrates a portion of a locator control system of the alternative embodiment of FIG. 9.

FIG. 11C illustrates a portion of a locator release system of the alternative embodiment of FIG. 9.

FIG. 11D illustrates a side view of a plunger of the locator control system of FIG. 11B of the alternative embodiment of FIG. 9.

FIG. 11E illustrates a perspective view of a tubular body block of the locator control system of FIG. 11B of the alternative embodiment of FIG. 9.

FIG. 11F illustrates a perspective view of a spring retainer of the locator control system of FIG. 11B of the alternative embodiment of FIG. 9.

Figure 1A:
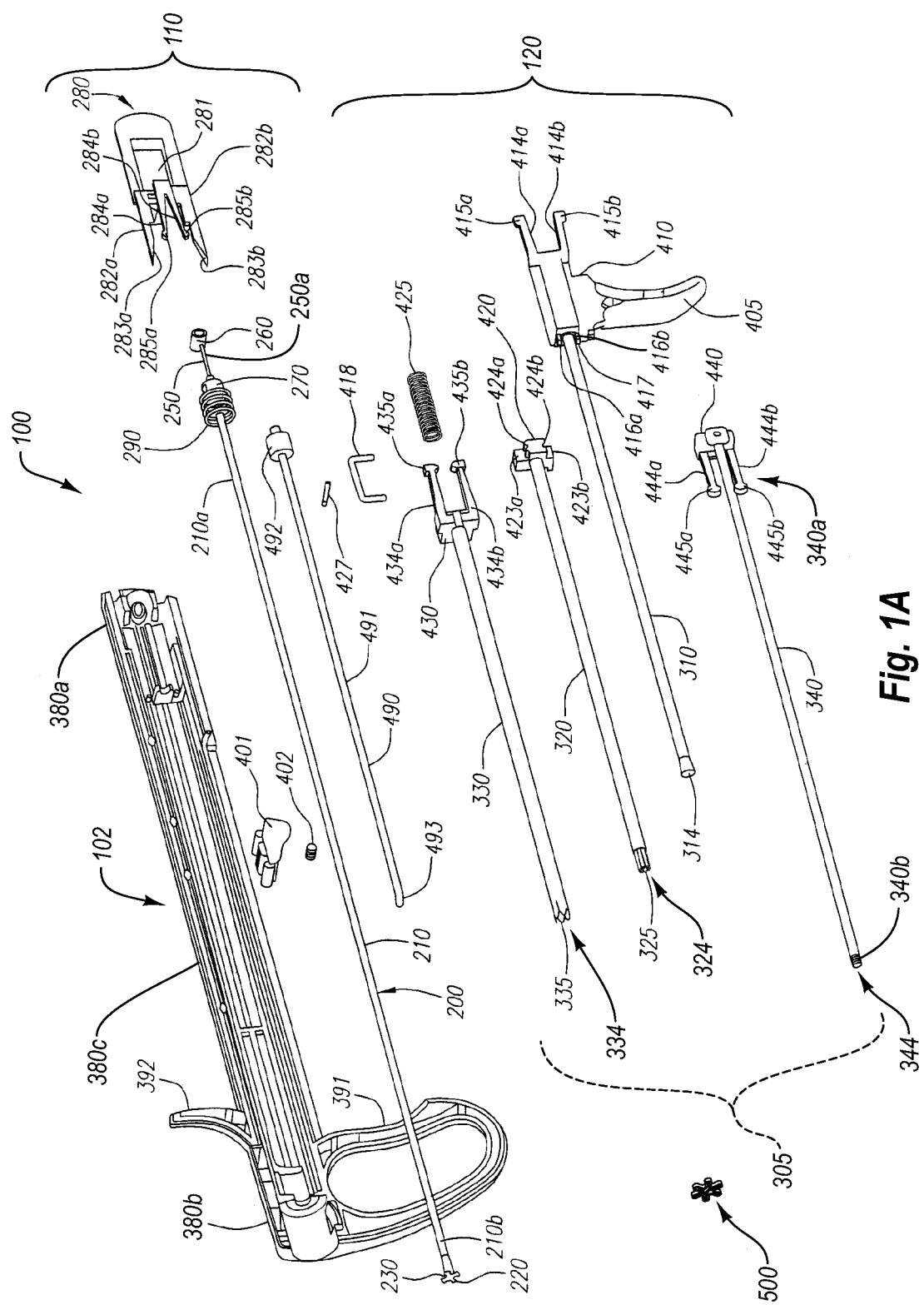
FIG. 1A illustrates an assembly view of the components of one embodiment according to the present invention for closing openings in blood vessel walls.

It should be noted that the figures are not drawn to scale and that elements of similar structures or functions are generally represented by like reference numerals for illustrative purposes throughout the figures. It also should be noted that the figures are only intended to facilitate the description of embodiments of the present invention.

DETAILED DESCRIPTION

The embodiments described herein extend to methods, systems, and apparatus for closing and/or sealing openings in a blood vessel or other body lumen formed during a diagnostic or therapeutic procedure. The apparatuses of the present invention are configured to deliver a closure element through tissue and into an opening formed in and/or adjacent to a wall of a blood vessel or other body lumen.

Since current apparatuses for sealing openings formed in blood vessel walls can snag tissue adjacent to the openings during positioning and may not provide an adequate seal, an apparatus that is configured to prevent inadvertent tissue contact during positioning and to engage tissue adjacent to the opening can prove much more desirable and provide a basis for a wide range of medical applications, such as diagnostic and/or therapeutic procedures involving blood vessels or other body lumens of any size. Further, since current apparatuses for sealing openings formed in blood vessel walls are typically one-size and do not provide a mechanism to accommodate for variations in the size or configuration of the physician or clinicians hands, an apparatus that varies its operational configuration to accommodate for physician or clinician hand sizes can prove much more desirable and beneficial to the medical arts. These results, whether individually or collectively, can be achieved, according to one embodiment of the present invention, by employing an apparatus as shown in the figures and described in detail below.

As will be discussed in more detail below, the apparatuses of the present invention are configured to deliver a closure element through tissue and into an opening formed in and/or adjacent to a wall of a blood vessel or other body lumen. The apparatus can be configured to receive and retain a closure element such that the closure element can be disposed substantially within the apparatus. The apparatuses in accordance with the present invention generally include a handle portion having a proximal end and a distal end, a locator and clip delivery assembly extending from the distal end of the handle portion, and a locator actuator disposed at the proximal end of the handle portion.

Referring now to FIG. 1, an exploded assembly view of one closure apparatus is shown in accordance with the present invention. As shown in FIG. 1, the apparatus can include a housing that receives or retains a plurality of tubular members. The tubular members can be concentrically disposed within the housing of the device, with each tubular member having an associated block member fixedly attached to the proximal end thereof. The block members can be configured to interact with each other as well as with features of the housing, such as through movement of a triggering system. The interaction of the tubular members, the blocks, and the triggering system will be described in greater detail below. Also described below will be additional details regarding the handle portion of the housing and the manner by which the movement of the tubular members and the triggering system results in variation of the devices operational configuration to accommodate for physician or clinician hand sizes.

Figure 1B:
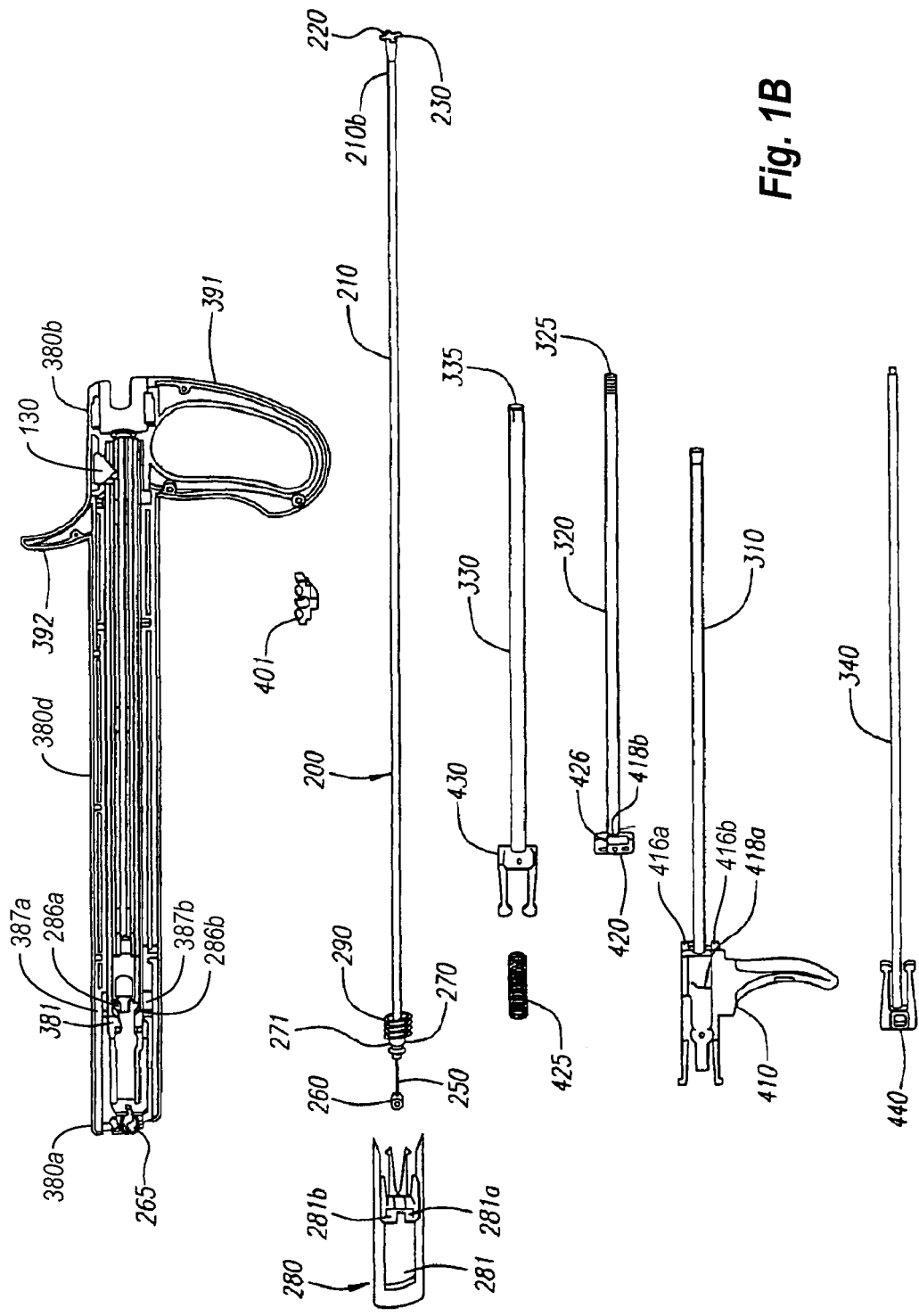
FIG. 1B illustrates another assembly view of the components of one embodiment according to the present invention for closing openings in blood vessel walls.

With continued reference to FIGS. 1A and 1B, apparatus 100 can be provided as one or more integrated components and/or discrete components that may be retained within a housing 102, having a housing top half 380c and a housing bottom half 380d (not shown). For example, apparatus 100 can include a locator assembly 110 and a carrier assembly 120. For purposes of illustration, locator assembly 110 and carrier assembly 120 are shown in FIG. 1A as comprising substantially separate assemblies. As desired, however, locator assembly 110 and carrier assembly 120 each can be provided, in whole or in part, as one or more integrated assemblies.

Turning to FIGS. 1A-2, 4, and 6, the assembly 110 can include a locator assembly 200. This locator assembly 200 can include flexible or semi-rigid tubular body 210 (such as an elongate rail) with a longitudinal axis. Tubular body 210 can have a proximal end region 210a and a distal end region 210b and can include a predetermined length and a predetermined outer cross-section, both of which can be of any suitable dimension. Distal end region 210b of locator assembly 200, as shown in more detail in FIGS. 3B and 3C, can include a substantially rounded, soft, and/or flexible distal end or tip 220 to facilitate advancement and/or retraction of distal end region 210b into a blood vessel or other opening in tissue. As desired, a pigtail (not shown) may be provided on tip 220 to further aid atraumatic advancement of distal end region 210b.

Distal end region 210b of locator assembly 200 is selectably controllable between an unexpanded state, as shown in FIG. 3B, and an expanded state, as shown in FIG. 3C. As shown in FIG. 3B, when an expansion end 230 is in an unexpanded state, substantially flexible members 232 are substantially axially aligned with locator assembly 200. Alternatively, when expansion end 230 is in an expanded state, substantially flexible members 232 are flexed outward.

Returning to FIG. 1B, a control member 250, such as a rod, wire, or other elongate member, may be moveably disposed within a lumen (not shown) formed by tubular body 210 and extending substantially between the proximal end region 210a and distal end region 210b. Control member 250 may have proximal end region 250a coupled with a control block 260, and a distal end region 250b coupled with distal end region 210b of locator assembly 200, expansion end 230, and/or the movable end regions of substantially flexible members 232. Control block 260 may be formed of a metal or rigid plastic in a tubular shape, and may be adapted to be retained in control block cavity 265 formed on the internal surface of housing bottom half 380d, to thereby maintain control block 260 in a substantially fixed position relative to the housing 380. By moving tubular body 210 axially relative to control member 250, the distal end region 210b, expansion end 230, and/or the substantially flexible members 232 (FIG. 3B), are selectively transitioned between the unexpanded and expanded states.

Figure 3A:
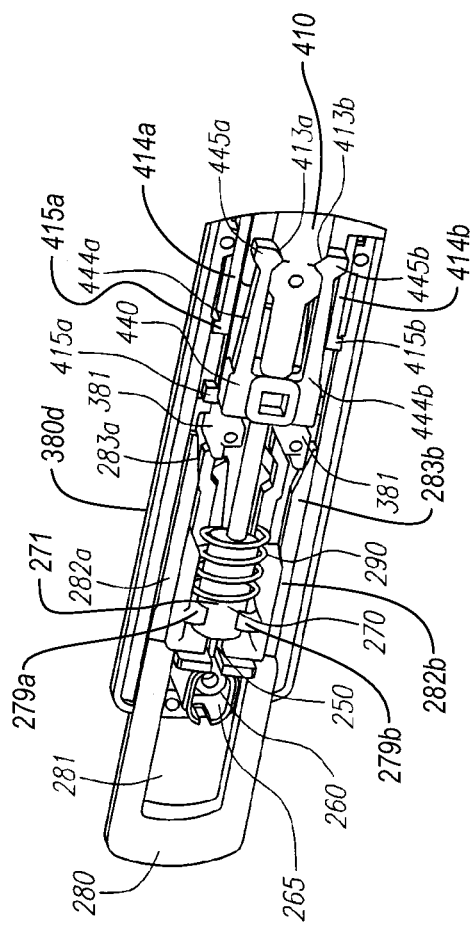
FIG. 3A illustrates a close-up view of the proximal end of the apparatus shown in FIG. 2.

With reference to FIG. 3A, a tubular body block 270 having proximal groove 271 may be formed on proximal end 210a of tubular body 210. Tubular body block 270 may be formed of metal, rigid plastic, or other substantially rigid material and may be formed integrally with or attached securely to tubular body 210. Proximal groove 271 and the proximal end of tubular body block 270 may have a shape adapted to cooperate with a pair of tabs 279a, 279b formed on a locator assembly block 280, whereby tubular body block 270 may be maintained in a fixed axial relationship with the locator assembly block 280. In this way, tubular body block 270 and tubular body 210 (FIG. 1B) may advance distally by distal advancement of locator assembly block 280.

A locator assembly spring 290 may be located coaxially with and may substantially surround a portion of tubular body block 270. Locator assembly spring 290 may be located between and in contact with the distal side of two of tabs 279a, 279b formed on locator assembly block 280 and the proximal side of locator assembly spring stop 381 formed on the inner surface of housing bottom half 380d. The locator assembly spring 290 so located may provide a force biasing to locator assembly block 280 in the proximal direction relative to housing 380.

Locator assembly block 280 may be formed of metal, plastic, or other rigid material. A function of locator assembly block 280 may be to allow a user to apply a force causing distal movement of tubular body 210 (FIG. 1) relative to control member 250 causing locator assembly 200 (FIG. 2) to transition from the unexpanded state to the expanded state. Slot 281 may be formed in the proximal end of locator assembly block 280. Slot 281 may have a size sufficient to accommodate control block 260 and control block cavity 265, and to allow locator assembly block 280 to travel axially relative to housing 380. As shown in FIG. 1, the distal end of locator assembly block 280 may include a pair of distally extending legs 282a-b, with each of legs 282a-b having a ramp 283a-b on its inward facing surface. Finally, the locator assembly block 280 may have a pair of distally extending release tabs 284a-b, each of release tabs 284a-b having a detent 285a-b.

Figure 2:
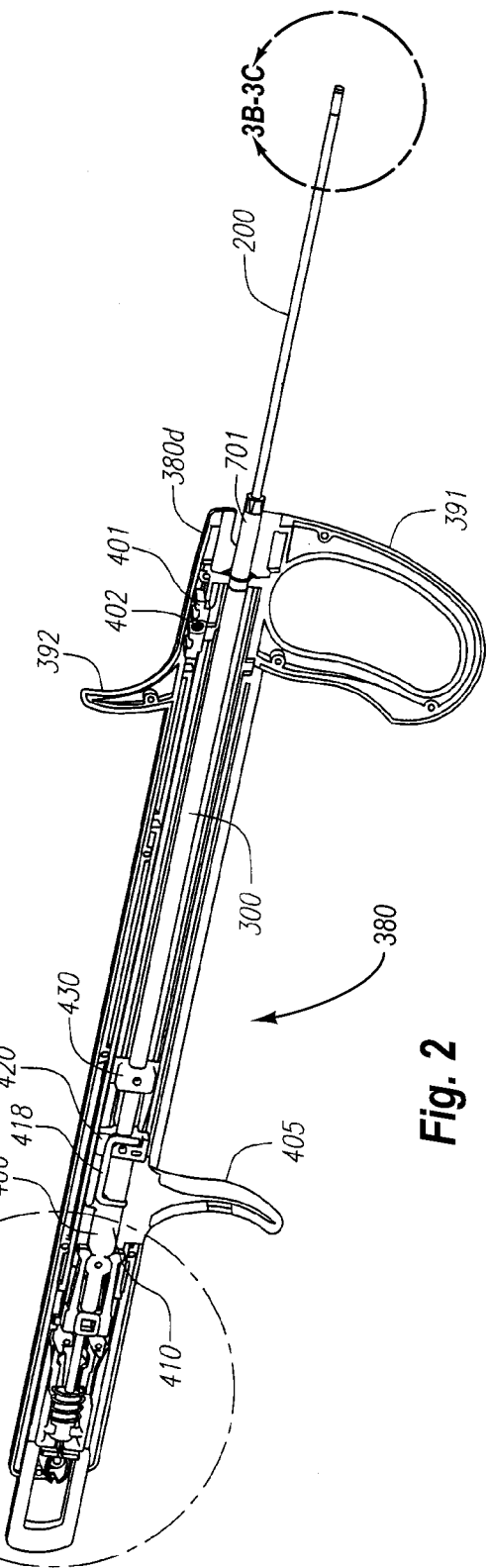
FIG. 2 illustrates the assembled carrier assembly and triggering assembly of the apparatus shown in FIGS. 1A and 1B.

As shown in FIGS. 2-3A, locator assembly block 280 may be slidably received and retained within grooves formed in the proximal end of housing 380, with the proximal end of locator assembly block 280 extending from the proximal end of housing 380. Control block 260 and control block cavity 265 may be located in slot 281 formed in the proximal end of locator assembly block 280.

To release locator assembly 200, and enable it to slidably move within the grooves formed in the proximal end of the housing 380 and allow locator assembly 200 to transition from its expanded state to its unexpanded state, the apparatus 100 can include a locator release system 490 (FIG. 1A). Turning to FIG. 1A, locator release system 490 of the apparatus 100 may include locator release rod 491 having release tab spacer block 492 formed on its proximal end. Locator release rod 491 and release tab spacer block 492 may be received and retained in a groove formed on the interior surface of housing bottom half 380d. Release tab spacer block 492 may be integrally formed with or attached to the proximal end of locator release rod 491 and may be formed of metal, plastic, or other rigid material. Release tab spacer block 492 may have a shape and size adapted to fit between release tabs 284a-b formed on locator assembly block 280, thereby biasing release tabs 284a-b outward and causing outward facing detents 285a-b to engage retaining grooves 286a-b (FIG. 1B) formed on the interior of housing 380. As long as detents 285a-b are thus engaged with retaining grooves 286a-b in housing 380, locator assembly block 280 is held in an axial position against the spring force imparted in the proximal direction by locator assembly spring 290.

With continued reference to FIG. 1A, the distal end of locator release rod 491 may have an engagement member 493 that comprises an inward bend on the distal end of locator release rod 491. As described more fully below, engagement member 493 on locator release rod 491 may be positioned within the apparatus 100 such that when closure element 500 is delivered, engagement member 493 is engaged and caused to move axially in the distal direction, thereby disengaging release tab spacer block 492 from locator assembly block 280 and causing locator assembly 200 simultaneously to transition from an expanded state to an unexpanded state.

Returning to FIG. 1A, the carrier assembly 120 may be coupled with, and slidable relative to, locator assembly 200. Carrier assembly 120 may be configured to receive and retain closure element 500, which may be disposed substantially within carrier assembly 120. Carrier assembly 120 may be further configured to position closure element 500 substantially adjacent to an opening to be closed, and to deploy closure element 500. Upon being deployed, closure element 500 can maintain a reduced cross-section but may also temporarily and substantially uniformly expand beyond the natural cross-section of closure element 500. In either case, closure element 500, when deployed, can engage an amount of the blood vessel wall and/or tissue adjacent to the opening. Thereafter, closure element 500 may be configured to return to the natural cross-section, optionally substantially uniformly, such that the blood vessel wall and/or tissue are drawn substantially closed and/or sealed.

As shown in FIG. 1A, carrier assembly 120 may include a tube set 305 of at least one tubular member. For instance, the illustrated tube set can include carrier member 310, pusher member 320, cover member 330, and support member 340, also shown in FIG. 8. Carrier member 310, pusher member 320, cover member 330, and support member 340 may be provided as a plurality of nested, telescoping members with a common longitudinal axis. Carrier member 310 may be configured to receive and support closure element 500. While being disposed on carrier member 310, closure element 500 may be deformed from the natural, planar configuration to form a substantially tubular closure element 500", as shown in FIGS. 14A-14G, and as described herein.

Returning to FIG. 1A, carrier member 310 may include proximal end region 310a and distal end region 310b. Carrier member 310 may also define lumen 314, which may extend substantially between proximal end region 310a and distal end region 310b and configured to slidably receive at least a portion of tubular body 210 of locator assembly 200 and/or support member 340. Although the exterior cross-section of the carrier member 310 may be substantially uniform, the distal end region 310b of carrier member 310 may have a cross-section that increases distally, as illustrated in FIG. 1A, for substantially uniformly expanding substantially tubular closure element 500 (FIG. 14G) beyond natural cross-section 530 (FIG. 14A) of closure element 500" when substantially tubular closure element 500" is deployed. Alternatively, distal end region 310b may be formed with a uniform cross-section to deploy closure element 500 without cross-sectional expansion.

Pusher member 320 may have proximal end region 320a and distal end region 320b. Pusher member 320 may be coupled with, and slidable relative to, carrier member 310. Pusher member 320 may include a predetermined length and a predetermined cross-section, both of which can be of any suitable dimension and can be configured to slidably receive carrier member 310 such that distal end region 320b of pusher member 320 may be offset proximally from distal end region 310b of carrier member 310. As desired, the predetermined length of pusher member 320 may be substantially equal to a predetermined length of carrier member 310. A predetermined length of pusher member 320 may be less than a predetermined length of carrier member 310 such that carrier member 310 and pusher member 320 may at least partially define a space 360 (FIG. 8) distal to distal end region 320b of pusher member 320 and along the periphery of carrier member 310.

Pusher member 320 may be substantially tubular and can define a lumen 324 that may extend substantially between proximal end region 320a and distal end region 320b and configured to slidably receive at least a portion of the carrier member 310. The cross-section of pusher member 320 may be substantially uniform and distal end region 320b of pusher member 320 can comprise one or more longitudinal extensions 325, which may extend distally from pusher member 320 and along the periphery of carrier member 310. Longitudinal extensions 325 may be biased such that longitudinal extensions 325 extend generally in parallel with the common longitudinal axis of carrier assembly 120. Longitudinal extensions 325 may be sufficiently flexible to expand radially, and yet sufficiently rigid to inhibit buckling as distal end region 320b is directed distally along carrier member 310 and engages the distally-increasing cross-section of distal end region 310b of carrier member 310 to deploy closure element 500

Cover member 330 may be configured to retain closure element 500, in its generally tubular configuration, substantially within the carrier assembly 120 prior to deployment. Being coupled with, and slidable relative to, pusher member 320, cover member 330 has proximal end region 330a and distal end region 330b, a predetermined length and a predetermined cross-section, both of which can be of any suitable dimension. Cover member 330 may be formed as a substantially rigid, semi-rigid, or flexible tubular member with an inner periphery and an outer periphery, and may define a lumen 334. Lumen 334 may extends substantially between proximal and distal end regions 330a, 330b of cover member 330 and may be configured to slidably receive at least a portion of pusher member 320. When cover member 330 is properly positioned within carrier assembly 120, as schematically illustrated in FIG. 15A, distal end region 330b may be configured to extend over the space 360, thereby defining annular cavity 370 for receiving and retaining substantially tubular closure element 500".

Figure 8:
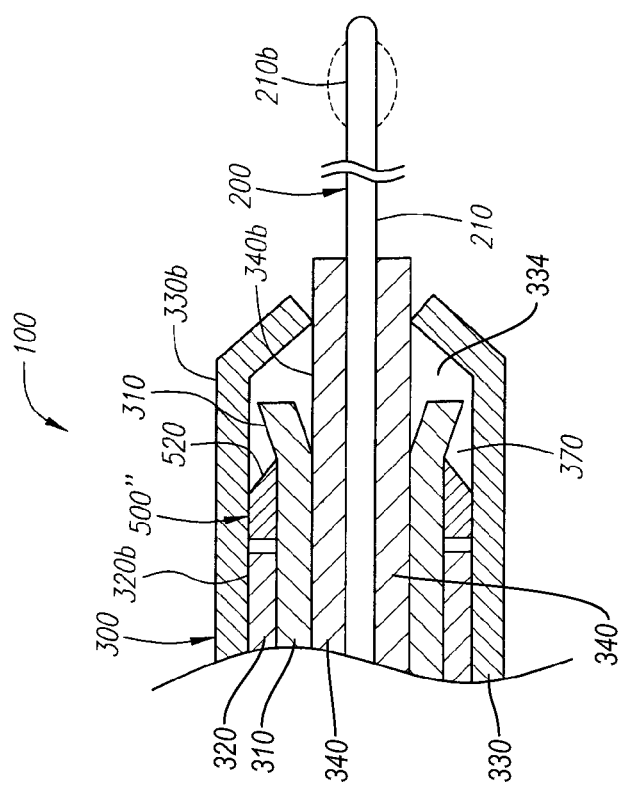
FIG. 8 illustrates a cross-sectional schematic view of the distal end of the apparatus shown in FIG. 4 as assembled for deployment.

The cross-section of cover member 330 may be substantially uniform, and distal end region 330b of cover member 330 may comprise one or more longitudinal extensions 335, which extend distally from cover member 330 and along an outer periphery of pusher member 320, as shown in FIG. 8. Although longitudinal extensions 335 can extend generally in parallel with the longitudinal axis of the tube set 305, longitudinal extensions 335 may be biased such that the plurality of longitudinal extensions 335 extend substantially radially inward. Thereby, longitudinal extensions 335 may at least partially close lumen 334 substantially adjacent to distal end region 330b of cover member 330.

Figure 15A:
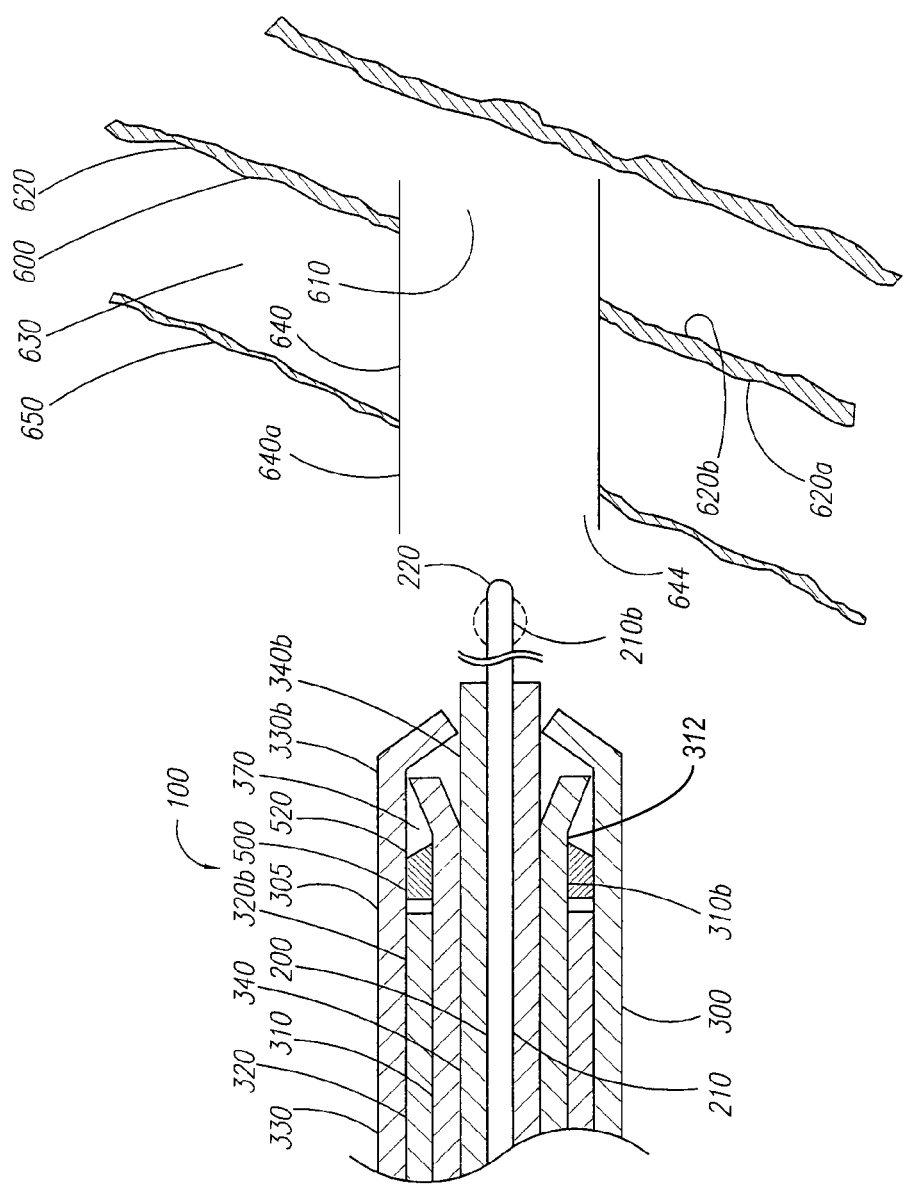
FIGS. 15A-K illustrate various steps in the deployment of embodiments of the present invention.

With reference to FIGS. 1B and 15A, to permit closure element 500 to be deployed from annular cavity 370, longitudinal extensions 335 may be sufficiently flexible to expand radially to permit distal end region 310b of carrier member 310 to move distally past cover member 330 to open annular cavity 370 such that distal end region 330b no longer extends over the space 360.

When carrier assembly 120 is assembled as a plurality of nested, telescoping members, as shown in FIGS. 2 and 8, carrier member 310 is at least partially disposed within, and slidable relative to, a lumen of pusher member 320, and support member 340 is slidably relative to pusher member 310. Pusher member 320, in turn, is at least partially disposed within, and slidable relative to, lumen 334 of cover member 330. To couple carrier assembly 120 with locator assembly 200, tubular body 210 of locator assembly 200 may be at least partially disposed within, and slidable relative to, lumen 314. The longitudinal axis of locator assembly 200 may be substantially in axial alignment with the common longitudinal axis of carrier member 310, pusher member 320, and cover member 330.

The apparatus 100 may also include support member 340 as shown in FIG. 1A. Support member 340 may be configured to slidably receive tubular body 210 of locator assembly 200 and provide radial support for distal end region 210b of tubular body 210 when locator assembly 200 is coupled with the carrier assembly 120. Carrier assembly 120 can advantageously include support member 340, for example, if tubular body 210 is not sufficiently rigid or under other circumstances in which support for tubular body 210 might be desirable. It also will be appreciated that support member 340 may also be configured to inhibit longitudinal extensions 335, which extend from distal end region 330b of cover member 330, from expanding prematurely when closure element 500 is deployed. If longitudinal extensions 335 were to expand prematurely, they may become hung up on an introducer sheath or other delivery member (if an introducer sheath or delivery member is used), the tissue, or the wall of the blood vessel. This may interfere with the proper advancement or other movement of cover member 330 and carrier assembly 120.

Support member 340 may be formed as a substantially rigid, semi-rigid, or flexible tubular member, and may include proximal end region 340a and distal end region 340b. Having an outer periphery, support member 340 may define lumen 344, extending substantially between proximal end region 340a and distal end region 340b and configured to slidably receive and support at least a portion of tubular body 210 of locator assembly 200. Support member 340, in turn, can be at least partially slidably disposed within lumen 314 of carrier member 310 such that tubular body 210 of locator assembly 200 is coupled with, and slidable relative to, carrier member 310 in the manner described in more detail above.

Support member 340 may have a predetermined length and a predetermined cross-section, both of which can be of any suitable dimension, and may have a substantially uniform cross-section. Although shown and described as being substantially separate for purposes of illustration, it will be appreciated that carrier member 310, pusher member 320, cover member 330, and/or support member 340 may be provided, in whole or in part, as one or more integrated assemblies.

With reference to FIG. 8, support member 340 may also include a distal end that is blunt, rounded and/or includes a radius or curved portion that may prevent and/or eliminate damage to tubular body 200 as tubular body is moved with respect to support member 340. In some cases during deployment, as discussed in more detail below, tubular body 200 may be inserted into a lumen of an introducer at such an angle as to require tubular body 200 to flex with respect to tube set 305 as much as between about 0 degrees and 90 degrees, preferably between about 10 degrees and 90 degrees and more preferably between 30 degrees and 60 degrees, for example when used in conjunction with a femoral artery. The above-described distal end of the distal end region 340b prevents and/or eliminates damage to tubular body 200 that may result from a sharp edge pressed along tubular body 200 during advancement of tube set 305, and more particularly, support member 340 and the distal end of the distal end region 340b.

Illustratively, the radii of the distal end of the support member 340 can have various sizes and configurations. In one configuration, the distal end radii can be about 0.002 inches. In still another configuration, the distal end radii can be about 0.004 inches. In still another configuration, the distal end radii can be about 0.002 inches or greater. Increasing the radii of the distal end of support member 340 to about 0.004 inches, for instance, can decrease the amount of force required to overcome a bend in locator assembly 200 over those devices having a distal end radii of about 0.002 inches. This is because a gap formed between the interior diameter of support member 340 and the locator assembly 200 is larger for the 0.004 inch radii than for the 0.002 inch radii.

In addition to the above, with the distal end having a radii greater than 0.002 inches, such as but not limited to 0.004 inches, there is a decrease in the possibility that the support member 340 cuts or otherwise damages the locator assembly 200 during positioning of the distal end of the apparatus 100 and subsequent deployment of the closure element 500. Further, a radii greater than 0.002 inches, such as but not limited to 0.004 inches, may not increase the forces used to split an introducer sheath and may not elongate the introducer sheath during positioning and deploying of the closure element 500.

With reference to FIGS. 1A and 1B, carrier assembly 120 may also include a portion of housing 380. For instance, the carrier assembly 120 can optionally include the top half 380c of housing 380, illustrated in FIG. 1A, and the bottom half 380d is shown in FIG. 1B. It will be understood, however, that housing 380 may be separate from the carrier assembly 120, while retaining and/or receiving all or a portion of the carrier assembly 120.

Housing 380 may be formed as an elongate member with a longitudinal axis, a periphery and may include proximal end region 380a and distal end region 380b. Thereby, when apparatus 100 is assembled, tubular body 210 of locator assembly 200 may be at least partially disposed within, and slidable relative to, tube set 305 such that distal end region 210b of tubular body 210 extends beyond distal end regions 310b, 320b, 330b, and/or 340b. Tubular body 210, carrier member 310, pusher member 320, cover member 330, and, if provided, support member 340 may be at least partially disposed within, and slidable relative to, housing 380. Proximal end region 210a of tubular body 210 and proximal end regions 310a, 320a, 330a, and/or 340a of tube set 305 can be at least partially disposed within, and slidable relative to, housing 380. Distal end regions 210b, 310b, 320b, 330b, and 340b may extend from distal end region 380b of housing 380 such that common longitudinal axis 350 of tube set 305 may be substantially axially aligned with longitudinal axis 386 of housing 380. When configured to slidably retain respective proximal end regions 210a, 310a, 320a, 330a, and 340a, housing 380 supports tube set 305 and can have one or more handles 391, 392 to facilitate use of apparatus 100. Handles 391, 392 may extend, optionally substantially radially, from the outer periphery of housing 380 and can be provided as illustrated or in any manner known in the art.

To facilitate deployment of the closure element 500, the apparatus 100 can include a triggering system 400, shown in FIG. 2, which cooperates with a portion the locator assembly 200. For instance, a portion of locator assembly 200 and a portion of triggering system 400 may cooperate and be accessible externally to housing 380, as shown in FIGS. 1A and 1B. As shown in FIGS. 1A, 1B, 4-7, triggering system 400 of apparatus 100 may be disposed substantially within housing 380. Triggering system 400 may be configured to control the relative axial movement and/or positioning of distal end regions 310b, 320b, 330b, and 340b and/or locator assembly distal end region 210b. Axial motion of one or more of carrier member 310, pusher member 320, cover member 330, and support member 340 and/or tubular body 210 may be attained, for example, by applying an axial force to triggering extension 405.

Triggering system 400 may include a set of block members including carrier block 410, pusher block 420, cover block 430, and support block 440, each of which may be formed integrally with or securely attached to its respective member of carrier assembly 120. The block members may be adapted to selectably couple and decouple carrier member 310, pusher member 320, cover member 330, and support member 340 relative to one another in order to provide axial movement of those components in a predetermined manner intended to deliver closure element 500 in the manner described herein. For example, when carrier assembly 120 reaches a first predetermined distal position, support member 340 may be decoupled from carrier member 310, pusher member 320, and cover member 330, and may be thereafter substantially inhibited from further axial movement. Thereby, carrier member 310, pusher member 320, and cover member 330 may be directed distally as support member 340 remains substantially stationary. Subsequently, carrier member 310 and cover member 330 can be decoupled from pusher member 320 and thereby inhibited from further axial movement. Pusher member 320 may be directed distally as support member 340, carrier member 310, and cover member 330 remain substantially stationary, as described more fully herein.

Carrier block 410 may be disposed on proximal end region 310a of carrier member 310 and may include trigger extension 405, which extends through a slot in housing 380 to the exterior of housing 380, accessible by a user. This carrier block 410, as shown in FIG. 3A, may include a pair of grooves 413a-b formed on a peripheral surface of carrier block 410. Grooves 413a-b may be adapted to receive and retain a pair of tabs 445a-b formed on a pair of legs 444a-b extending distally from support block 440, thereby selectably coupling support block 440 to carrier block 410. Carrier block 410, as illustrated in FIG. 1A, may also include a pair of distal tabs 416a-b extending from the distal end of carrier block 410, and adapted to engage a pair of slots 423a-b formed on the proximal end of pusher block 420.

As shown in FIGS. 1A and 3A, carrier block 410 may also include a pair of arms 414a-b extending in the proximal direction from the proximal end of carrier block 410, each of arm 414a-b having an outward directed tab 415a-b at its proximal end. Tabs 415a-b may be adapted to selectably engage a pair of slots 387a-b (FIG. 1B) formed on the interior surface of housing 380 near its proximal end and, when so engaged, to fix the axial position of carrier block 410 and, with it, carrier assembly 120 relative to housing 380. Tabs 415a-b may be disengaged from slots 387a-b FIG. 1B) in housing 380 when locator assembly block 280 is moved axially in the distal direction in the following manner. As locator assembly block 280 is advanced distally, the interior surfaces of the ramps 283a-b on locator assembly block legs 282a-b engage the exterior surfaces of tabs 415a-b and cause carrier block arms 414a-b to flex inward, releasing tabs 415a-b from the slots 387a-b in the housing, thereby freeing carrier block 410 and carrier assembly 120 to move axially. Thus, axial movement of carrier block 410 within apparatus 100 is inhibited until locator assembly block 280 is advanced to transition locator assembly 200 to the expanded condition, simultaneously releasing tabs 415a-b on carrier block 410.

Pusher block 420 may be disposed on proximal end region 320a of pusher member 320. As described above, pusher block 420 may include a pair of slots 423a-b formed on its proximal end, and adapted to selectably engage distal tabs 416a-b extending from the distal end of carrier block 410. Pusher block 420 may also include a pair of grooves 424a-b formed on its peripheral surface, the grooves 424a-b being adapted to engage a pair of tabs 435a-b formed on a pair of forks 434a-b extending from the proximal side of cover block 430 to selectably couple cover block 430 to pusher block 420.

Cover block 430 may be disposed on proximal end region 330a of cover member 330. As described above, cover block 430 may include a pair of forks 434a-b extending from the proximal end of the cover block 430, each of forks 434a-b having an inward directed tab 435a-b adapted to engage grooves 424a-b on the peripheral surface of pusher block 420 to selectably couple cover block 430 to pusher block 420.

Support block 440 may be disposed on proximal end region 340a of support member 340. As described above, support block 440 may include a pair of legs 444*a-b* extending from the distal end of the support block 440, each of legs 444*a-b* having an inward directed tab 445*a-b* adapted to engage grooves 413*a-b* formed on the surface of carrier block 410 to selectably couple support block 440 to carrier block 410.

Carrier block 410, pusher block 420, cover block 430, and support block 440 are shown in FIGS. 2, 3A, 4-5 in their fully coupled state, with support block 440 coupled to carrier block 410, pusher block 420 coupled to carrier block 410, and cover block 430 coupled to pusher block 420. In this arrangement, carrier assembly 120 comprises a coaxial set of tubes as shown in FIG. 8, with support member 340 slidably retained substantially within carrier member 310, which is in turn slidably retained substantially within pusher member 320, which is in turn slidably retained substantially within cover member 330.

Triggering system 400 of apparatus 100 may include an energy storing element that is used in the final stage of closure element 500 delivery processes. The energy storing element, such as, but not limited to, a spring, such as pusher spring 425 shown in FIGS. 1A, 1B, 6 and 7, may be substantially retained in a spring cavity 417 formed in carrier block 410 and coaxially surrounds a proximal end region 310*a* of carrier member 310. Pusher spring 425 is capable of expanding and contracting, storing potential energy as it is contracted and releasing energy as it expands. In its fully expanded state, the pusher spring 425 has a length that is greater than the length of spring cavity 417. The cross-sectional dimension of pusher spring 425 may be such that it backs up against and contacts the proximal end of pusher block 420. Thus, when pusher spring 425 is in place between carrier block 410 and pusher block 420, pusher spring 425 is capable of imparting a force biasing carrier block 410 away from pusher block 420.

Prior to delivery of closure element 500, the distal end of carrier block 410 is in physical contact with the proximal end of pusher block 420. In this pre-delivery condition, pusher spring 425 is in a contracted state and is maintained fully within spring cavity 417. A catch member 418 serves the function of maintaining the carrier block 410 and pusher block 420 in the pre-delivery condition against the spring force of pusher spring 425, the force of which would otherwise force apart carrier block 410 from pusher block 420. Catch member 418 may be a U-shaped piece of metal, plastic, or other rigid material that engages first groove 419*a* formed on the surface of carrier block 410 and second groove 419*b* formed on the surface of pusher block 420. With reference to FIGS. 1A and 1B, pusher block 420 includes hole 426 extending through a portion thereof, with one end of hole 426 opening into groove 419*b*. Hole 426 is adapted to receive trip pin 427. During the closure element deployment process, trip pin 427 is advanced through hole 426, where it encounters catch member 418 retained in the groove 419*b*. Further advancement of trip pin 427 causes catch member 418 to become disengaged from groove 419*b*, thereby releasing the force of pusher spring 425.

The operation of the triggering system 400 of the apparatus 100 is illustrated in FIGS. 2-8 with the closure element 500 disposed substantially within the apparatus 100. As shown in FIGS. 2-3B, apparatus 100 has an initial position in which locator assembly block 280 is extended proximally and triggering system 400 is in its most proximal position. Accordingly, the locator assembly 200 is in its unexpanded state, as shown in FIG. 3B. At a point in time that the distal end region 210*b* of the locator assembly 200 has been positioned as desired (for example, within the blood vessel), locator assembly block 280 is depressed distally, as shown in FIG. 4, thereby transitioning locator assembly 200 to the expanded state, as shown in FIG. 3C, and, simultaneously, releasing triggering system 400 from the initial position (in the manner described above) such that triggering system 400 can be advanced distally within the housing 380.

Triggering system 400 can then be advanced distally within housing 380, thereby advancing tube set 305 into position adjacent the blood vessel. At a first predetermined position, shown in FIGS. 4 and 5, support block 440 encounters a support stop (not shown) on the interior surface of housing bottom half 380*d* that inhibits support block 440 from advancing further distally. As a result, an application of additional distal force to triggering system 400 causes support block 440 to decouple from carrier block 410. More specifically, tabs 445*a-b* on legs 444*a-b* of support block 440 disengage from grooves 413*a-b* on carrier block 410. Thus, support block 440 remains in the position shown in FIGS. 4 and 5, while carrier block 410 is able to advance further distally upon application of force to triggering system 400.

Turning to FIGS. 6-8, as the triggering system 400 is advanced further distally; cover block 430 engages a cover stop on the interior surface near the distal end region 380*b* of housing 380, thereby inhibiting additional distal advancement of cover block 430. In addition, trigger extension 405 engages handle 391 of the apparatus, thereby inhibiting additional distal advancement of carrier block 410.

Closure element 500 is next deployed by releasing pusher spring 425, which causes pusher block 420 (and, thus, pusher member 320 (FIG. 1A)) to advance distally, deploying closure element 500 in the manner described above. As previously described, pusher spring 425 is released by disengaging catch member 418 from groove 419*b* on pusher block 420, thereby releasing pusher spring 425 to force pusher block 420 and, thus, pusher member 320 distally relative to carrier block 410. This action causes pusher member 320 to deploy closure element 500 from within tubeset 305. The catch member 418 is disengaged from groove 419*b* by applying a force to a trigger 401, which, in the deployment position, is aligned with trip pin 427 retained in pusher block 420. A trigger spring 402 biases trigger 401 outward relative to housing 380, with a portion of the trigger 401 extending through a hole 130 (FIG. 1B) in housing 380. A user applies an inward directed force to trigger 401 to counteract the biasing force of trigger spring 402 and force trigger 401 against the trip pin 427.

With reference to FIGS. 1A and 6, in addition to deploying closure element 500, the distal advancement of pusher block 420 also causes locator release system 490 to activate, thereby transitioning locator assembly 200 from the expanded state to the unexpanded state. As pusher block 420 advances distally to deploy closure element 500 in the manner described above, pusher block 420 also engages engagement member 493 of locator release system 490 and advances locator release rod 491 distally. This action causes release tab spacer block 492 to disengage from release tabs 284*a-b* on locator assembly block 280 (see FIG. 1), thereby releasing locator assembly block 280, which returns to its proximal position, causing locator assembly 200 to return to the unexpanded state. An indicator window (not shown) may be formed in housing 380 to give a visual indication that tab spacer block 492 has disengaged and that locator assembly 200 has returned to the unexpanded state. The deployment of closure element 500 and locator release actions occur nearly simultaneously.

Referring now to FIGS. 9-13, an alternative embodiment of the apparatus is shown in accordance with the present invention. The apparatus of the alternative embodiment is functionally similar to that of the device previously described above and shown in FIGS. 1-8 in most respects, wherein certain features will not be described in relation to the alternative embodiment wherein those components function in the manner as described above and are hereby incorporated into the alternative embodiment described below.

Generally, the apparatus 1000 illustrated in FIGS. 9-13 can accommodate for variations in the size of the physicians hand and grip by selectively reducing the distance between the device's handle portion and a portion of the triggering system usable to deploy the closure element and/or move a carrier assembly. Advancement of a locator assembly for locating the blood vessel wall prior to deploying the closure element can at least partially advance a portion of the triggering system of the apparatus including a trigger extension graspable by a physician or clinician. This partial movement reduces the gap or throw between the trigger extension and the handle portion. In this manner, a physician or clinician does not need to stretch uncomfortably to position a thumb or finger on the trigger extension, grasping the handle portion, and maintaining the device in the desired orientation relative to the tissue and/or the puncture site.

Figure 9:
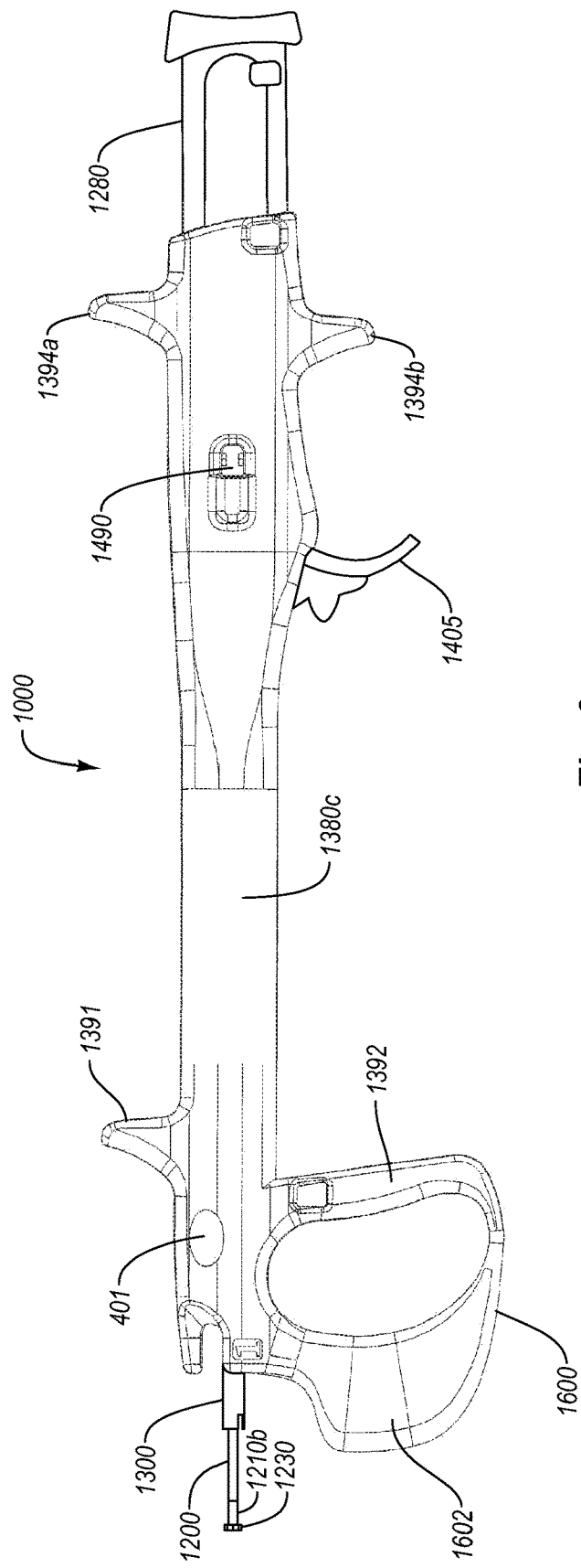
FIG. 9 illustrates a plan view of an alternative embodiment of an apparatus for closing openings in tissue in accordance with the present invention.
Figure 10:
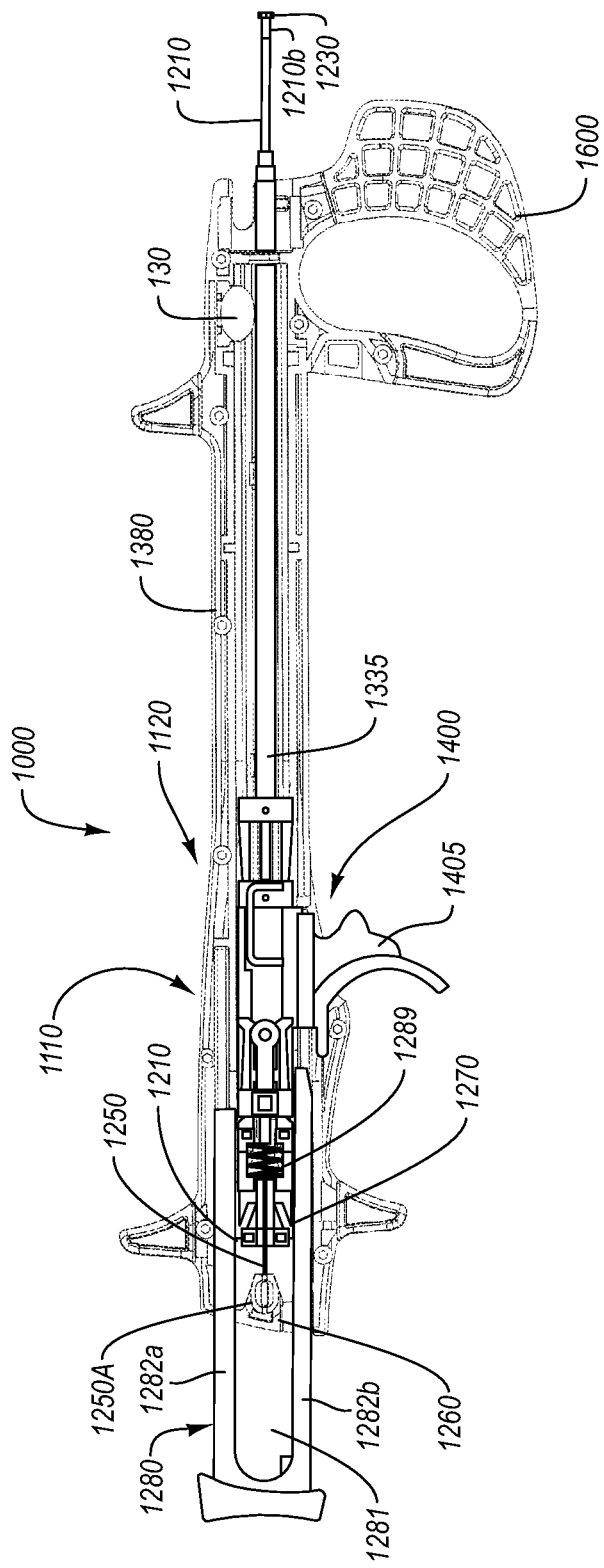
FIG. 10 illustrates a portion of a housing half of the alternative embodiment of FIG. 9, illustrating the functional components thereof.

As shown in FIG. 9, the apparatus 1000 can include a housing 1380 comprising housing halves 1380c and 1380d (FIG. 10). These housing halves 1380c and 1380d (FIG. 10), either individually or collectively, can form one or more handle, hand grip, or finger portions which a physician or clinician can grip or hold to manipulate the apparatus 1000. As illustrated, the apparatus 1000 can include finger grip 1391 and finger grip 1392 at a distal end and finger grips 1394a and 1394b on the proximal end of housing 1380 to facilitate use of locator assembly 1110, and specifically plunger 1280.

In addition, the apparatus 1000 can include handle, hand grip, or finger portion disposed on the distal end of housing 1380 configured to be engaged by a user when advancing housing 1380 to deploy closure element 500 (FIG. 1A). This handle or handle portion or hand grip portion can include a shaped grasping portion 1600 and an elongate grasping portion 1392 spaced apart from the shaped grasping portion 1600. Each of the portions 1392 and 1600 may be contoured to be received by a user's hand. For instance, the grasping portion 1600 can provide a stable base upon which the physician or clinician can move the device or apparatus as the closure element is positioned and deployed. This grasping portion 1600 can have a shaped portion 1602 having a curved configuration that can receive at least a thumb or finger of the physician as the physician or clinician holds the apparatus 1000. The curved configuration or profile allows the physician to grasp the handle or handle grip portion while resting their hand, wrist or forearm upon a patient during the procedure, such as deployment of the closure element, thereby providing stability during use of the device.

It will be understood that although reference is made to one particular configuration of the handle, hand grip, or finger portions, one skilled in the art will appreciate and can identify various other configurations of handle portion that can perform the function of providing a stable base for manipulation of the apparatus 1000. For instance, and not by way of limitation, the handle portion can be planar rather than curved. Further, the handle portion can include one or more finger receiving holes. In addition, the handle portion can include a material to provide cushioning or comfort to the physician and/or clinician. For example, flexible, yielding, or elastic materials can be formed or applied to all or a portion of the handle portion.

Referring now to FIGS. 9 and 10, apparatus 1000 can be provided as one or more integrated components and/or discrete components. For instance, and not by way of limitation, apparatus 1000 may include locator assembly 1110 and carrier assembly 1120. For purposes of illustration, locator assembly 1110 and carrier assembly 1120 are shown in FIG. 10 as comprising substantially separate assemblies. As desired, however, locator assembly 1110 and carrier assembly 1120 may each be provided, in whole or in part, as one or more integrated assemblies. Portions of locator assembly 110 and/or carrier assembly 120 can also be used as part of apparatus 1000. Alternatively, modified versions of locator assembly 110 and/or carrier assembly 120 can be used.

Locator assembly 1110 may be constructed in the manner previously described above, including a flexible or semi-rigid tubular body (such as an elongate rail) with a longitudinal axis. The tubular body can have a proximal end region and a distal end region and can include a predetermined length and a predetermined outer cross-section, both of which can be of any suitable dimension. The distal end region of the locator assembly may include a substantially rounded, soft, and/or flexible distal end or tip to facilitate atraumatic advancement and/or retraction of the distal end region into a blood vessel or other opening in tissue. As desired, a pigtail (not shown) may be provided on the distal end to further aid atraumatic advancement of the distal end region. The distal end region of locator assembly 1110 may be selectably controllable between an unexpanded state and an expanded state.

As shown in FIG. 10, apparatus 1000 can include carrier assembly 1120 which is functionally equivalent to carrier assembly 120 (FIG. 1A) described above and will not be described in detail with regard to the alternative embodiment. As with carrier assembly 120, carrier assembly 1120 may be coupled with, and slidable relative to, locator assembly 1110. Carrier assembly 1120 may be configured to receive and retain the closure element 500 (shown in FIGS. 14A-14G), which can be disposed substantially within carrier assembly 1120. Carrier assembly 1120 can function to position closure element 500 substantially adjacent to an opening to be closed, and to deploy closure element 500.

Figure 11A:
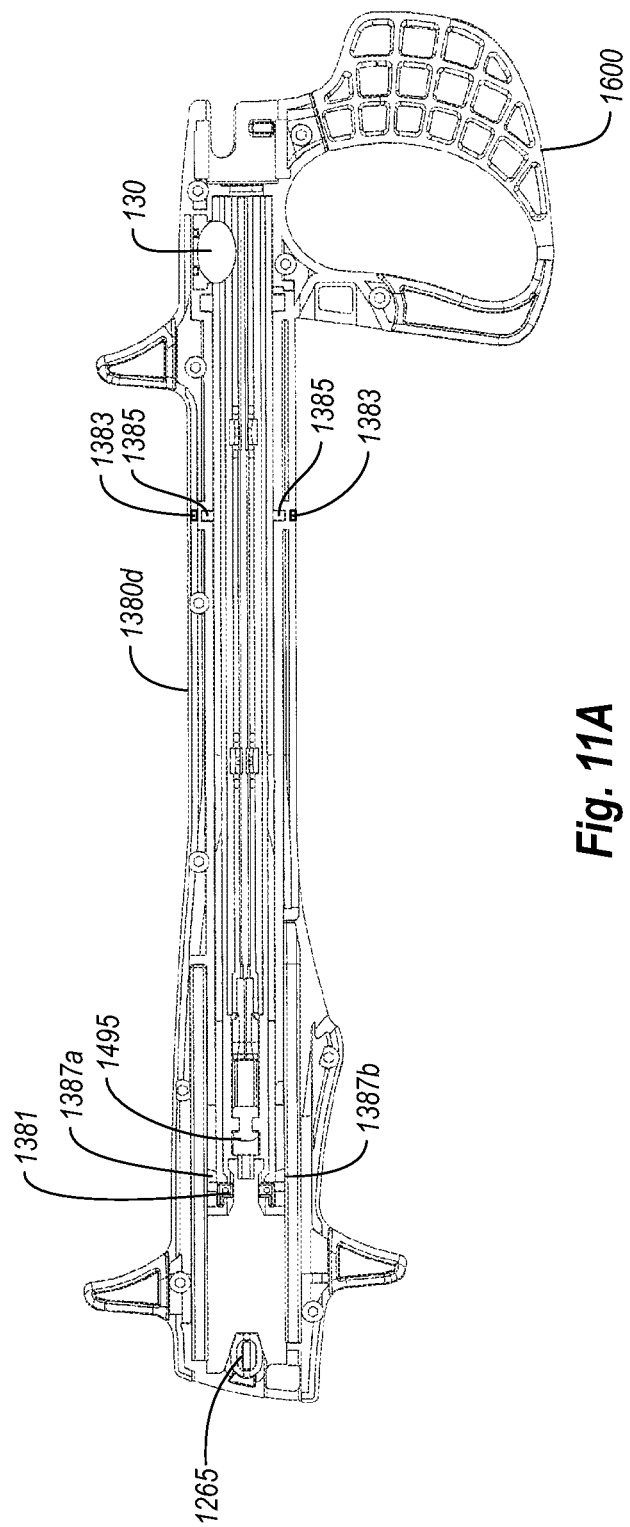
FIG. 11A illustrates a portion of a housing half of the alternative embodiment of FIG. 9, without certain functional components.

Referring now to FIGS. 10 and 11, locator assembly 1110 of the alternative embodiment will be described in greater detail. As with the previous locator assembly, a control member 1250, such as a rod, wire, or other elongate member, can be moveably disposed within a lumen (not shown) formed by tubular body 1210 and extend substantially between the proximal end region and the distal end region. Control member 1250 can have a proximal end region 1250a that may be coupled with a control block 1260, and a distal end region that may be coupled with the distal end region of locator assembly 1110, expansion members 1230, and/or movable end regions of substantially flexible members, such as flexible members 232 (FIG. 3B). Control block 1260 may be constructed in a tubular shape and formed of a metal or rigid plastic, and is adapted to be retained in control block cavity 1265 (FIG. 11A) formed on the internal surface of the housing bottom half 1380d, to thereby maintain control block 1260 in a substantially fixed position relative to housing half 1380d and so housing 1380. The locator assembly 1110 can selectively transition distal end region 1210b, expansion members 1230, and/or the substantially flexible members between the unexpanded and expanded states by moving tubular body 1210 axially relative to control member 1250. Additionally as shown in FIG. 11A, apertures 1383 may be placed adjacent to an in communication with detents 1385, wherein in use as described below, tabs 415*a* and 415*b* (FIG. 1A) engage the detents 1385 during use. Apertures 1383 are configured to receive the tip of a medical device, such as a tip of a dilator from a sheath assembly, wherein the tip of the dilator can be utilized to disengage the tabs 415*a* and 415*b* (FIG. 1A) from the detents 1385 thereby releasing the locked position of the device. This enables a user to move the trigger assembly 1400 (FIG. 10) proximally (toward the user) after the clip has been deployed in the event that the device becomes stuck within the patient, thereby providing a safety release mechanism. It shall be appreciated that the apertures 1383 may be replaced by other features such a recessed buttons that become exposed with the engagement of the tabs with the detents or alternatively a specific tool may be provided with the device.

With reference to FIGS. 10 and 11B, to facilitate movement of carrier assembly 1120 to reduce the distance between a trigger extension 1405 and the distal end of housing 1380, the functionality of locator assembly block 280 (FIG. 1A) can be provided through the combination of a plunger 1280, a tubular body block 1270, and a spring retainer 1290. In addition to providing the functionality of locator assembly block 280, including but not limited to, controlling movement of expansion members 1230, plunger 1280, tubular body block 1270, and spring retainer 1290 aid with moving trigger extension 1405 toward the distal end of housing 1380.

With reference to FIG. 11B, plunger 1280 can include two spaced apart legs 1282*a-b* separated by a plunger member 1284 to form a slot 1281 therebetween. The legs 1282*a-b* are spaced apart sufficiently to accommodate or receive a portion of tubular body block 1270 and/or spring retainer 1290 therebetween. Each of the legs 1282*a-b* can have a stepped configuration, such as shown in FIG. 11D. Plunger 1280 may be slidably received and retained within grooves formed in the proximal end of housing 1380, with the proximal end of plunger 1280 extending from the proximal end of housing 1380.

Plunger 1280 may be constructed of metal, plastic, or other rigid material. The proximal end of plunger 1280 may have a slot 1281 formed therein. Slot 1281 may have a size sufficient to accommodate control block 1260 and control block cavity 1265, and to allow plunger 1280 to travel axially relative to housing 1380. As mentioned, the distal end of plunger 1280 has a pair of distally extending legs 1282*a-b* with optional ramps 1283*a-b* on respective inward facing surfaces. In addition, formed in each leg 1282*a-b* is a recess 1285 within which moves a protrusion 1286 having a dent 1288 that can interlock with at least one of tubular body block 1270 or spring retainer 1290 as plunger 1280 is moved distally.

Figure 12:
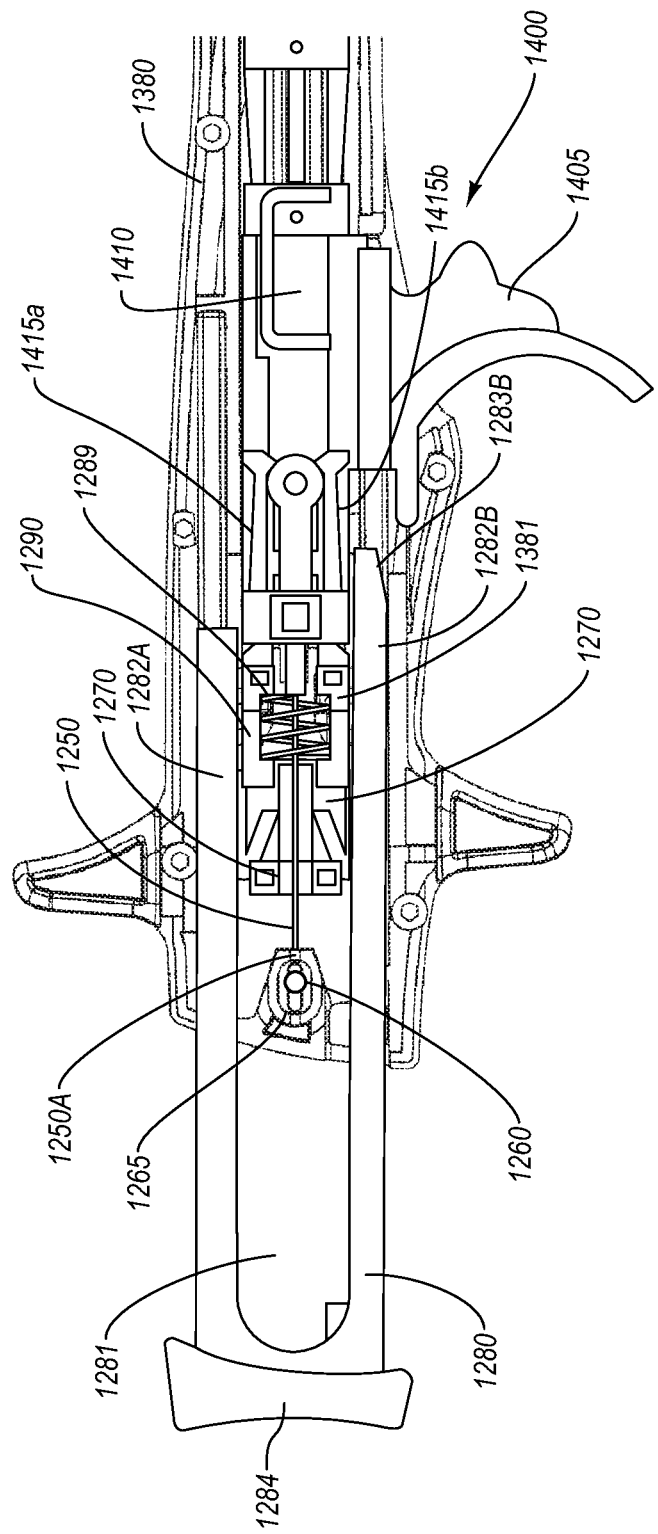
FIG. 12 illustrates a close-up cross-sectional view of the proximal end of the apparatus shown in FIG. 9, illustrating the initial position of the locator control system.

With reference to FIGS. 11B and 11E, tubular body block 1270 may be formed integrally with or attached securely to tubular body 1210. The tubular body block 1270 can include a pair of extending legs 1272*a-b*, with each of legs 1272*a-b* having a ramp portion 1273*a-b* on its inward facing surface. Ramp portions 1273*a-b* can cooperatively engage tabs, not shown but similar to tabs 415*a-b* (FIG. 1A), of carrier block 1410 (FIG. 12). In an initial state, the tabs 415*a-b* (FIG. 1A) can be engaged in slots 1387*a-*1387*b* (FIG. 11A) formed in housing halve 1380*d* to hold triggering system 1400 (FIG. 10) in a fixed axial relationship with housing 1380.

Extending between legs 1272*a-b* is an intermediate member 1274 that can include a pair of upwardly extending extension 1276*a-b* and a tab 1278, shown in dotted lines in FIG. 11B. Extensions 1276*a-b* are received within the space between legs 1282*a-b* of plunger 1280. Stated another way, tubular body block 1270 can be held in a fixed axial relationship with respect to plunger 1280 through the engagement of legs 1282*a-b* and legs 1272*a-b*. The tab 1278 can be adapted to cooperate with spring retainer 1290 and optionally lock with a portion of spring retainer 1290 as plunger 1280 moves distally, as will be described in more detail hereinafter.

Extending from intermediate member 1274 in the same direction as legs 1272*a-b* is a tubular portion 1279 that slidably cooperates with spring retainer 1290 and receives tubular body 1210 within a lumen. Further, tubular portion 1279 can cooperate with a locator assembly spring 1289 (FIG. 10) which biases tubular body block 1270 and/or spring retainer 1290 relative to housing 1380.

As shown in FIGS. 11B and 11F, spring retainer 1290 has a wall portion 1291 with a recess 1292 that can receive tubular portion 1279 of tubular body block 1270. The wall portion 1291 defines a channel 1294 within which can be received locator assembly spring 1289 (FIG. 10). For instance, locator assembly spring 1289 (FIG. 10) can extend from wall portion 1291 to locator assembly spring stop 1381 (FIG. 11A) to bias movement of spring retainer 1290, tubular body block 1270, and so locator assembly 1110.

Spring retainer 1290 can further include arms 1296*a-b*. Arms 1296*a-b* can include a movable portion 1297*a-b* that can flex or move to receive tab 1278 of tubular body block 1270. For instance, tab 1278 can include curved surfaces that cooperate and receive a portion of movable portion 1297*a-b* as tubular body block 1270 moves relative to spring retainer 1290. Alternatively, tab 1278 can be positioned within a space 1299 between wall portion 1291 and movable portion 1297*a-b* before manipulation or operation of apparatus 1000. It will be understood that other portions of arms 1296*a-b* can flex or move, whether or not movable portions 1297*a-b* move.

In addition to arms 1296*a-b*, spring retainer 1290 can include release tabs 1298*a-b*. These release tabs 1298*a-b* can function in a similar manner to tabs 284*a-b* (FIG. 1A). For instance, tabs 1298*a-b* can cooperate with a locator release system 1490 in a manner substantially similar to the embodiments described above. For example, release tabs 1298*a-b* can engage release cavity 1495 on housing 1380, and can be held from releasing by release tab spacer block 1492.

Generally, plunger 1280, tubular body block 1270, and spring retainer 1290 can be formed of metal, plastic, or other material, whether or not rigid, substantially rigid, or flexible. As such, plunger 1280, tubular body block 1270, and spring retainer 1290 can be formed from medical grade synthetic materials or materials that can be sterilized or otherwise cleaned.

Figure 13:
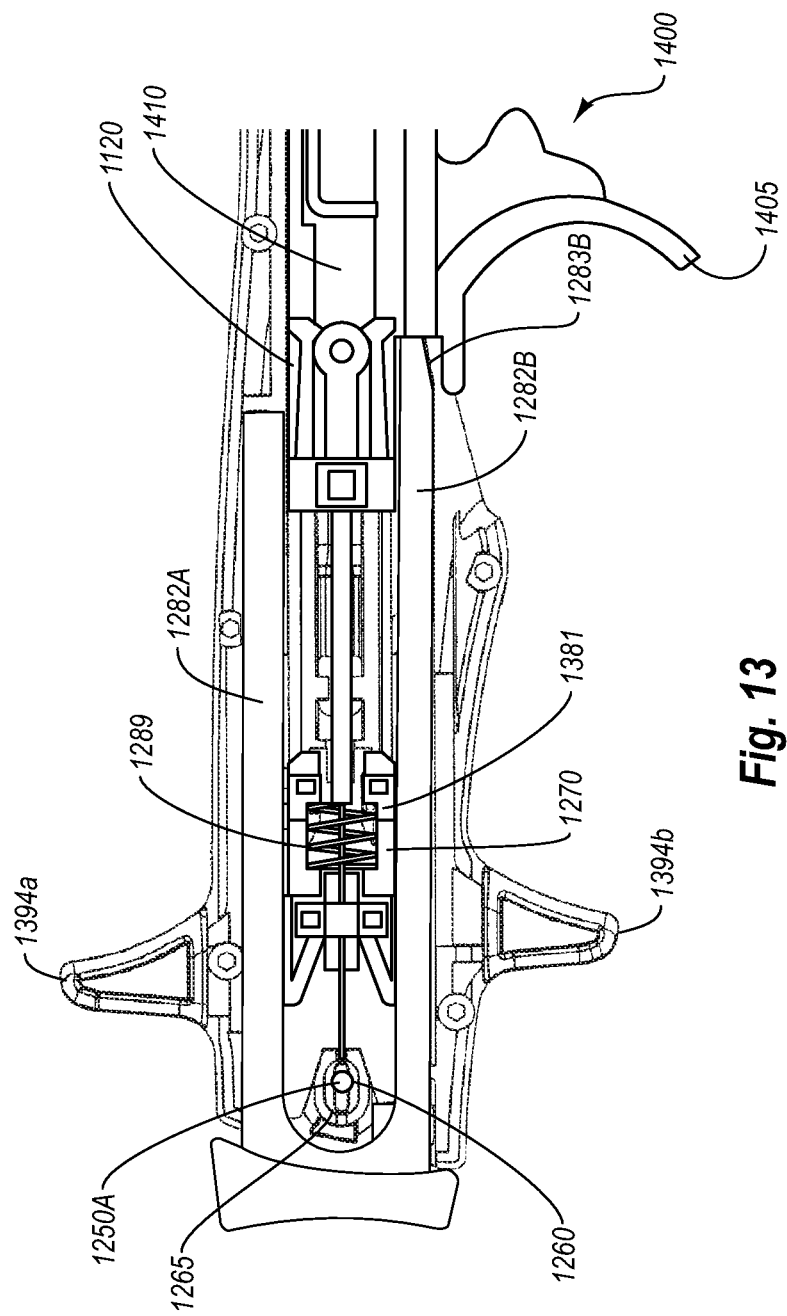
FIG. 13 illustrates a close-up cross-sectional view of the proximal end of the apparatus shown in FIG. 9, illustrating the final position before clip release of the locator control system.
Figure 14A:
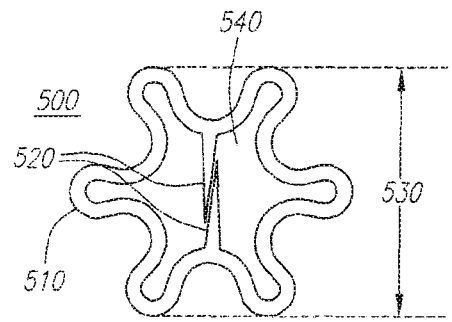
FIGS. 14A-14G illustrate various embodiments of closure elements that can be utilized with the apparatus of the present invention.
Figure 14B:
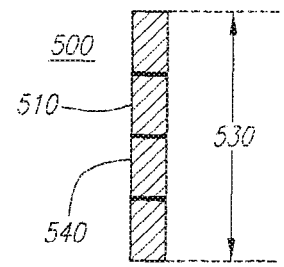
Figure 14C:
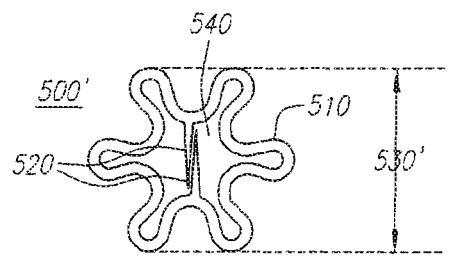
Figure 14D:
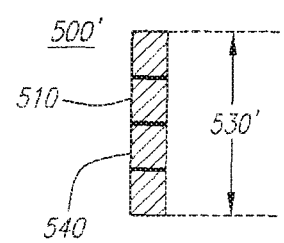
Figure 14E:
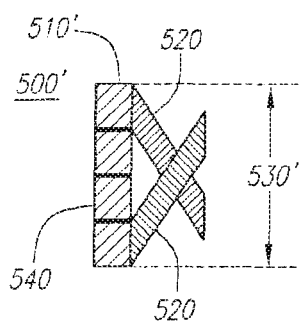
Figure 14F:
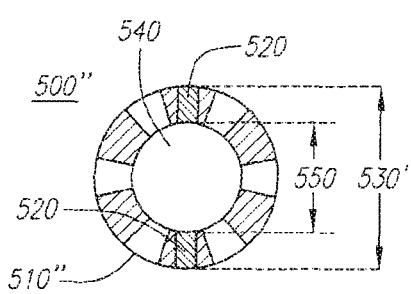
Figure 14G:
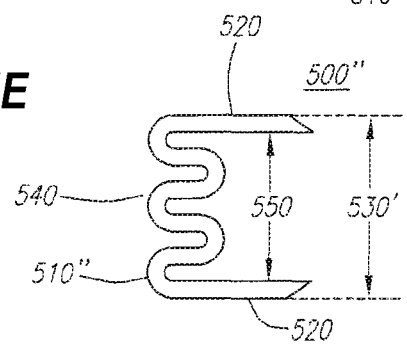

Turning now to FIGS. 12 and 13, illustrated are the operational positions of the apparatus 1000 in (i) an initial state with the expansion members 1230 (FIG. 9) in an unexpanded condition and (ii) a state with the expansion members 1230 (FIG. 9) in an expanded condition.

With reference to FIG. 12, in the initial state plunger 1280 extends from the distal end of housing 1380, expansion members 1230 are in an unexpanded condition, and locator assembly spring 1289, which can be located coaxially with tubular body block 1270, may be located between spring retainer 1290 and the proximal side of locator assembly spring stop 1381 formed on the inner surface of housing bottom half 1380*d*. In this initial state locator assembly spring 1289 is held in a biased state. Optionally, a portion of carrier assembly 1120 (FIG. 10) can be associated with legs 1282a-b of plunger 1280 and contact carrier a portion of carrier assembly 1120 (FIG. 10).

Once a user presses on plunger 1280 to expand expansion members 1230, that is moving plunger 1280 toward expansion members 1230, tubular body block 1270 and tubular body 1210 are advanced distally by distal advancement of plunger 1280. Upon advancement, and with reference to FIGS. 1A and 10-12, ramp members 1273a-b press tabs 415a-b, which are hidden by plunger 1280 in FIG. 12, releasing carrier block 1410 to slide axially in housing 1380, and release tabs 1298a-b engage in retaining grooves 1387a-b in cooperation with locator release system 1490, which is functionally equivalent to locator release system 490 described above, thereby fixing spring retainer 1290 and tubular body block 1270 axially with respect to housing 1380, and fixing expansion members 1230 of locator assembly 1110 in an expanded state. Also during advancement, tab 1278 of tubular body block 1270 advances between arms 1296a-b of spring retainer 1290, extending the arms outwardly until tab 1278 advances past the ends of arms 1296a-b, causing arms 1296a-b to extend behind tab 1278, thereby coupling spring retainer 1290 and tubular body block 1270, and fixing tubular body block axially prior to activation of locator release system 1490. Also, once advanced the plunger 1280 is locked into a distal position by legs 1272a and 1272b.

Further axial movement of plunger 1280 can allow engagement of distal end 1283b of leg 1282b and carrier block 1410, thereby moving carrier block 1410 distally along with carrier assembly 1120, as illustrated in FIG. 13. This additional movement of carrier assembly 1120 also moves trigger extension 1405, shortening the distance required to fully engage the carrier assembly 1120. Combining the deployment of locator assembly 1110 and the partial advancement of carrier assembly 1120 in a single step, allows for a reduction in travel of the trigger block and trigger extension 1405. This reduction of travel allows for a greater variation in user strength as well as the physical size of a users hand to fit better with device 1000 as illustrated.

Once locator assembly 1110 is deployed, carrier assembly 1120 can be advanced distally by exerting force on trigger extension 1405, and can be fixed in the distal position in the manner described above with reference to other embodiments above. After the locator has been deployed and the carrier assembly initially advanced as shown in FIG. 13, device 1000 functions in the manner described above with regard to other embodiments of the present invention and thus will not be described in detail with regard to this embodiment.

In some embodiments, the tubular body block and the release block may be integrally formed. When the tubular body block and the release block are integrally formed, axial movement of the locator assembly block can force outward movement of tabs holding the tubular body block to the locator assembly block, allowing the integrally formed tubular body block and release block to slide distally with respect to the locator assembly block, and cause the release tabs to load the locator release system to release as discussed above.

Referring now to FIGS. 14A-14G illustrating embodiments of a closure element that can be used as part of or with the apparatus 100. The closure element, generally identified with reference numeral 500, may have a generally annular-shaped body defining a channel and one or more barbs and/or tines for receiving and engaging the blood vessel wall and/or the tissue around the opening. Although the closure element has a natural shape and size, the closure element can be deformed into other shapes and sizes, as desired, and can be configured to return to the natural shape and size when released. For example, closure element 500 can have a natural, planar configuration with opposing tines and a natural cross-section. The closure element can be formed from any suitable material, including any biodegradable material, any shape memory material, such as alloys of nickel-titanium, or any combination thereof. Additionally, it is contemplated that the closure element may be coated with a beneficial agent or be constructed as a composite, wherein one component of the composite would be a beneficial agent. As desired, the closure element may further include radiopaque markers (not shown) or may be wholly or partially formed from a radiopaque material to facilitate observation of the closure element using fluoroscopy or other imaging systems. Exemplary embodiments of a closure element are disclosed in U.S. Pat. Nos. 6,197,042, 6,623,510, 6,461,364, 6,391,048, and 6,623,510. The disclosures of these references and any others cited therein are expressly incorporated herein by reference.

As described previously, and with reference to FIG. 15A, closure element 500 can be disposed within the carrier assembly and adjacent to the distal end of pusher tube 320. As shown in FIG. 15A, for example, the reduced closure element 500 may be slidably received over distally-increasing cross-section 318b of distal end region 310b of carrier member 310 and disposed about periphery 312 of carrier member 310 adjacent to space 360. Since reduced cross-section 530 of reduced closure element 500 is less than cross-section 318b of distally-increasing cross-section 318b, reduced closure element 500 must be temporarily radially deformed to be received over distal end region 310b. Also, as reduced closure element 500' (FIG. 14C) is received over distal end region 310b, opposing tines 520 of reduced closure element 500' (FIG. 14C) engage distal end region 310b. Reduced closure element 500' (FIG. 14C) thereby forms substantially tubular closure element 500", illustrated in FIG. 14G, with the ends of the barbs and/or tines extending towards the distal end of the apparatus 100.

The apparatuses of the present invention may be configured to be utilized with a sheath, wherein the sheath is inserted or otherwise positioned into an opening in a body comprising a lumen. The sheath generally comprises a substantially flexible or semi-rigid tubular member having a proximal end region and a distal end region and includes a predetermined length and a predetermined cross-section, both of which can be of any suitable dimension. The sheath forms a lumen that extends along a longitudinal axis or the sheath and substantially between the proximal and distal end regions. The lumen can have any suitable internal cross-section and is suitable for receiving one or more devices (not shown), such as a catheter, a guide wire, or the like. The lumen is configured to slidably receive the tubular body of the locator assembly and/or the tube set of the carrier assembly of the devices in accordance with the present invention.

Since the internal cross-section of the sheath may be less than or substantially equal to the predetermined cross-section of the cover member, the sheath may be configured to radially expand, such as by stretching, to receive the tube set. Alternatively, or in addition, the sheath may be advantageously configured to split as the tube set is received by, and advances within the lumen of the sheath, thereby permitting the apparatuses to access the blood vessel wall. To facilitate the splitting, the sheath can include one or more splits, such as longitudinal splits, each split being provided in a manner known in the art. Each split is configured to split the sheath in accordance with a predetermined pattern, such as in a spiral pattern. It will be appreciated that, when the internal cross-section of the sheath is greater than the predetermined cross-section of the cover member, it may not be necessary for the sheath to be configured to radially expand and/or split. In addition to, or as an alternative to, the apparatus may include a cutting means that initiates a tear line or split in the sheath when the sheath is engaged with the distal end of the apparatus.

The sheath may be advanced over a guide wire or other rail (not shown), which has been positioned through the opening and into the blood vessel using conventional procedures such as those described above. Preferably, the blood vessel is a peripheral blood vessel, such as a femoral or carotid artery, although other body lumens may be accessed using the sheath as will be appreciated by those skilled in the art. The opening, and consequently the sheath, may be oriented with respect to the blood vessel such as to facilitate the introduction of devices through the lumen of the sheath and into the blood vessel with minimal risk of damage to the blood vessel. One or more devices (not shown), such as a catheter, a guide wire, or the like, may be inserted through the sheath and advanced to a preselected location within the patients body. For example, the devices may be used to perform a therapeutic or diagnostic procedure, such as angioplasty, atherectomy, stent implantation, and the like, within the patents vasculature.

FIGS. 15A-K illustrate one exemplary manner to deploy closure element 500 by apparatuses according to the present invention. For purposes of continuity, reference numbers to the first discussed embodiment are used, but it will be evident that other embodiments discussed above may be used in a similar fashion.

A sheath 640 may be inserted or otherwise positioned through a patient's skin 650 and tissue 630 and within the blood vessel 600 or other body lumen via the opening 610. This provides access to the blood vessel 600 through the blood vessel wall 620 for performance of a therapeutic or diagnostic procedure.

Figure 15B:
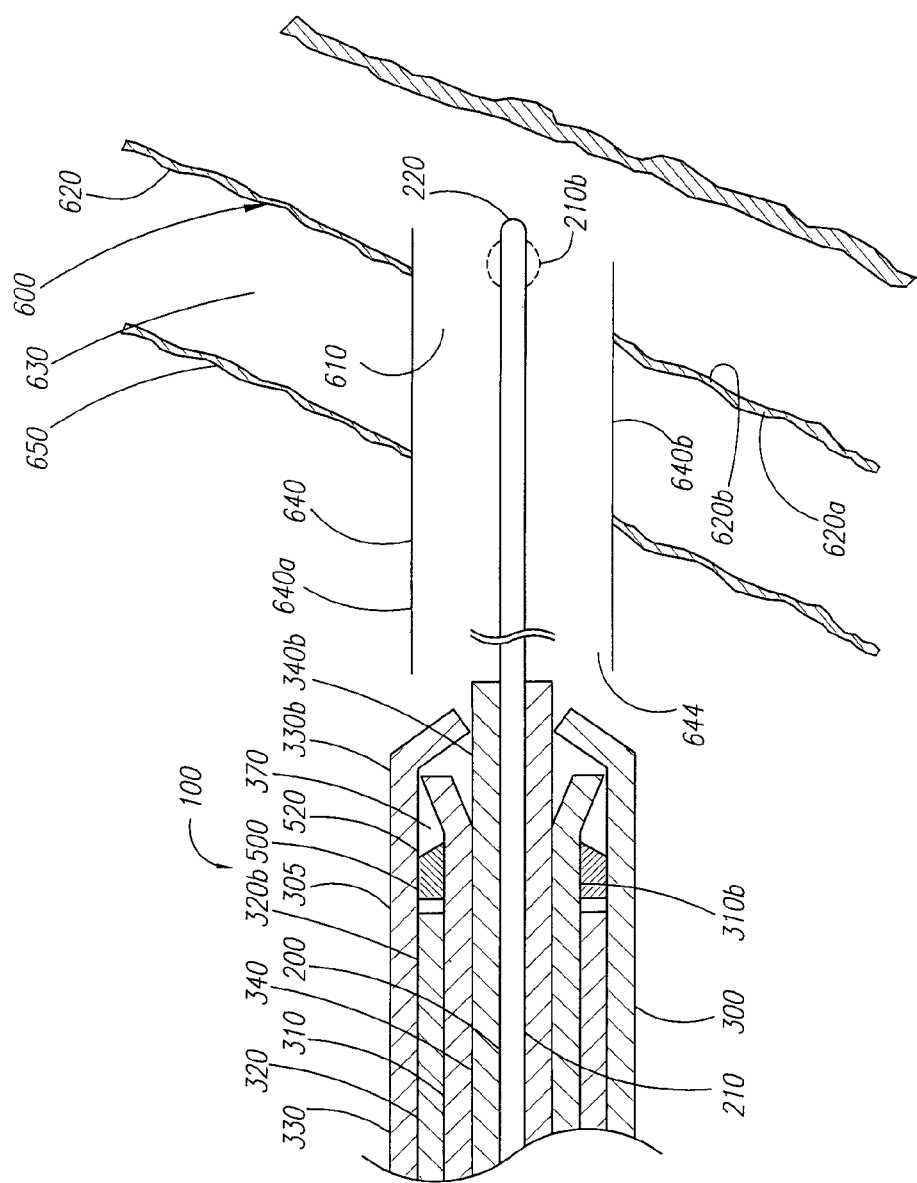
Figure 15C:
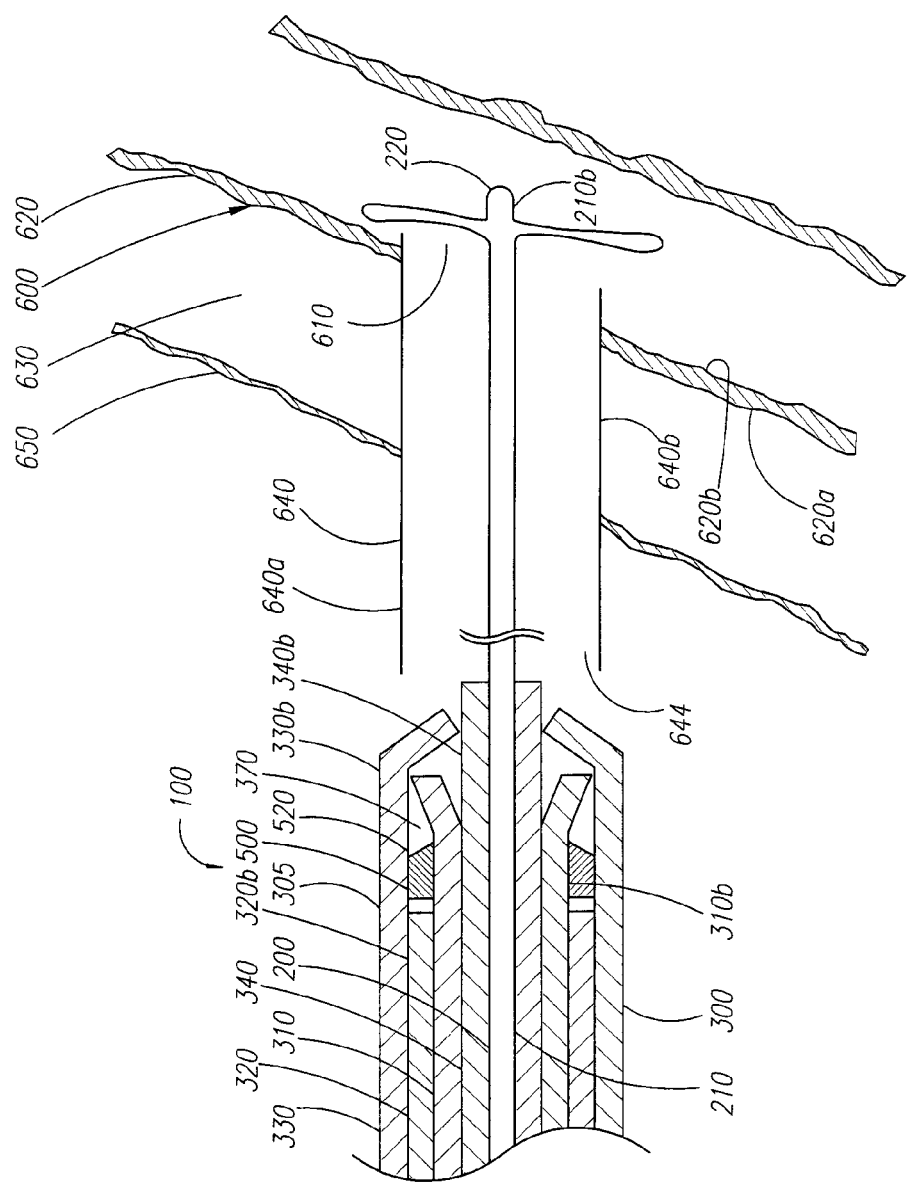

After the procedure is completed, the devices associated with the therapeutic or diagnostic procedure are removed from sheath 640, and apparatus 100 can be prepared to be received by lumen 644 of the sheath. Being in the unexpanded state, the distal end region 210*b* of tubular body 210 of the locator assembly 200 an be slidably received by the lumen and atraumatically advanced distally into the blood vessel 600, as illustrated in FIG. 15B. Once the distal end region 210*b* extends into blood vessel 600, distal end region 210*b* can transition from the unexpanded state to the expanded state by activating the switching system of locator assembly 200, and as illustrated in FIG. 15C. As discussed with reference to the embodiments described in reference to FIGS. 9-13, the carrier assembly may be partially advanced when the locator assembly is transitioned from the unexpanded to the expanded state by pressing the locator assembly block distally with respect to the housing.

Figure 15D:
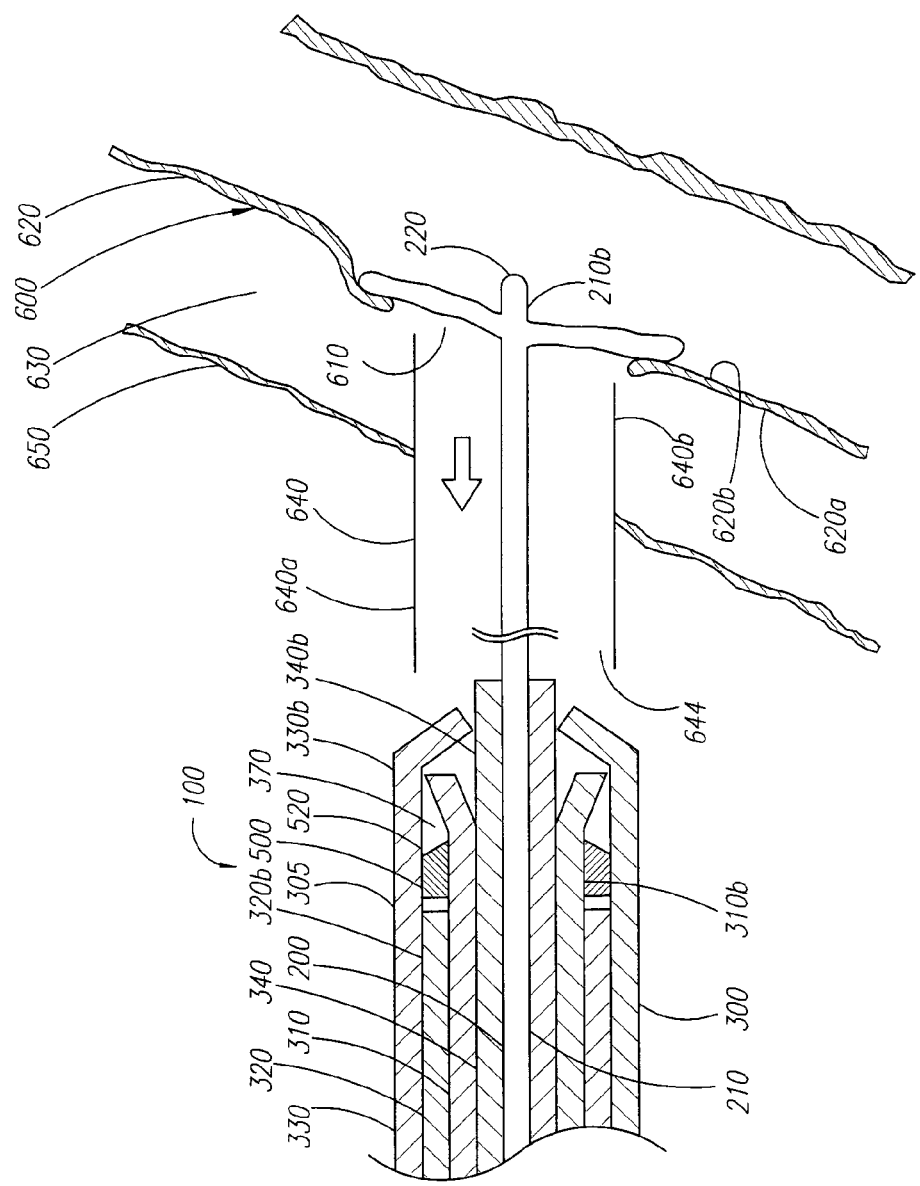
Figure 15E:
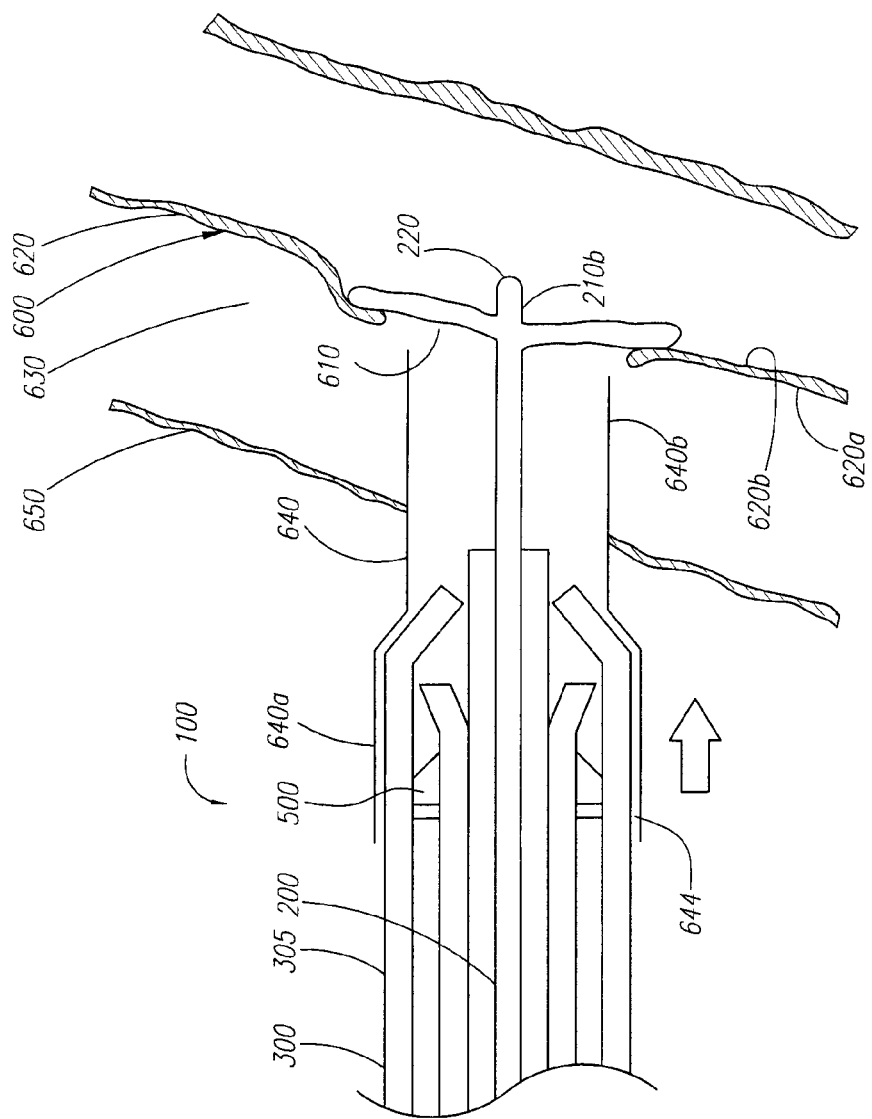

Turning to FIG. 15D, apparatus 100 and/or sheath 640 can then be retracted proximally until distal end region 210*b* is substantially adjacent to an outer surface 620*b* of blood vessel wall 620. Distal end region 210*b* thereby draws blood vessel wall 620 taut and maintains the proper position of apparatus 100 as blood vessel 600 pulsates. Since the expanded cross-section of distal end region 210*b* is greater than or substantially equal to the cross-section of opening 610 and/or the cross-section of lumen 644, distal end region 210*b* remains in blood vessel 600 and engages inner surface 620*b* of blood vessel wall 620. Distal end region 210*b* can frictionally engage inner surface 620*b* of blood vessel wall 620, thereby securing apparatus 100 to blood vessel 600. Sheath 640 can be retracted proximally such that distal end region 640*b* of sheath 640 is substantially withdrawn from blood vessel 600, permitting apparatus 100 to access blood vessel wall 620.

Figure 15F:
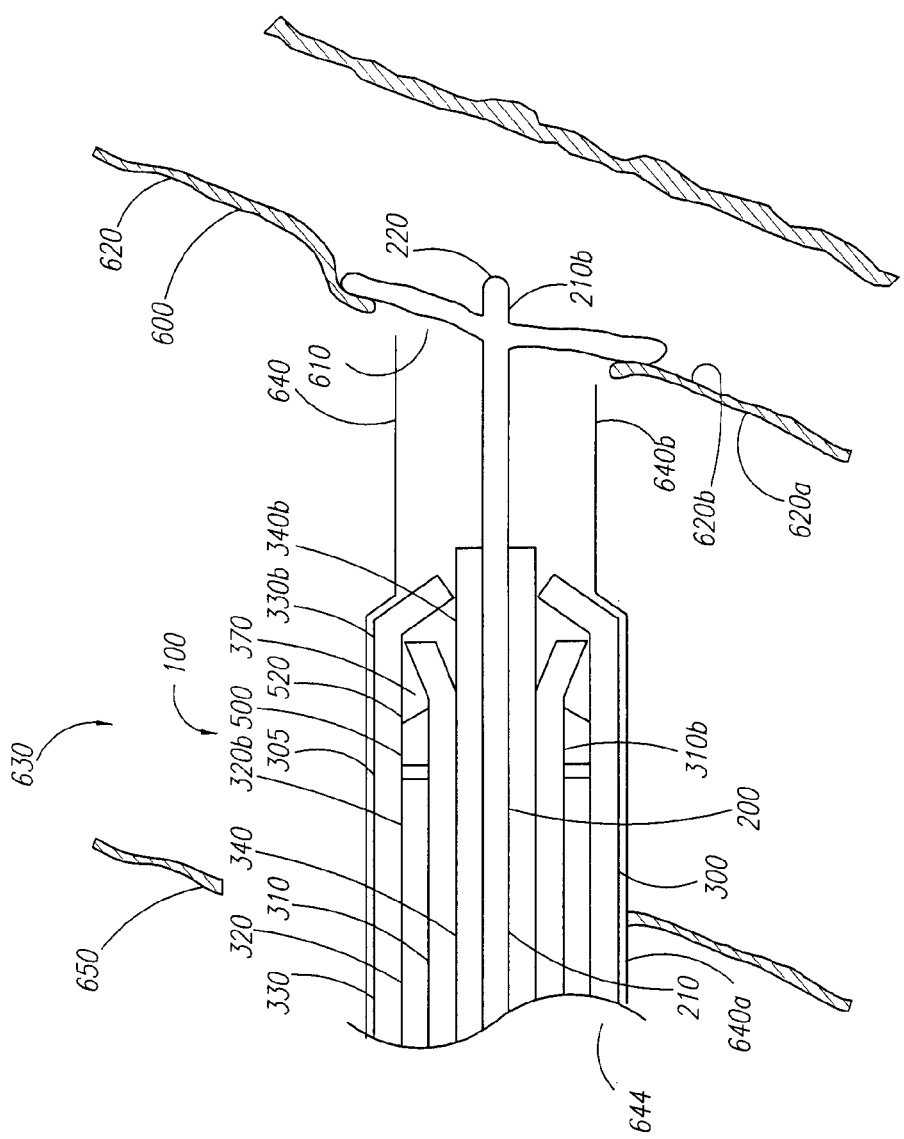

Once distal end region 210*b* of locator assembly 200 contacts inner surface 620*b* of blood vessel wall 620, tube set 305 can then be advanced distally and received within lumen 644 of sheath 640. In the manner described above, sheath 640 can radially expand and/or split in accordance with the predetermined pattern as tube set 305 advances because the internal cross-section of sheath 640 is less than or substantially equal to pre-determined cross-section 338*b* of cover member 330. Being coupled, carrier member 310, pusher member 320, cover member 330, and support member 340 each advance distally and approach the first predetermined position, as illustrated in FIG. 15F. As discussed with reference to the embodiments described in reference to FIGS. 9-13, a stable base can be provided by handle portion 1600 having an enlarged, curved configuration that can receive at least a thumb or finger of the physician. The enlarged, curved handle portion 1600 can griped by the physician while the physician's hand is rested upon a patient during the procedure and provide stability during use of the device. Additionally, the combined deployment of locator assembly 1110 and the partial advancement of carrier assembly 1120 in a single step allows for a reduction in travel of trigger extension 1405. Thus, a user does not need to reach uncomfortably far from handle portion 1602 to trigger extension 1405 to fully advance carrier assembly 1120 and the tube set coupled to the carrier assembly.

Upon reaching the first predetermined position, tube set 305 is disposed substantially adjacent to outer surface 620*a* of blood vessel wall 620 adjacent to opening 610 such that the blood vessel wall adjacent to opening 610 is disposed substantially between expanded distal region 210*b* of locator assembly 200 and tube set 305. Support member 340 decouples from carrier member 310 and pusher member 320 in the manner described above when tube set 305 is in the first predetermined position. The cover member 330 and pusher member 320 are advanced. After advancement the cover member 330 is decoupled from the carrier member 310 and pusher member 320. Thereby, cover member 330 and support member 340 may be inhibited from further axial movement and remain substantially stationary as carrier member 310 and pusher member 320 each remain coupled and axially slidable.

Figure 15G:
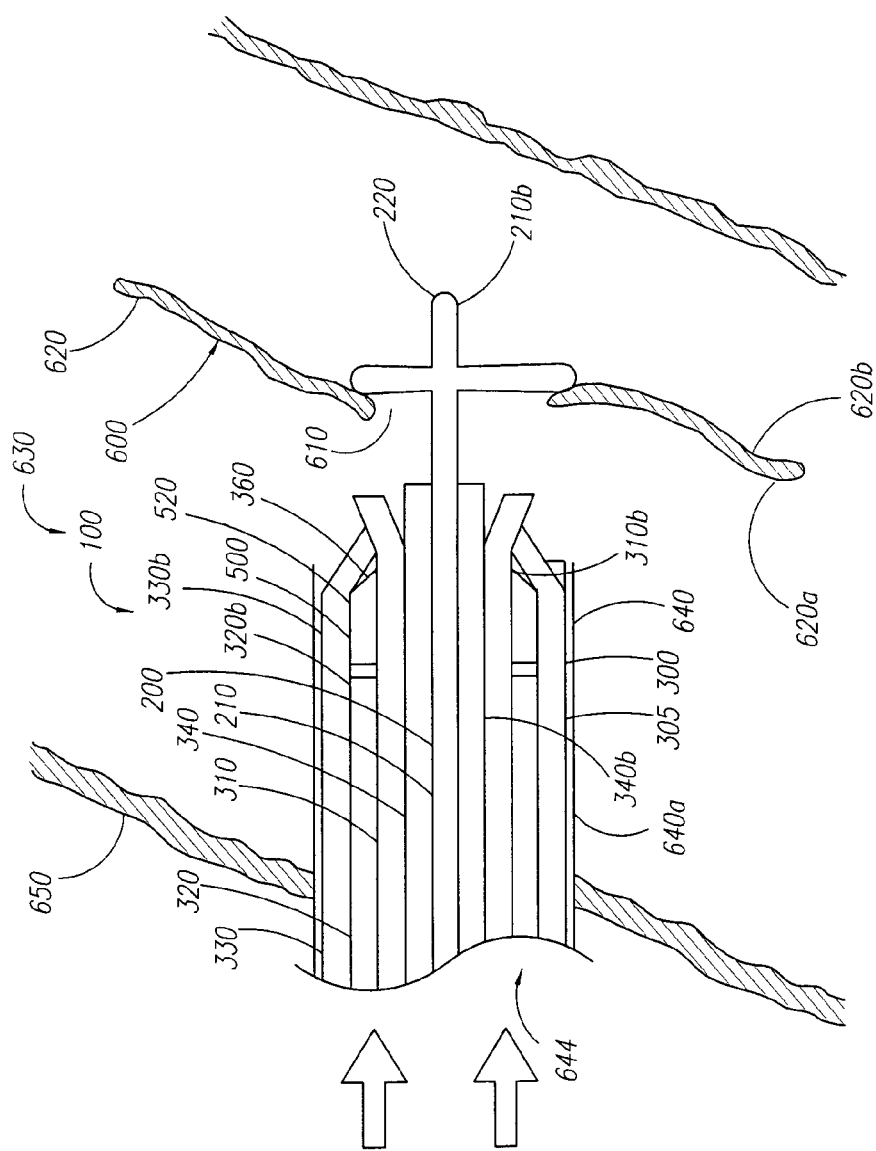

As shown in FIG. 15G, cover member 330 and support member 340 remain substantially stationary while carrier member 310 and pusher member 320 continue distally and approach the second predetermined position. As carrier member 310 and pusher member 320 distally advance toward the second predetermined position, annular cavity 370 moves distally relative to substantially-stationary cover member 330 such that distal end region 330*b* of cover member 330 no longer encloses annular cavity 370. Thereby, closure element 500 is not completely enclosed by annular cavity 370 formed by distal end regions 310*b*, 320*b*, and 330*b* of carrier member 310, pusher member 320, and cover member 330.

Although not completely enclosed by annular cavity 370, substantially tubular closure element 500 is advantageously retained on outer periphery 312*b* of carrier member 310 by distal end region 330*b* of cover member 330 as illustrated in FIG. 15G. For example, by retaining substantially tubular closure element 500 between distal end region 330b of cover member 330 and distal end region 310b carrier member 310, apparatus 100 may be configured to provide better tissue penetration. The timing between the deployment of substantially tubular closure element 500 by tube set 305 and the retraction and transition to the unexpanded state by locator assembly 200 likewise is facilitated because substantially tubular closure element 500 is retained between distal end region 330b and distal end region 310b. Further, carrier member 310 and cover member 330 operate to maintain substantially tubular closure element 500 in the tubular configuration.

Figure 15H:
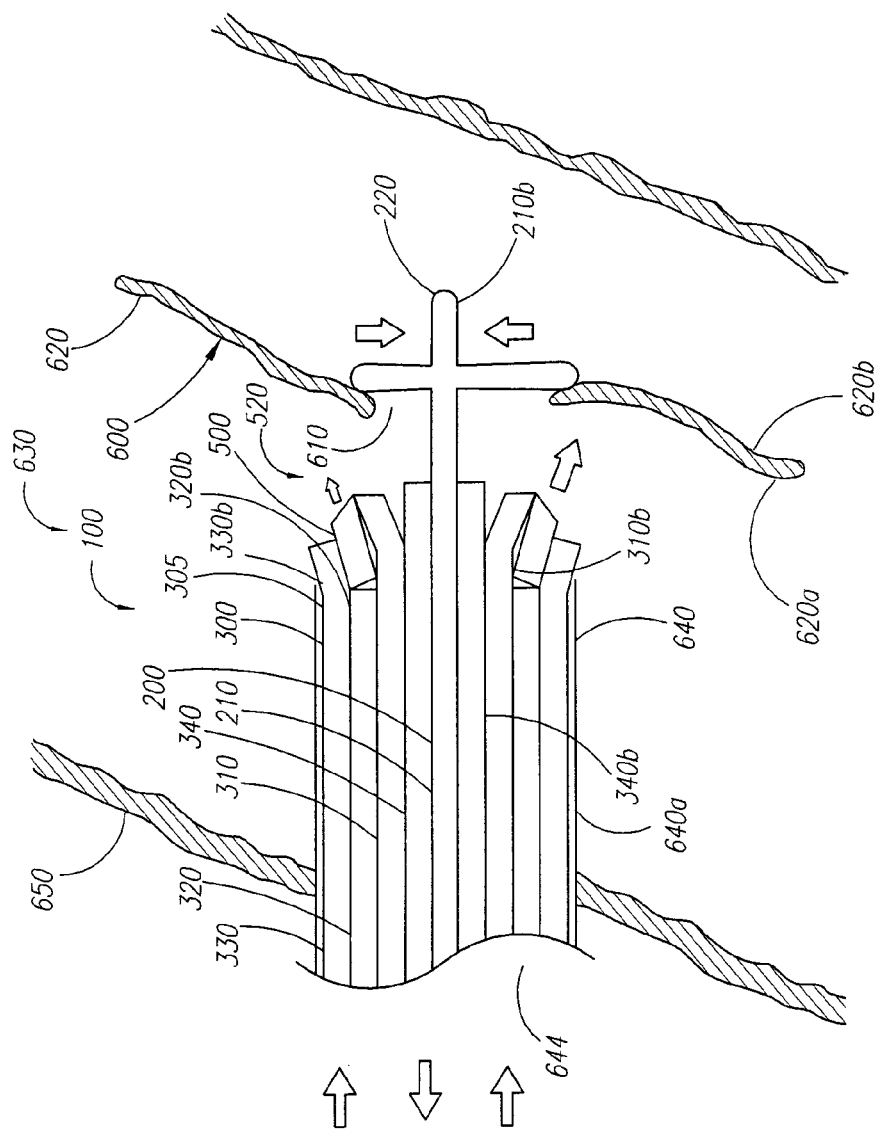

When tube set 305 is in the second predetermined position, carrier member 310 decouples from pusher member 320 in the manner described in detail above. Therefore, carrier member 310, cover member 330, and support member 340 may be inhibited from further axial movement and remain substantially stationary, whereas, pusher member 320 remains axially slidable. As pusher member 320 continues distally, distal end region 320b of pusher member 320 contacts substantially tubular closure element 500 and displaces substantially tubular closure element 500 from space 360 as shown in FIG. 15H. Since space 360 is substantially radially exposed, pusher member 320 directs substantially tubular closure element 500 over the distally-increasing cross-section of distal end region 310b of substantially-stationary carrier member 310 such that the cross-section of substantially tubular closure element 500 begins to radially expand, preferably in a substantially uniform manner. As substantially tubular closure element 500 traverses the distally-increasing cross-section of distal end region 310b, the cross-section of substantially tubular closure element 500 radially expands beyond natural cross-section of closure element 500, as shown in FIGS. 14A-G.

Figure 15I:
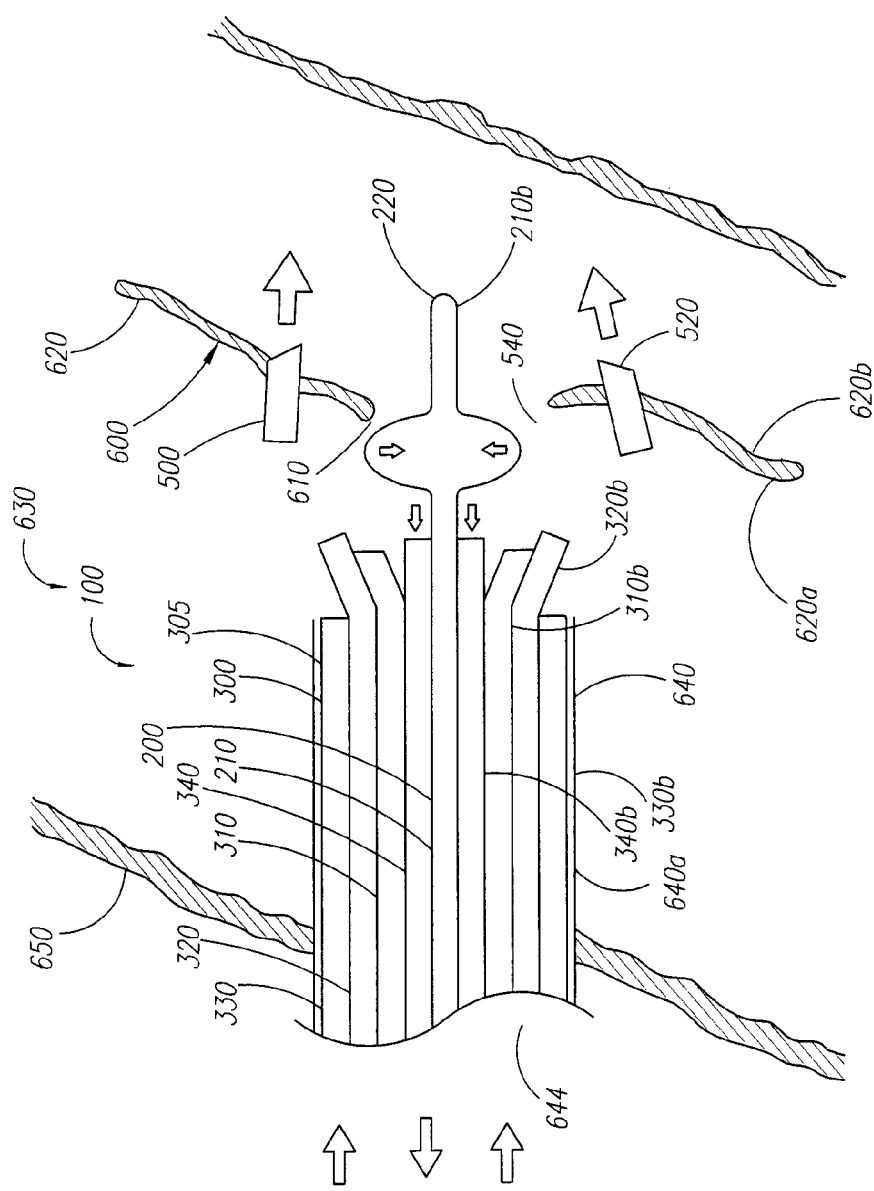

Upon being directed over the distally-increasing cross-section of the distal end region by pusher member 320, substantially tubular closure element 500 is distally deployed as illustrated in FIG. 15I. When substantially tubular closure element 500 is deployed, tines 520 can pierce and otherwise engage significant amount of blood vessel wall 620 and/or tissue 630 adjacent to opening 610. For example, tines 520 can engage significant amount of blood vessel wall 620 and/or tissue 630 because cross-section 530 of substantially tubular closure element 500 is expanded beyond natural cross-section 530 of closure element 500 during deployment.

As the closure element is being deployed from the space, locator assembly 200 may begins to retract proximally and locator release system 490 can be activated to transition from the expanded state to the unexpanded state as substantially tubular closure element 500 is deployed. Distal end region 210b of locator assembly 200 may retract proximally and transition from the expanded state to the unexpanded state substantially simultaneously with the deployment of substantially tubular closure element 500. As desired, distal end region 210b may be configured to draw blood vessel wall 620 and/or tissue 630 adjacent to opening 610 proximally and into the channel defined by substantially tubular closure element 500. Tines 520 of substantially tubular closure element 500 thereby can pierce and otherwise engage blood vessel wall 620 and/or tissue 630.

Figure 15J:
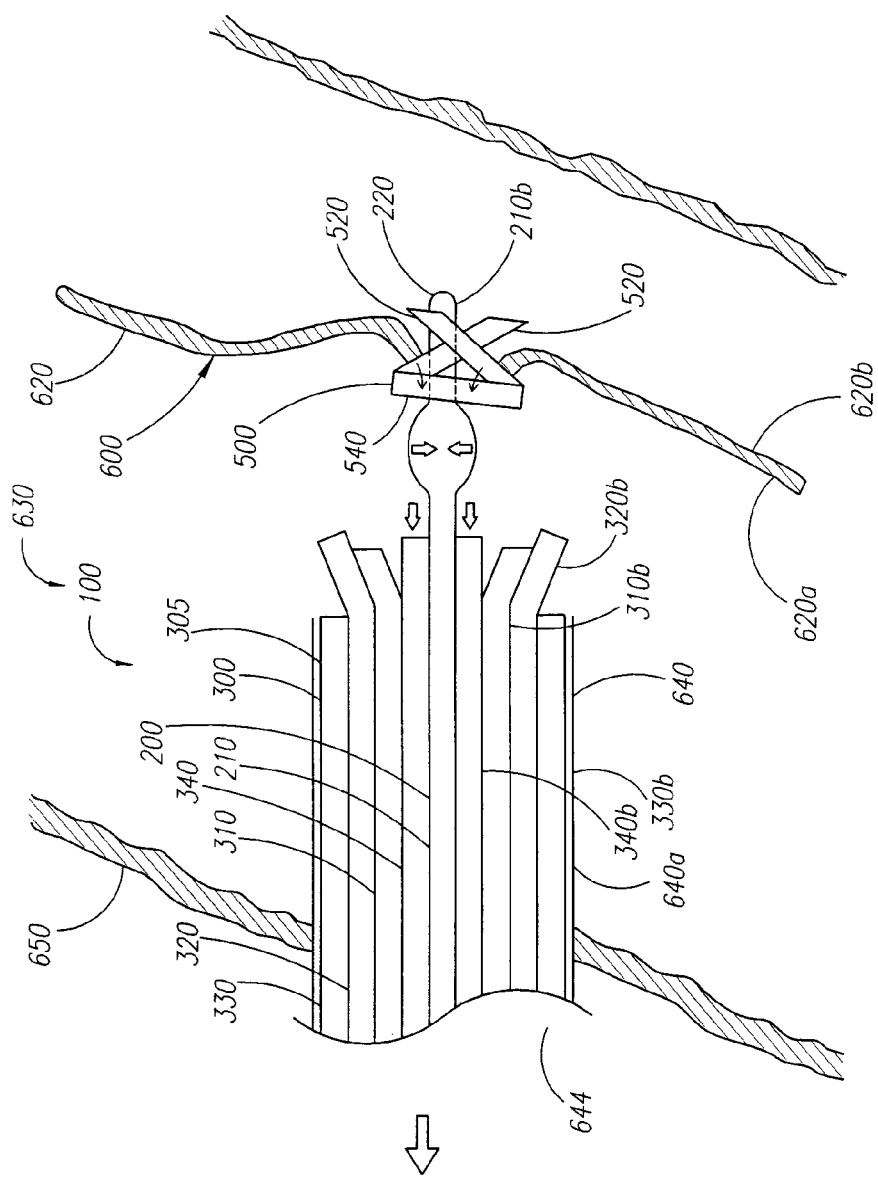
Figure 15K:
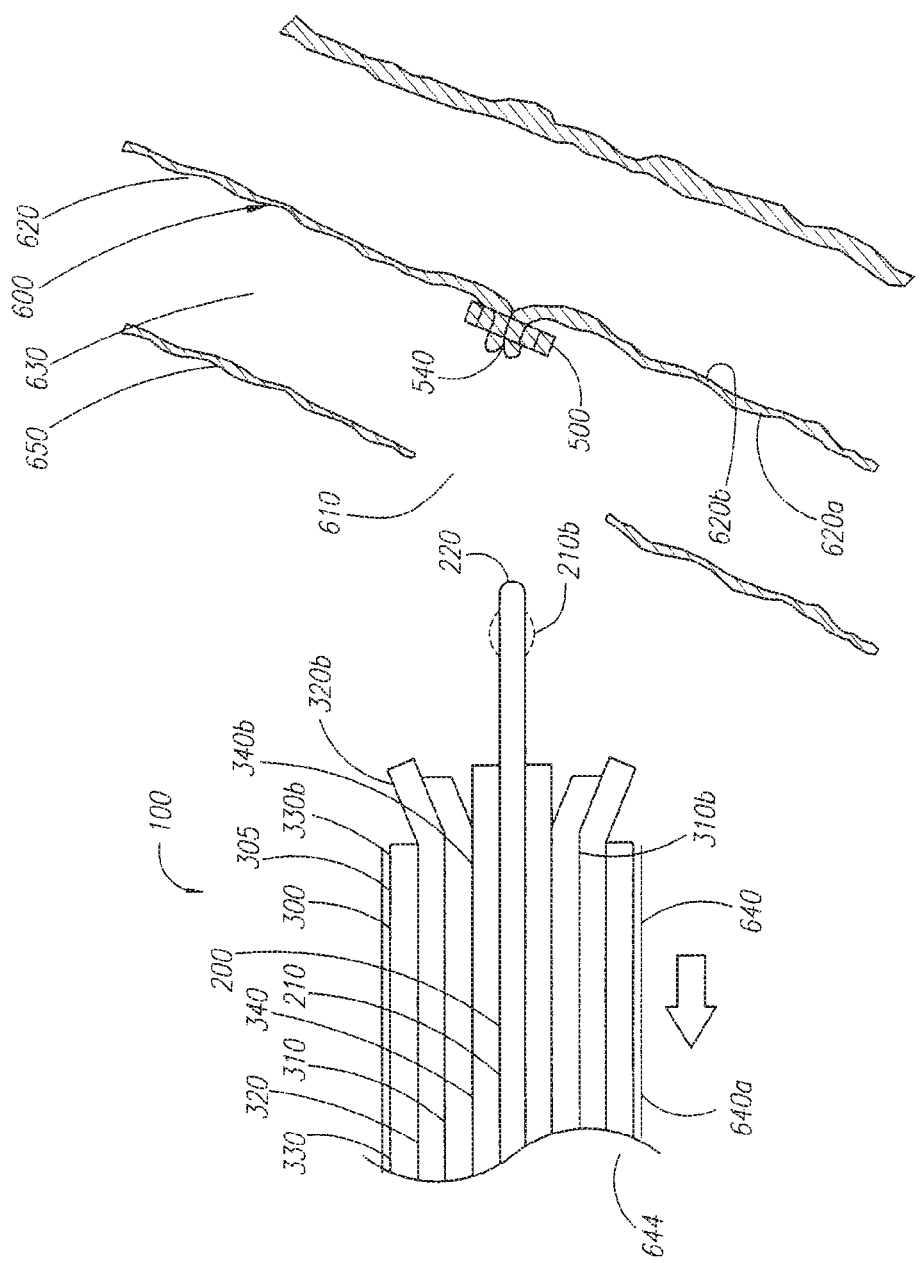

Turning to FIG. 15J, substantially tubular closure element 500, once deployed, begins to transition from the tubular configuration, returning to the natural, planar configuration with opposing tines 520 and a natural cross-section of closure element 500. Preferably, substantially tubular closure element 500 substantially uniformly transitions from the tubular configuration to the natural, planar configuration. Rotating axially inwardly to from opposing tines 520 of the closure element 500, tines 520 draw the tissue into the channel as substantially tubular closure 500 element forms closure element 500. Also, the tissue is drawn substantially closed and/or sealed as the cross-section of substantially tubular closure element 500 contracts to return to the natural cross-section.

It will be appreciated that the closure element may be constructed of other materials, that it may comprise alternative shapes, and that it may adopt alternative methods of operation such that the closure element achieves closure of openings in blood vessel walls or other body tissue. In an additional non-limiting example, the closure element is constructed of materials that use a magnetic force to couple a pair of securing elements in order to close an opening in the lumen wall or tissue. In this alternative embodiment, the closure element may be of a unitary or multi-component construction having a first securing element positionable at a first position adjacent the opening, and a second securing element positionable at a second position adjacent the opening. The first and second securing elements are provided having a magnetic force biasing the first and second securing elements together, thereby closing the opening, or they are provided having a magnetic force biasing both the first and second securing elements toward a third securing element positioned in a manner to cause closure of the opening. The magnetic closure element may be provided without tines, provided the magnetic force coupling the closure elements is sufficient to close the opening. Alternatively, the closure element may be provided with a combination of the magnetic securing elements and tines to provide a combination of coupling forces. Those skilled in the art will recognize that other and further materials, methods, and combinations may be utilized to construct the closure element to achieve the objectives described and implied herein.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

We claim:

1. A method for delivering a closure element to an opening formed in a wall of a body lumen, the method comprising:
    inserting a distal end region of an apparatus into the opening in the wall of the body lumen, the apparatus comprising a first grasping portion, a second grasping portion, a third grasping portion, and a fourth grasping portion, wherein the second grasping portion and the third grasping portion are movable toward the first grasping portion, the fourth grasping portion extends from an opposite side of the apparatus from the second grasping portion and extends transversely to a direction of a longitudinal axis of the apparatus;
    moving the third grasping portion toward the first grasping portion to limit movement of the distal end region of the apparatus relative to the opening in the wall of the body lumen; and
    moving the second grasping portion toward the first grasping portion to advance the closure element distally.

2. The method as recited in claim 1, wherein moving the third grasping portion deploys a locator across the opening.

3. The method as recited in claim 1, wherein moving the third grasping portion positions a member transverse to the opening.

4. The method as recited in claim 1, wherein moving the third grasping portion further comprises advancing a portion of the third grasping portion into a portion of a housing of the apparatus.

5. The method as recited in claim 1, further comprising releasing a locking member to allow a slidable proximal member to move distally toward the distal end region of the apparatus.

6. The method of claim 5, wherein releasing the locking member comprises moving the locking member from a locked state to an unlocked state.

7. The method of claim 1, wherein moving the second grasping portion disconnects the closure element from the apparatus.

8. A method for delivering a closure element to an opening formed in a wall of a body lumen, the method comprising:
 positioning a distal end region of an apparatus into the opening in the wall of the body lumen, the apparatus comprising a first grasping portion, a second grasping portion, a third grasping portion, and a fourth grasping portion, wherein the second grasping portion and third grasping portion are axially movable toward the first grasping portion, the fourth grasping portion extends from an opposite side of the apparatus from the second grasping portion and extends transversely to a direction of a longitudinal axis of the apparatus;
 moving the third grasping portion axially toward the first grasping portion to limit movement of the distal end region of the apparatus relative to the opening in the wall of the body lumen; and
 moving the second grasping portion axially toward the first grasping portion to advance the closure element distally in preparation to disconnect the closure element from the apparatus.

9. The method of claim 8, wherein one of the first grasping portion, the second grasping portion and the third grasping portion includes a through-hole.

10. The method of claim 8, wherein one of the first grasping portion, the second grasping portion and the third grasping portion is formed in a housing.

11. The method as recited in claim 8, wherein moving the third grasping portion positions a member transverse to the opening.

12. The method as recited in claim 11, wherein moving the third grasping portion moves a portion of the third grasping portion disposed outside of the apparatus into a portion of the apparatus.

13. The method of claim 8, wherein moving the second grasping portion disconnects the closure element from the apparatus.

14. The method of claim 8, further comprising removing the distal end region of the apparatus from the opening.

15. The method of claim 8, wherein the first grasping portion and the second grasping portion have complementary orientations.

16. A method for delivering a closure element to an opening formed in a wall of a body lumen, the method comprising:
 positioning a distal end region of an apparatus relative to the opening in the wall of the body lumen, the distal end region being movable between an expanded state and an unexpanded state, the apparatus comprising a first grasping portion, a second grasping portion, a third grasping portion, a fourth grasping portion, and a slidable member, the movement of which relative to a housing being limited by a locking member having a locked state and an unlocked state, wherein the second grasping portion and third grasping portion are axially movable toward the first grasping portion, the third grasping portion comprising an aperture and the fourth grasping portion extends from an opposite side of the apparatus from the second grasping portion and extends transversely to a direction of a longitudinal axis of the apparatus;
 moving the third grasping portion axially toward the first grasping portion to move the distal end region of the apparatus to the expanded state;
 moving the locking member from the locked state to the unlocked state;
 moving the slidable member distally to support the distal end region relative to the opening in the wall of the body lumen; and
 moving the second grasping portion axially toward the first grasping portion to advance the closure element distally and deploy the closure element from the apparatus.

17. The method as recited in claim 16, wherein moving the third grasping portion to move the distal end region of the apparatus to the expanded state comprises positioning a portion of the distal end region transverse to the opening.

18. The method as recited in claim 16, wherein moving the second grasping portion deploys the closure element into engagement with the tissue surrounding the opening.

19. The method as recited in claim 16, further comprising advancing a tubular member over a guide wire and removing the guide wire from the tubular member.

20. The method as received in claim 19, wherein positioning the distal end region of the apparatus relative to the opening in the wall of the body lumen comprising moving the distal end region relative to the tubular member.

* * * * *